United States Patent
Sawano et al.

(10) Patent No.: US 8,612,247 B2
(45) Date of Patent: Dec. 17, 2013

(54) BIOLOGICAL INFORMATION MANAGEMENT SYSTEM

(75) Inventors: Takao Sawano, Kyoto (JP); Kenji Yamamoto, Kyoto (JP); Tsutomu Kaneshige, Kyoto (JP)

(73) Assignee: Nintendo Co., Ltd., Kyoto (JP)

( * ) Notice: Subject to any disclaimer, the term of this patent is extended or adjusted under 35 U.S.C. 154(b) by 274 days.

(21) Appl. No.: 12/418,213

(22) Filed: Apr. 3, 2009

(65) Prior Publication Data

US 2010/0169110 A1 Jul. 1, 2010

(30) Foreign Application Priority Data

Dec. 26, 2008 (JP) ................................ 2008-334795

(51) Int. Cl.
G06Q 10/00 (2012.01)
A61B 5/00 (2006.01)
G06F 19/00 (2011.01)

(52) U.S. Cl.
USPC .................... 705/2; 705/3; 600/301

(58) Field of Classification Search
USPC ........................................................... 705/2
See application file for complete search history.

(56) References Cited

U.S. PATENT DOCUMENTS

| | | |
|---|---|---|
| 588,172 A | 8/1897 | Peters |
| 688,076 A | 12/1901 | Ensign |
| D188,376 S | 7/1960 | Hotkins et al. |
| 3,184,962 A | 5/1965 | Gay |
| 3,217,536 A | 11/1965 | Motsinger et al. |
| 3,424,005 A | 1/1969 | Brown |
| 3,428,312 A | 2/1969 | Machen |
| 3,712,294 A | 1/1973 | Muller |
| 3,752,144 A | 8/1973 | Weigle, Jr. |
| 3,780,817 A | 12/1973 | Videon |
| 3,826,145 A | 7/1974 | McFarland |
| 3,869,007 A | 3/1975 | Haggstrom et al. |
| 4,058,178 A | 11/1977 | Shinohara et al. |
| 4,104,119 A | 8/1978 | Schilling |
| 4,136,682 A | 1/1979 | Pedotti |
| 4,246,783 A | 1/1981 | Steven et al. |
| 4,296,931 A | 10/1981 | Yokoi |
| 4,337,050 A | 6/1982 | Engalitcheff, Jr. |

(Continued)

FOREIGN PATENT DOCUMENTS

| | | |
|---|---|---|
| DE | 40 04 554 | 8/1991 |
| DE | 195 02 918 | 8/1996 |

(Continued)

OTHER PUBLICATIONS

Vs. Slalom—Operation Manual, MDS(MGS), Nintendo, 4 pages, (date unknown).

(Continued)

*Primary Examiner* — Hiep V Nguyen
(74) *Attorney, Agent, or Firm* — Nixon & Vanderhye P.C.

(57) ABSTRACT

A healthcare professional terminal 90 creates a question message based on an input operation of a healthcare professional, and transmits the question message to a game apparatus 12. The game apparatus 12 creates, based on an input operation of a healthcare recipient, an answer message including an answer to a question contained in the question message received from the healthcare professional terminal 90, and transmits the answer message to the healthcare professional terminal 90 together with automatically obtained biological information (weight data, exercise time data, and step count data) of the healthcare recipient.

20 Claims, 25 Drawing Sheets

(56) References Cited

U.S. PATENT DOCUMENTS

| | | |
|---|---|---|
| 4,404,854 A | 9/1983 | Krempl et al. |
| 4,488,017 A | 12/1984 | Lee |
| 4,494,754 A | 1/1985 | Wagner, Jr. |
| 4,558,757 A | 12/1985 | Mori et al. |
| 4,569,519 A | 2/1986 | Mattox et al. |
| 4,574,899 A | 3/1986 | Griffin |
| 4,577,868 A | 3/1986 | Kiyonaga |
| 4,598,717 A | 7/1986 | Pedotti |
| 4,607,841 A | 8/1986 | Gala |
| 4,630,817 A | 12/1986 | Buckleu |
| 4,660,828 A | 4/1987 | Weiss |
| 4,680,577 A | 7/1987 | Straayer et al. |
| 4,688,444 A | 8/1987 | Nordstrom |
| 4,691,694 A | 9/1987 | Boyd et al. |
| 4,711,447 A | 12/1987 | Mansfield |
| 4,726,435 A | 2/1988 | Kitagawa et al. |
| 4,739,848 A | 4/1988 | Tulloch |
| 4,742,832 A | 5/1988 | Kauffmann et al. |
| 4,742,932 A | 5/1988 | Pedragosa |
| 4,800,973 A | 1/1989 | Angel |
| 4,838,173 A | 6/1989 | Schroeder et al. |
| 4,855,704 A | 8/1989 | Betz |
| 4,880,069 A | 11/1989 | Bradley |
| 4,882,677 A | 11/1989 | Curran |
| 4,893,514 A | 1/1990 | Gronert et al. |
| 4,907,797 A | 3/1990 | Gezari et al. |
| 4,927,138 A | 5/1990 | Ferrari |
| 4,970,486 A | 11/1990 | Gray et al. |
| 4,982,613 A | 1/1991 | Becker |
| D318,073 S | 7/1991 | Jang |
| 5,044,956 A | 9/1991 | Behensky et al. |
| 5,049,079 A | 9/1991 | Furtado et al. |
| 5,052,406 A | 10/1991 | Nashner |
| 5,054,771 A | 10/1991 | Mansfield |
| 5,065,631 A | 11/1991 | Ashpitel et al. |
| 5,089,960 A | 2/1992 | Sweeney, Jr. |
| 5,103,207 A | 4/1992 | Kerr et al. |
| 5,104,119 A | 4/1992 | Lynch |
| 5,116,296 A | 5/1992 | Watkins et al. |
| 5,118,112 A | 6/1992 | Bregman et al. |
| 5,151,071 A | 9/1992 | Jain et al. |
| 5,195,746 A | 3/1993 | Boyd et al. |
| 5,197,003 A | 3/1993 | Moncrief et al. |
| 5,199,875 A | 4/1993 | Trumbull |
| 5,203,563 A | 4/1993 | Loper, III |
| 5,207,426 A | 5/1993 | Inoue et al. |
| 5,259,252 A | 11/1993 | Kruse et al. |
| 5,269,318 A | 12/1993 | Nashner |
| 5,299,810 A | 4/1994 | Pierce et al. |
| 5,303,715 A | 4/1994 | Nashner et al. |
| 5,360,383 A | 11/1994 | Boren |
| 5,362,298 A | 11/1994 | Brown et al. |
| 5,368,546 A | 11/1994 | Stark et al. |
| 5,405,152 A | 4/1995 | Katanics et al. |
| 5,431,569 A | 7/1995 | Simpkins et al. |
| 5,462,503 A | 10/1995 | Benjamin et al. |
| 5,466,200 A | 11/1995 | Ulrich et al. |
| 5,469,740 A | 11/1995 | French et al. |
| 5,474,087 A | 12/1995 | Nashner |
| 5,476,103 A | 12/1995 | Nasher et al. |
| 5,507,708 A | 4/1996 | Ma |
| 5,541,621 A | 7/1996 | Nmngani |
| 5,541,622 A | 7/1996 | Engle et al. |
| 5,547,439 A | 8/1996 | Rawls et al. |
| 5,551,445 A | 9/1996 | Nashner |
| 5,551,693 A | 9/1996 | Goto et al. |
| 5,577,981 A | 11/1996 | Jarvik |
| D376,826 S | 12/1996 | Ashida |
| 5,584,700 A | 12/1996 | Feldman et al. |
| 5,584,779 A | 12/1996 | Knecht et al. |
| 5,591,104 A | 1/1997 | Andrus et al. |
| 5,613,690 A | 3/1997 | McShane et al. |
| 5,623,944 A | 4/1997 | Nashner |
| 5,627,327 A | 5/1997 | Zanakis |
| D384,115 S | 9/1997 | Wilkinson et al. |
| 5,669,773 A | 9/1997 | Gluck |
| 5,689,285 A | 11/1997 | Asher |
| 5,690,582 A | 11/1997 | Ulrich et al. |
| 5,697,791 A | 12/1997 | Nasher et al. |
| 5,713,794 A | 2/1998 | Shimojima et al. |
| 5,721,566 A | 2/1998 | Rosenberg et al. |
| 5,746,684 A | 5/1998 | Jordan |
| 5,785,630 A | 7/1998 | Bobick et al. |
| D397,164 S | 8/1998 | Goto |
| 5,788,618 A | 8/1998 | Joutras |
| 5,792,031 A | 8/1998 | Alton |
| 5,800,314 A | 9/1998 | Sakakibara et al. |
| 5,805,138 A | 9/1998 | Brawne et al. |
| 5,813,958 A | 9/1998 | Tomita |
| 5,814,740 A | 9/1998 | Cook et al. |
| 5,820,462 A | 10/1998 | Yokoi et al. |
| 5,825,308 A | 10/1998 | Rosenberg |
| 5,837,952 A | 11/1998 | Oshiro et al. |
| D402,317 S | 12/1998 | Goto |
| 5,846,086 A | 12/1998 | Bizzi et al. |
| 5,853,326 A | 12/1998 | Goto et al. |
| 5,854,622 A | 12/1998 | Brannon |
| 5,860,861 A | 1/1999 | Lipps et al. |
| 5,864,333 A | 1/1999 | O'Heir |
| 5,872,438 A | 2/1999 | Roston |
| 5,886,302 A | 3/1999 | Germanton et al. |
| 5,888,172 A | 3/1999 | Andrus et al. |
| 5,889,507 A | 3/1999 | Engle et al. |
| D407,758 S | 4/1999 | Isetani et al. |
| 5,890,995 A | 4/1999 | Bobick et al. |
| 5,897,457 A | 4/1999 | Mackovjak |
| 5,897,469 A | 4/1999 | Yalch |
| 5,901,612 A | 5/1999 | Letovsky |
| 5,902,214 A | 5/1999 | Makikawa et al. |
| 5,904,639 A | 5/1999 | Smyser et al. |
| D411,258 S | 6/1999 | Isetani et al. |
| 5,912,659 A | 6/1999 | Rutledge et al. |
| 5,919,092 A | 7/1999 | Yokoi et al. |
| 5,921,780 A | 7/1999 | Myers |
| 5,921,899 A | 7/1999 | Rose |
| 5,929,782 A | 7/1999 | Stark et al. |
| 5,947,824 A | 9/1999 | Minami et al. |
| 5,976,063 A | 11/1999 | Joutras et al. |
| 5,980,256 A | 11/1999 | Carmein |
| 5,980,429 A | 11/1999 | Nashner |
| 5,984,785 A | 11/1999 | Takeda et al. |
| 5,987,982 A | 11/1999 | Wenman et al. |
| 5,989,157 A | 11/1999 | Walton |
| 5,993,356 A | 11/1999 | Houston et al. |
| 5,997,439 A | 12/1999 | Ohsuga et al. |
| 6,001,015 A | 12/1999 | Nishiumi et al. |
| 6,007,428 A | 12/1999 | Nishiumi et al. |
| 6,010,465 A | 1/2000 | Nashner |
| D421,070 S | 2/2000 | Jang et al. |
| 6,037,927 A | 3/2000 | Rosenberg |
| 6,038,488 A | 3/2000 | Barnes et al. |
| 6,044,772 A | 4/2000 | Gaudette et al. |
| 6,063,046 A | 5/2000 | Allum |
| 6,086,518 A | 7/2000 | MacCready, Jr. |
| 6,102,803 A | 8/2000 | Takeda et al. |
| 6,102,832 A | 8/2000 | Tani |
| D431,051 S | 9/2000 | Goto |
| 6,113,237 A | 9/2000 | Ober et al. |
| 6,147,674 A | 11/2000 | Rosenberg et al. |
| 6,152,564 A | 11/2000 | Ober et al. |
| D434,769 S | 12/2000 | Goto |
| D434,770 S | 12/2000 | Goto |
| 6,155,926 A | 12/2000 | Miyamoto et al. |
| 6,162,189 A | 12/2000 | Girone et al. |
| 6,167,299 A | 12/2000 | Galchenkov et al. |
| 6,190,287 B1 | 2/2001 | Nashner |
| 6,200,253 B1 | 3/2001 | Nishiumi et al. |
| 6,203,432 B1 | 3/2001 | Roberts et al. |
| 6,216,542 B1 | 4/2001 | Stockli et al. |
| 6,216,547 B1 | 4/2001 | Lehtovaara |
| 6,220,865 B1 | 4/2001 | Macri et al. |
| D441,369 S | 5/2001 | Goto |
| 6,225,977 B1 | 5/2001 | Li |
| 6,227,968 B1 | 5/2001 | Suzuki et al. |

(56) References Cited

U.S. PATENT DOCUMENTS

| | | |
|---|---|---|
| 6,228,000 B1 | 5/2001 | Jones |
| 6,231,444 B1 | 5/2001 | Goto |
| 6,239,806 B1 | 5/2001 | Nishiumi et al. |
| 6,241,611 B1 | 6/2001 | Takeda et al. |
| 6,244,987 B1 | 6/2001 | Ohsuga et al. |
| D444,469 S | 7/2001 | Goto |
| 6,264,558 B1 | 7/2001 | Nishiumi et al. |
| 6,280,361 B1 | 8/2001 | Harvey et al. |
| D447,968 S | 9/2001 | Pagnacco et al. |
| 6,295,878 B1 | 10/2001 | Berme |
| 6,296,595 B1 | 10/2001 | Stark et al. |
| 6,325,718 B1 | 12/2001 | Nishiumi et al. |
| 6,330,837 B1 | 12/2001 | Charles et al. |
| 6,336,891 B1 | 1/2002 | Fedrigon et al. |
| 6,353,427 B1 | 3/2002 | Rosenberg |
| 6,354,155 B1 | 3/2002 | Berme |
| 6,357,827 B1 | 3/2002 | Brightbill et al. |
| 6,359,613 B1 | 3/2002 | Poole |
| D456,410 S | 4/2002 | Ashida |
| D456,854 S | 5/2002 | Ashida |
| D457,570 S | 5/2002 | Brinson |
| 6,387,061 B1 | 5/2002 | Nitto |
| 6,388,655 B1 | 5/2002 | Leung |
| 6,389,883 B1 | 5/2002 | Berme et al. |
| 6,394,905 B1 | 5/2002 | Takeda et al. |
| 6,402,635 B1 | 6/2002 | Nesbit et al. |
| D459,727 S | 7/2002 | Ashida |
| D460,506 S | 7/2002 | Tamminga et al. |
| 6,421,056 B1 | 7/2002 | Nishiumi et al. |
| 6,436,058 B1 | 8/2002 | Krahner et al. |
| D462,683 S | 9/2002 | Ashida |
| 6,454,679 B1 | 9/2002 | Radow |
| 6,461,297 B1 | 10/2002 | Pagnacco et al. |
| 6,470,302 B1 | 10/2002 | Cunningham et al. |
| 6,482,010 B1 | 11/2002 | Marcus et al. |
| 6,510,749 B1 | 1/2003 | Pagnacco et al. |
| 6,514,145 B1 | 2/2003 | Kawabata et al. |
| 6,515,593 B1 | 2/2003 | Stark et al. |
| 6,516,221 B1 | 2/2003 | Hirouchi et al. |
| D471,594 S | 3/2003 | Nojo |
| 6,543,769 B1 | 4/2003 | Podoloff et al. |
| 6,563,059 B2 | 5/2003 | Lee |
| 6,568,334 B1 | 5/2003 | Guadette et al. |
| 6,616,579 B1 | 9/2003 | Reinbold et al. |
| 6,624,802 B1 | 9/2003 | Klein et al. |
| 6,632,158 B1 | 10/2003 | Nashner |
| 6,636,161 B2 | 10/2003 | Rosenberg |
| 6,636,197 B1 | 10/2003 | Goldenberg et al. |
| 6,638,175 B2 | 10/2003 | Lee et al. |
| 6,663,058 B1 | 12/2003 | Peterson et al. |
| 6,676,520 B2 | 1/2004 | Nishiumi et al. |
| 6,676,569 B1 | 1/2004 | Radow |
| 6,679,776 B1 | 1/2004 | Nishiumi et al. |
| 6,697,049 B2 | 2/2004 | Lu |
| 6,719,667 B2 | 4/2004 | Wong et al. |
| 6,726,566 B2 | 4/2004 | Komata |
| 6,764,429 B1 | 7/2004 | Michalow |
| 6,797,894 B2 | 9/2004 | Montagnino et al. |
| 6,811,489 B1 | 11/2004 | Shimizu et al. |
| 6,813,966 B2 | 11/2004 | Dukart |
| 6,817,973 B2 | 11/2004 | Merril et al. |
| D500,100 S | 12/2004 | van der Meer |
| 6,846,270 B1 | 1/2005 | Etnyre |
| 6,859,198 B2 | 2/2005 | Onodera et al. |
| 6,872,139 B2 | 3/2005 | Sato et al. |
| 6,872,187 B1 | 3/2005 | Stark et al. |
| 6,888,076 B2 | 5/2005 | Hetherington |
| 6,913,559 B2 | 7/2005 | Smith |
| 6,936,016 B2 | 8/2005 | Berme et al. |
| D510,391 S | 10/2005 | Merril et al. |
| 6,975,302 B1 | 12/2005 | Ausbeck, Jr. |
| 6,978,684 B2 | 12/2005 | Nurse |
| 6,991,483 B1 | 1/2006 | Milan et al. |
| D514,627 S | 2/2006 | Merril et al. |
| 7,004,787 B2 | 2/2006 | Milan |
| D517,124 S | 3/2006 | Merril et al. |
| 7,011,605 B2 | 3/2006 | Shields |
| 7,033,176 B2 | 4/2006 | Feldman et al. |
| 7,038,855 B2 | 5/2006 | French et al. |
| 7,040,986 B2 | 5/2006 | Koshima et al. |
| 7,070,542 B2 | 7/2006 | Reyes et al. |
| 7,083,546 B2 | 8/2006 | Zillig et al. |
| 7,100,439 B2 | 9/2006 | Carlucci |
| 7,121,982 B2 | 10/2006 | Feldman |
| 7,126,584 B1 | 10/2006 | Nishiumi et al. |
| 7,127,376 B2 | 10/2006 | Nashner |
| 7,163,516 B1 | 1/2007 | Pagnacco et al. |
| 7,179,234 B2 | 2/2007 | Nashner |
| 7,195,355 B2 | 3/2007 | Nashner |
| 7,202,424 B2 | 4/2007 | Carlucci |
| 7,202,851 B2 | 4/2007 | Cunningham et al. |
| 7,270,630 B1 | 9/2007 | Patterson |
| 7,307,619 B2 | 12/2007 | Cunningham et al. |
| 7,308,831 B2 | 12/2007 | Cunningham et al. |
| 7,331,226 B2 | 2/2008 | Feldman et al. |
| 7,335,134 B1 | 2/2008 | LaVelle |
| RE40,427 E | 7/2008 | Nashner |
| 7,416,537 B1 | 8/2008 | Stark et al. |
| 7,530,929 B2 | 5/2009 | Feldman et al. |
| 7,722,501 B2 | 5/2010 | Nicolas et al. |
| 7,938,751 B2 | 5/2011 | Nicolas et al. |
| 2001/0001303 A1 | 5/2001 | Ohsuga et al. |
| 2001/0018363 A1 | 8/2001 | Goto et al. |
| 2001/0050683 A1 | 12/2001 | Ishikawa et al. |
| 2002/0055422 A1 | 5/2002 | Airmet et al. |
| 2002/0080115 A1 | 6/2002 | Onodera et al. |
| 2002/0185041 A1 | 12/2002 | Herbst |
| 2003/0054327 A1 | 3/2003 | Evensen |
| 2003/0069108 A1 | 4/2003 | Kaiserman et al. |
| 2003/0107502 A1 | 6/2003 | Alexander et al. |
| 2003/0176770 A1 | 9/2003 | Merril et al. |
| 2003/0182067 A1* | 9/2003 | Asano et al. ............ 702/19 |
| 2003/0193416 A1 | 10/2003 | Ogata et al. |
| 2004/0038786 A1 | 2/2004 | Kuo et al. |
| 2004/0041787 A1 | 3/2004 | Graves |
| 2004/0077464 A1 | 4/2004 | Feldman et al. |
| 2004/0099513 A1 | 5/2004 | Hetherington |
| 2004/0110602 A1 | 6/2004 | Feldman |
| 2004/0127337 A1 | 7/2004 | Nashner |
| 2004/0163855 A1 | 8/2004 | Carlucci |
| 2004/0180719 A1 | 9/2004 | Feldman et al. |
| 2004/0259688 A1 | 12/2004 | Stabile |
| 2005/0070154 A1 | 3/2005 | Milan |
| 2005/0076161 A1 | 4/2005 | Albanna et al. |
| 2005/0130742 A1 | 6/2005 | Feldman et al. |
| 2005/0202384 A1 | 9/2005 | DiCuccio et al. |
| 2006/0097453 A1 | 5/2006 | Feldman et al. |
| 2006/0161045 A1 | 7/2006 | Merril et al. |
| 2006/0181021 A1 | 8/2006 | Seelig et al. |
| 2006/0205565 A1 | 9/2006 | Feldman et al. |
| 2006/0211543 A1 | 9/2006 | Feldman et al. |
| 2006/0217243 A1 | 9/2006 | Feldman et al. |
| 2006/0223634 A1 | 10/2006 | Feldman et al. |
| 2006/0258512 A1 | 11/2006 | Nicolas et al. |
| 2007/0021279 A1 | 1/2007 | Jones |
| 2007/0027369 A1 | 2/2007 | Pagnacco et al. |
| 2007/0155589 A1 | 7/2007 | Feldman et al. |
| 2007/0219050 A1 | 9/2007 | Merril |
| 2008/0012826 A1 | 1/2008 | Cunningham et al. |
| 2008/0076978 A1* | 3/2008 | Ouchi et al. ............ 600/301 |
| 2008/0228110 A1 | 9/2008 | Berme |
| 2008/0261696 A1 | 10/2008 | Yamazaki et al. |
| 2009/0093315 A1 | 4/2009 | Matsunaga et al. |
| 2010/0137063 A1 | 6/2010 | Shirakawa et al. |
| 2011/0070953 A1 | 3/2011 | Konishi |
| 2011/0077899 A1 | 3/2011 | Hayashi et al. |
| 2011/0207534 A1 | 8/2011 | Meldeau |

FOREIGN PATENT DOCUMENTS

| | | |
|---|---|---|
| DE | 297 12 785 | 1/1998 |
| DE | 20 2004 021 792 | 5/2011 |
| DE | 20 2004 021 793 | 5/2011 |
| EP | 0 275 665 | 7/1988 |

(56) References Cited

FOREIGN PATENT DOCUMENTS

| | | |
|---|---|---|
| EP | 0 299 738 | 1/1989 |
| EP | 0 335 045 | 10/1989 |
| EP | 0 519 836 | 12/1992 |
| EP | 1 043 746 | 11/2000 |
| EP | 1 120 083 | 8/2001 |
| EP | 1 257 599 | 8/2001 |
| EP | 1 394 707 | 3/2004 |
| EP | 1 870 141 | 12/2007 |
| FR | 2 472 929 | 7/1981 |
| FR | 2 587 611 | 3/1987 |
| FR | 2 604 910 | 4/1988 |
| FR | 2 647 331 | 11/1990 |
| FR | 2 792 182 | 10/2000 |
| FR | 2 801 490 | 6/2001 |
| FR | 2 811 753 | 1/2002 |
| FR | 2 906 365 | 3/2008 |
| GB | 1 209 954 | 10/1970 |
| GB | 2 288 550 | 10/1995 |
| JP | 44-23551 | 10/1969 |
| JP | 55-95758 | 12/1978 |
| JP | 54-73689 | 6/1979 |
| JP | 55-113472 | 9/1980 |
| JP | 55-113473 | 9/1980 |
| JP | 55-125369 | 9/1980 |
| JP | 55-149822 | 11/1980 |
| JP | 55-152431 | 11/1980 |
| JP | 60-79460 | 6/1985 |
| JP | 60-153159 | 10/1985 |
| JP | 61-154689 | 7/1986 |
| JP | 62-34016 | 2/1987 |
| JP | 63-158311 | 10/1988 |
| JP | 63-163855 | 10/1988 |
| JP | 63-193003 | 12/1988 |
| JP | 02-102651 | 4/1990 |
| JP | 2-238327 | 9/1990 |
| JP | 3-25325 | 2/1991 |
| JP | 3-103272 | 4/1991 |
| JP | 03-107959 | 11/1991 |
| JP | 6-063198 | 3/1994 |
| JP | 6-282373 | 10/1994 |
| JP | 07-213741 | 8/1995 |
| JP | 7-213745 | 8/1995 |
| JP | 7-241281 | 9/1995 |
| JP | 7-241282 | 9/1995 |
| JP | 7-275307 | 10/1995 |
| JP | 07-302161 | 11/1995 |
| JP | 8-43182 | 2/1996 |
| JP | 08-131594 | 5/1996 |
| JP | 08-182774 | 7/1996 |
| JP | 08-184474 | 7/1996 |
| JP | 8-215176 | 8/1996 |
| JP | 08-244691 | 9/1996 |
| JP | 2576247 | 1/1997 |
| JP | 9-120464 | 5/1997 |
| JP | 9-168529 | 6/1997 |
| JP | 9-197951 | 7/1997 |
| JP | 9-305099 | 11/1997 |
| JP | 11-151211 | 6/1999 |
| JP | 11-309270 | 11/1999 |
| JP | 2000-146679 | 5/2000 |
| JP | U3068681 | 5/2000 |
| JP | U3069287 | 6/2000 |
| JP | 2000-254348 | 9/2000 |
| JP | 3172738 | 6/2001 |
| JP | 2001-178845 | 7/2001 |
| JP | 2001-286451 | 10/2001 |
| JP | 2002-049697 | 2/2002 |
| JP | 2002-112984 | 4/2002 |
| JP | 2002-157081 | 5/2002 |
| JP | 2002-253534 | 9/2002 |
| JP | 2002-366664 | 12/2002 |
| JP | 2003-79599 | 3/2003 |
| JP | 2003-235834 | 8/2003 |
| JP | 2004-118339 | 4/2004 |
| JP | 3722678 | 11/2005 |
| JP | 2005-334083 | 12/2005 |
| JP | 3773455 | 5/2006 |
| JP | 2006-155462 | 6/2006 |
| JP | 2006-167094 | 6/2006 |
| JP | 3818488 | 9/2006 |
| JP | 2006-263101 | 10/2006 |
| JP | 2006-284539 | 10/2006 |
| JP | U3128216 | 12/2006 |
| JP | 2008-49117 | 3/2008 |
| JP | 2008-197784 | 8/2008 |
| JP | 2008-310606 | 12/2008 |
| WO | WO 91/11221 | 8/1991 |
| WO | WO 92/12768 | 8/1992 |
| WO | WO 98/40843 | 9/1998 |
| WO | WO 00/12041 | 3/2000 |
| WO | WO 00/57387 | 9/2000 |
| WO | WO 00/69523 | 11/2000 |
| WO | WO 02/29375 | 4/2002 |
| WO | WO 02/057885 | 7/2002 |
| WO | 03/067484 | 8/2003 |
| WO | WO 2004/051201 | 6/2004 |
| WO | WO 2004/053629 | 6/2004 |
| WO | WO 2005/043322 | 5/2005 |
| WO | WO 2008/034965 | 3/2008 |
| WO | WO 2008/099582 | 8/2008 |

OTHER PUBLICATIONS

HyperspaceArcade.com—Specialists in Arcade Video Game Repair and Restoration, http://www.hyperspacearcade.com/VSTypes.html (retrieved Jul. 3, 2010), 3 pages.

Vs. Slalom—Attachment Pak Manual; For Installation in: VS. UniSystem (UPRIGHT) and VS. DualSystem (UPRIGHT), TM of Nintendo of America Inc., 1986, 15 pages.

Leiterman, "Project Puffer: Jungle River Cruise," Atari, Inc., 1982, 2 pages.

Leiterman, "Project Puffer: Tumbleweeds," Atari, Inc., 1982, 1 page.

Jerry Smith, "Other Input Devices," Human Interface Technology Laboratory, 2 pages, (date unknown).

Trevor Meers, "Virtually There: VR Entertainment Transports Players to Entrancing New Worlds," Smart Computing, vol. 4, Issue 11, Nov. 1993, 6 pages.

"Dance Aerobics," Moby Games, Feb. 12, 2008, 2 pages.

Electronic Entertainment Expo (E3) Overview, Giant Bomb—E3 2004 (video game concept), http://www.giantbomb.com/e3-2004/92/3436/ (retrieved Sep. 3, 2010), 3 pages.

Michael Goldstein, "Revolution on Wheels—Thatcher Ulrich," Nov.-Dec. 1994, 3 pages.

Fitness article, Sep. 1994, p. 402-404.

"Wired Top 10: Best Selling Toys in Jun. 1994," Wired Sep. 1994, 1 page.

Warranty Information and Your Joyboard: How it Works, Amiga Corporation, date unknown, 2 pages.

Complaint for Patent Infringement, *IA Labs CA, LLC v. Nintendo Co., Ltd.* and *Nintendo of America, Inc.*, United States District Court for the District of Maryland Northern Division (Apr. 2, 2010), 317 pages.

Plaintiff IA Labs CA, LLC's Opening Claim Construction Brief, *IA Labs CA, LLC v. Nintendo Co., Ltd.* and *Nintendo of America, Inc.*, United States District Court for the District of Maryland Southern Division (Dec. 13, 2010), 36 pages.

Nintendo Co., Ltd. and Nintendo of America's Opposition to IA Labs CA, LLC's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), including the Appendix of Exhibits and Exhibits A-R, 405 pages.

Declaration of R. Lee Rawls in Support of Nintendo Co., Ltd. and Nintendo of America Inc.'s Opposition to IA Labs CA. LLC's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), including Exhibits 1, 3-12, 193 pages.

Declaration of Tyler C. Peterson Pursuant to Fed. R. Civ. p. 56(D) in Support of Nintendo Co., Ltd. and Nintendo of American Inc.'s

(56) References Cited

OTHER PUBLICATIONS

Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), 7 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Appendix of Exhibits, 2 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 1, 36 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 2, 40 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 3, 85 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 4, 10 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 5, 9 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 6, 17 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 7, 16 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 8, 45 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 9, 4 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 10, 22 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 11, 27 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 12, 3 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 13, 7 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 14, 22 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 15, 45 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 16, 42 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 17, 19 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 18, 27 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 19, 13 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 20, 29 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 21, 25 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant),

(56) References Cited

OTHER PUBLICATIONS

United States District Court for the District of Maryland Southern Division (May 16, 2011), Exhibit 22, 11 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 23, 20 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 24, 7 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 25, 80 pages.
Declaration of Tyler C. Peterson Pursuant to Fed. R. Civ. p. 56(D) in Support of Nintendo Co., Ltd. and Nintendo of American Inc.'s Opposition to Plaintiff's Motion for Partial Summary Judgment, *IA Labs CA, LLC*, (Plaintiff) v. *Nintendo Co., Ltd. et al.*, (Defendant), United States District Court for the District of Maryland Southern Division (May 16, 2011), Exhibit 26, 32 pages.
U.S. Trademark Application No. 74/402,755 filed Jun. 14, 1993, 43 pages.
"AccuSway Dual Top: For Balance and Postural Sway Measurement," AMTI: Force and Motion, ISO 9001:2000, 2 pages.
Borzelli G., Cappozzo A., and Papa E., "Inter- and intra-individual variability of ground rejection forces during sit-to-stand with principal component analysis," Medical Engineering & Physics 21 (1999), pp. 235-240.
Chiari L., Cappello A., Lenzi D., and Della Croce U, "An Improved Technique for the Extraction of Stochasitc Parameters from Stabilograms," Gait and Posture 12 (2000), pp. 225-234.
Cutlip R., Hsiao H., Garcia R., Becker E., Mayeux B., "A comparison of different postures for scaffold end-frame disassembly," Applied Ergonomics 31 (2000), pp. 507-513.
Davis K.G., Marras W.S., Waters T.R., "Evaluation of spinal loading during lowering and lifting," The Ohio State University, Biodynamics Laboratory, Clinical Biomechanics vol. 13, No. 3, 1998 pp. 141-152.
Rolf G. Jacob, Mark S. Redfern, Joseph M. Furman, "Optic Flow-induced Sway in Anxiety Disorders Associated with Space and Motion Discomfort," Journal of Anxiety Disorders, vol. 9, No. 5, 1995, pp. 411-425.
Jorgensen M.J., Marras W.S., "The effect of lumbar back support tension on trunk muscle activity," Clinical Biomechanics 15 (2000), pp. 292-294.
Deborah L. King and Vladimir M. Zatsiorsky, "Extracting gravity line displacement from stabilographic recordings," Gait & Posture 6 (1997), pp. 27-38.
Kraemer W.J., Volek J.S., Bush J.A., Gotshalk L.A., Wagner P.R., Gómez A.L., Zatsiorsky V.M., Duzrte M., Ratamess N.A., Mazzetti S.A., Selle B.J., "Influence of compression hosiery on physiological responses to standing fatigue in women," The Human Performance Laboratory, Medical & Science in Sports & Exercise, 2000, pp. 1849-1858.
Papa E. and Cappozzo A., "A telescopic inverted-pendulum model of the musculo-skeletal system and its use for the analysis of the sit-to-stand motor task," Journal of Biomechanics 32 (1999), pp. 1205-1212.
Balance System, BalanceTrak 500, & Quantrem, ZapConnect.com: Medical Device Industry Portal, http://www.zapconnect.com/products/index/cfm/fuseaction/products, 2 pages. (Retrieved Apr. 5, 2011).
Bertec: Dominate Your Field, Physician's Quick Guide, Version 1.0.0, Feb. 2010, 13 pages.
Bertec: Dominate Your Field, Balancecheck Screener, Version 1.0.0, Feb. 2010, 35 pages.
Bertec: Dominate Your Field, Balancecheck Trainer, Version 1.0.0, Feb. 2010, 37 pages.
Bertec Corporation—Balancecheck Standard Screener Package, http://bertec.com/products/balance-systems/standard-screener.html, 1 page. (Retrieved Apr. 12, 2011).
Bertec Corporation—Balance Systems: Balancecheck Advanced balance assessment & training products for the balance professional, http://bertec.com/products/balance-systems.html, 1 page. (Retrieved Mar. 31, 2011).
Bertec Corporation—Balancecheck Mobile Screener Package: Portable balance screening with full functionality, http://bertec.com/products/balance-systems/mobile-screener.html, 1 page. (Retrieved Mar. 31, 2011).
Bertec Corporation—Balancecheck Standard Screener & Trainer Package: Advanced balance screening and rehabilitation system, http://bertec.com/products/balance-systems/standard-screener-trainer.html, 1 page. (Retrieved Mar. 31, 2011).
U.S. Trademark Application No. 75/136,330 filed Jul. 19, 1996, 47 pages.
Bertec: Dominate Your Field, Digital Acquire 4, Version 4.0.10, Mar. 2011, 22 pages.
Bertec: Dominate Your Field, Bertec Force Plates, Version 1.0.0, Sep. 2009, 31 pages.
U.S. Trademark Application No. 73/542,230 filed Jun. 10, 1985, 52 pages.
Brent L. Arnold and Randy J. Schmitz, "Examination of Balance Measures Produced by the Biodex Stability System," Journal of Athletic Training, vol. 33(4), 1998, pp. 323-327.
Trademark Registration No. 1,974,115 filed Mar. 28, 1994, 8 pages.
U.S. Trademark Application No. 75/471,542 filed Apr. 16, 1998, 102 pages.
VTI Force Platform, Zapconnect.com: Medical Device Industry Portal, http://zapconnect.com/products/index.cfm/fuseaction/products, 2 pages. (Retrieved Apr. 5, 2011).
Amin M., Girardi M., Konrad H.R., Hughes L., "A Comparison of Electronystagmorgraphy Results with Posturography Findings from the BalanceTrak 500," Otology Neurotology, 23(4), 2002, pp. 488-493.
Girardi M., Konrad H.R., Amin M., Hughes L.F., "Predicting Fall Risks in an Elderly Population: Computer Dynamic Posturography Versus Electronystagmography Test Results," Laryngoscope, 111(9), 2001, 1528-32.
Dr. Guido Pagnacco, Publications, 1997-2008, 3 pages.
College of Engineering and Applied Science: Electrical and Computer Engineering, University of Wyoming, Faculty: Guido Pagnacco, http://wwweng.uwyo.edu/electrical/faculty/Pagnacco.html, 2 pages. (Retrieved Apr. 20, 2011).
EyeTracker, IDEAS, DIFRA, 501(k) Summary: premarket notification, Jul. 5, 2007, 7 pages.
Vestibular technologies, copyright 2000-2004, 1 page.
Scopus preview—Scopus—Author details (Pagnacco, Guido), http:www.scopus.com/authid/detail.url?authorId=6603709393, 2 pages. (Retrieved Apr. 20, 2011).
Vestibular Technologies Company Page, "Vestibular technologies: Helping People Regain their Balance for Life," http:www.vestibtech.com/AboutUs.html, 2 pages. (Retrieved Apr. 20, 2011).
GN Otometrics Launces ICS Balance Platform: Portable system for measuring postural sway, http://audiologyonline.com/news/pf_news_detail.asp?news_id=3196, 1 page. (Retrieved Mar. 31, 2011).
U.S. Trademark Application No. 75/508,272 filed Jun. 25, 1998, 36 pages.
U.S. Trademark Application No. 75/756,991 filed Jul. 21, 1999, 9 pages.
U.S. Trademark Application No. 76/148,037 filed Oct. 17, 2000, 78 pages.
Vestibular technologies, VTI Products: BalanceTRAK User's Guide, Preliminary Version 0.1, 2005, 34 pages.
U.S. Trademark Application 76/148,037 filed Oct. 17, 2000, 57 pages.

(56) References Cited

OTHER PUBLICATIONS

Vestibular Technologies, Waybackmachine, http://vestibtech.com/balancetrak500.html, 7 pages. (Retrieved Mar. 30, 2011).
Vestibular Technologies, 2004 Catalog, 32 pages.
State of Delaware: The Official Website of the First State, Division of Corporations—Online Services, http://delecorp.delaware.gov/tin/controller, 2 pages. (Retrieved Mar. 21, 2011).
Memorandum in Support of Plaintiff IA Labs' Motion for Partial Summary Judgment on Defendants' Affirmative Defense and Counterclaim That U.S. Patent No. 7,121,982 is Invalid Under 35 U.S.C. §§ 102 and 103, *IA Labs CA, LLC*, (Plaintiff) v. *Nintendo Co., Ltd. et al.*, (Defendant), United States District Court for the District of Maryland Southern Division (Apr. 27, 2011), 17 pages.
Interface, Inc.—Advanced Force Measurement—SM Calibration Certificate Installation Information, 1984.
Hugh Stewart, "Isometric Joystick: A Study of Control by Adolescents and Young Adults with Cerebral Palsy," The Australian Occupational Therapy Journal, Mar. 1992, vol. 39, No. 1, pp. 33-39.
Raghavendra S. Rao, et al., "Evaluation of an Isometric and a Position Joystick in a Target Acquisition Task for Individuals with Cerebral Palsy," IEEE Transactions on Rehabilitation Engineering, vol. 8, No. 1, Mar. 2000, pp. 118-125.
D. Sengupta, et al., "Comparative Evaluation of Control Surfaces for Disabled Patients,"Proceedings of the 27th Annual Conference on Engineering in Medicine and Biology, vol. 16, Oct. 6-10, 1974, p. 356.
Ludonauts, "Body Movin'," May 24, 2004, http://web.archive.org/web/20040611131903/http:/www.ludonauts.com; retrieved Aug. 31, 2010, 4 pages.
Atari Gaming Headquarters—AGH's Atari Project Puffer Page, http://www.atarihq.com/othersec/puffer/index.html, retrieved Sep. 19, 2002, 4 pages.
Michael Antonoff, "Real estate is cheap here, but the places you'd most want to visit are still under construction," Popular Science, Jun. 1993, pp. 33-34.
Steve Aukstakalnis and David Blatner, "The Art and Science of Virtual Reality—Silicon Mirage," 1992, pp. 197-207.
Electronics, edited by Michael Antonoff, "Video Games—Virtual Violence: Boxing Without Bruises," Popular Science, Apr. 1993, p. 60.
Stuart F. Brown, "Video cycle race," Popular Science, May 1989, p. 73.
Scanning the Field for Ideas, "Chair puts Player on the Joystick," Machine Design, No. 21, Oct. 24, 1991, XP000255214, 1 page.
Francis Hamit, "Virtual Reality and the Exploration of Cyberspace," University of MD Baltimore County, 1993, 4 pages.
Innovation in Action—Biofeed back Motor Control, Active Leg Press—IsoLegPress, 2 pages (date unknown).
Ric Manning, "Videogame players get a workout with the Exertainment," The Gizmo Page from the Courier Journal Sep. 25, 1994, 1 page.
Tech Lines, Military—Arcade aces and Aviation—Winging it, Popular Mechanics, Mar. 1982, p. 163.
Sarju Shah, "Mad Catz Universal MC2 Racing Wheel: Mad Catz MC2 Universal," Game Spot, posted Feb. 18, 2005, 3 pages.
Joe Skorupa, "Virtual Fitness," Sports Science, Popular Mechanics, Oct. 1994, 3 pages.
Nintendo Zone—The History of Nintendo (1889-1997), retrieved Aug. 24, 1998 pp. 1, 9-10.
The Legible City, Computergraphic Installation with Dirk Groeneveld, Manhattan version (1989), Amsterdam version (1990), Karlsruhe version (1991), 3 pages.
The New Exertainment System. It's All About Giving Your Members Personal Choices, Life Fitness, Circle Reader Service Card No. 28, 1995, 1 page.
The Race Begins with $85, Randal Windracer, Circle Reader Service Card No. 34, 1990, 1 page.
Universal S-Video/Audio Cable; Product #5015, MSRP 9.99; http://www.madcatz.com/Default.asp?Page=133 &CategoryImg=Universal_Cables, retrieved May 12, 2005, 1 page.

Tom Dang, et al., "Interactive Video Exercise System for Pediatric Brain Injury Rehabilitation," Assistive Technology Research Center, Rehabilitation Engineering Service, National Rehabilitation Hospital, Proceedings of the RESNA 20th Annual Conference, Jun. 1998, 3 pages.
Raymond W. McGorry, "A system for the measurement of grip forces and applied moments during hand tool use," Liberty Mutual Research Center for Safety and Health, Applied Ergonomics 32 (2001) 271-279.
NordicTrack's Aerobic Cross Trainer advertisement as shown in "Big Ideas—For a Little Money: Great Places to Invest $1,000 or Less," Kiplinger's Personal Finance Magazine, Jul. 1994, 3 pages.
Maurice R. Masliah, "Measuring the Allocation of Control in 6 Degree of Freedom Human-Computer Interaction Tasks," Graduate Department of Mechanical and Industrial Engineering, University of Toronto, 2001, 177 pages.
Leigh Ann Roman, "Boing! Combines Arcade Fun with Physical Training," Memphis—Health Care News: Monitoring the Pulse of Our Health Care Community, Sep. 20, 1996, One Section, 1 page.
"No More Couch Potato Kids," as shown in Orange Coast, Sep. 1994, p. 16.
Gary L. Downey, et al., "Design of an Exercise Arcade for Children with Disabilities," Resna, Jun. 26-30, 1998, pp. 405-407.
Frank Serpas, et al., "Forward-dynamics Simulation of Anterior Cruciate Ligament Forces Developed During Isokinetic Dynamometry," Computer Methods in Biomechanics and Biomedical Engineering, vol. 5 (1), 2002, pp. 33-43.
Carolyn Cosmos, "An 'Out of Wheelchair Experience'", The Washington Post, May 2, 2000, 3 pages.
David H. Ahl, "Controller update," Creative Computing, vol. 9, No. 12, Dec. 1983, p. 142.
Ian Bogost, "Water Cooler Games—The Prehistory of Wii Fit," Videogame Theory, Criticism, Design, Jul. 15, 2007, 2 pages.
Jeremy Reimer, "A history of the Amiga, part 2: The birth of Amiga," last updated Aug. 12, 2007, 2 pages.
The Amiga Joyboard (1982) image, Photos: Fun with plastic—peripherals that changed gaming; http://news.cnet.com/2300-27076_3-10001507-2.html (retrieved Jul. 23, 2010), 1 page.
The Amiga Power System Joyboard, Amiga history guide, http://www.amigahistory.co.uk/joyboard.html (retrieved Jul. 23, 2010), 2 pages.
"Joyboard," Wikipedia—the free encyclopedia, http://en.wikipedia.org/wiki/Joyboard (retrieved Jul. 26, 2010), 2 pages.
"Dance Dance Revolution," Wikipedia—the free encyclopedia, http://en.wikipedia.org/wiki/Dance Dance Revolution (retrieved Jul. 23, 2010), 9 pages.
"Cure for the couch potato," Kansas City Star (MO), Jan. 2, 2005, WLNR 22811884, 1 page.
JC Fletcher, "Virtually Overlooked: The Power Pad games," Joystiq, http://www.joystiq.com/2007/09/20/virtually-overlooked-the-power-pad-games/ (retrieved Jul. 26, 2010), 3 pages.
Family Fun Fitness, Nintendo Entertainment System, BANDAI, (date unknown).
"Power Pad/Family Fun and Fitness/Family Trainer," http://www.gamersgraveyard.com/repository/nes/peripherals/powerpad.html (retrieved Jul. 26, 2010), 2 pages.
"Power Pad Information," Version 1.0 (Sep. 23, 1999) http://www.gamersgraveyard.com/repository/nes/peripherals/powerpad.txt (retrieved Jul. 26, 2010), 2 pages.
Wii+Power+Pad.jpg (image), http://bpl.blogger.com/_J5LEiGp54I/RpZbNpnLDgl/AAAAAAAAAic/Gum6DD3Umjg/s1600-h/Wii+Power+Pad.jpg (retrieved Jul. 26, 2010), 1 page.
Vs. Slalom—Videogame by Nintendo, KLOV—Killer List of Video Games, http://www.arcade-museum.com/game_detail.php?game_id=10368 (retrieved Jul. 26, 2010), 3 pages.
"Nintendo Vs. System," Wikipedia—the free encyclopedia, http://en.wikipedia.org/wiki/Nintendo_Vs._System (retrieved Jul. 26, 2010), 3 pages.
Family Fun Fitness: Basic Set (Control Mat and Athletic World Game Pak), Nintendo Entertainment System, Bandai, (date unknown).
Roll & Rocker, Enteractive (image), 2 pages, (date unknown).

(56) References Cited

OTHER PUBLICATIONS

Candace Putnam, "Software for Hardbodies: A virtual-reality hike machine takes you out on the open road," Design, 1 page, (date unknown).

"Top Skater," Sega Amusements U.S.A, Inc, 1 page, (date unknown).

Nintendo Co., Ltd. and Nintendo of America Inc.'s Opening Claim Construction Brief, *IA Labs CA, LLC* v. *Nintendo Co., Ltd. and Nintendo of America, Inc.*, United States District Court for the District of Maryland Southern Division (Dec. 13, 2010), 55 pages.

Plaintiff IA Labs CA, LLC's Response Claim Construction Brief, *IA Labs CA, LLC* v. *Nintendo Co., Ltd.* and *Nintendo of America, Inc.*, United States District Court for the District of Maryland Southern Division (Jan. 6, 2011), 49 pages.

Nintendo Co., Ltd. and Nintendo of America Inc.'s Closing Claim Construction Brief, *IA Labs CA, LLC* v. *Nintendo Co., Ltd. and Nintendo of America, Inc.*, United States District Court for the District of Maryland Southern Division (Jan. 6, 2011), 25 pages.

Expert Report of Lee Rawls, Nov. 2, 2010, 37 pages (redacted).

Addlesee, M.D., et al., "The ORL Active Floor," IEEE—Personal Communications, Oct. 1997.

Baek, Seongmin, et al., "Motion Evaluation for VR-based Motion Training," Eurographics 2001, vol. 20, No. 3, 2001.

Biodex Medical Systems, Inc.—Balance System SD Product Information—http://www.biodex.com/rehab/balance/balance_300feat.htm.

Chen, I-Chun, et al., "Effects of Balance Training on Hemiplegic Stroke Patients," Chang Gung Medical Journal, vol. 25, No. 9, pp. 583-590, Sep. 2002.

Dingwell, Jonathan, et al., "A Rehabilitation Treadmill with Software for Providing Real-Time Gait Analysis and Visual Feedback," Transactions of the ASME, Journal of Biomechanical Engineering, 118 (2), pp. 253-255, 1996.

Geiger, Ruth Ann, et al., "Balance and Mobility Following Stroke: Effects of Physical Therapy Interventions With and Without Biofeedback/Forceplate Training," Physical Therapy, vol. 81, No. 4, pp. 995-1005, Apr. 2001.

Harikae, Miho, "Visualization of Common People's Behavior in the Barrier Free Environment," Graduate Thesis—Master of Computer Science and Engineering in the Graduate School of the University of Aizu, Mar. 1999.

Hodgins, J.K., "Three-Dimensional Human Running," Proceedings: 1996 IEEE International Conference on Robotics and Automation, vol. 4, Apr. 1996.

Kim, Jong Yun, et al., "Abstract—A New VR Bike System for Balance Rehabilitation Training," Proceedings: 2001 IEEE Seventh International Conference on Virtual Systems and Multimedia, Oct. 2001.

McComas, Joan, et al., "Virtual Reality Applications for Prevention, Disability Awareness, and Physical Therapy Rehabilitation in Neurology: Our Recent Work," School of Rehabilitation Sciences, University of Ottawa—Neurology Report, vol. 26, No. 2, pp. 55-61, 2002.

Nicholas, Deborah S, "Balance Retraining After Stroke Using Force Platform Feedback," Physical Therapy, vol. 77, No. 5, pp. 553-558, May 1997.

Redfern, Mark, et al., "Visual Influences of Balance," Journal of Anxiety Disorders, vol. 15, pp. 81-94, 2001.

Sackley, Catherine, "Single Blind Randomized Controlled Trial of Visual Feedback After Stroke: Effects on Stance Symmetry and Function," Disavility and Rehabilitation, vol. 19, No. 12, pp. 536-546, 1997.

Tossavainen, Timo, et al., "Postural Control as Assessed with Virtual Reality," Acta Otolaryngol, Suppl 545, pp. 53-56, 2001.

Tossavainen, Timo, et al., "Towards Virtual Reality Simulation in Force Platform Posturography," MEDINFO, pp. 854-857, 2001.

Tsutsuguchi, Ken, et al., "Human Walking Animation Based on Foot Reaction Force in the Three-Dimensional Virtual World," The Journal of Visualization and Computer Animation, vol. 11, pp. 3-16, 2000.

Wong, Alice, et al., "The Development and Clinical Evaluation of a Standing Biofeedback Trainer," Journal of Rehabilitation Research and Development, vol. 34, No. 3, pp. 322-327, Jul. 1997.

Yang, Ungyeon, et al., "Implementation and Evaluation of 'Just Follow Me': An Immersive, VR-Based, Motion-Training System," Presence, vol. 11, No. 3, pp. 304-323, 2002.

Search Report (2 pgs.) dated May 27, 2011 issued in German Application No. 20 2004 021 793.7.

\* cited by examiner

F I G. 2 2
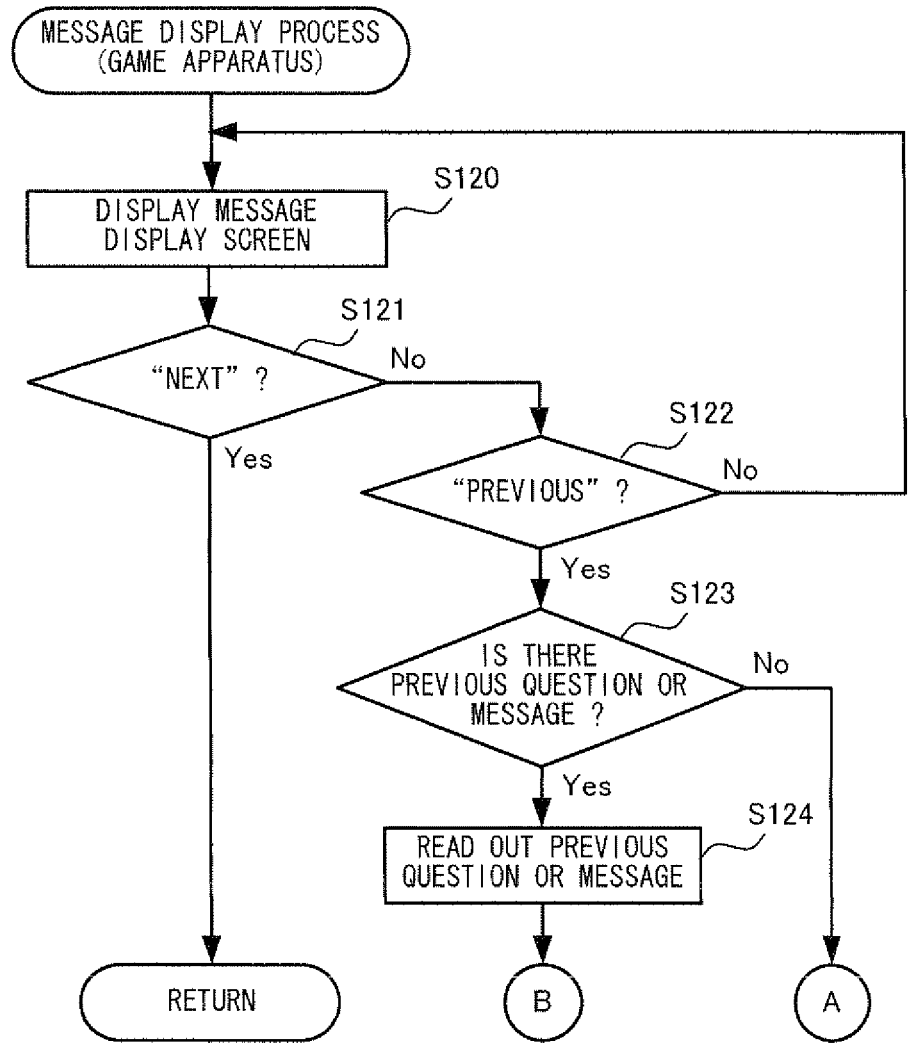

BIOLOGICAL INFORMATION MANAGEMENT SYSTEM

CROSS REFERENCE TO RELATED APPLICATION

The disclosure of Japanese Patent Application No. 2008-334795, filed on Dec. 26, 2008, is incorporated herein by reference.

BACKGROUND OF THE INVENTION

1. Field of the Invention

The present invention relates to a biological information management system, and in particular, to a biological information management system including a first information processing apparatus and a second information processing apparatus capable of communicating with the first information processing apparatus.

2. Description of the Background Art

Conventionally, there is a system that transmits biological information, obtained by an apparatus, to another apparatus. For example, Japanese Patent Laid-open Publication No. 2004-118339 discloses a system in which a pedometer counts the number of steps taken, a mobile phone is connected to the pedometer to obtain step count data, and the step count data is transmitted from the mobile phone to a server through the Internet. Further, Japanese Patent Laid-open Publication No. H11-151211 discloses a system in which a terminal apparatus obtains data of bloodpressures, body temperatures, and weights, which are measured by health measuring instruments, and transmits the data to a center apparatus through a public line.

However, the system disclosed in Japanese Patent Laid-open Publication No. 2004-118339 has a problem that it is difficult to accurately determine the condition of a user because any message created by the user is not transmitted to the server together with the obtained step count data.

Further, in the system disclosed in Japanese Patent Laid-open Publication No. H11-151211, the measured data transmitted to the terminal apparatus is transmitted to the center apparatus with automatic dialing once a day, and if the communication fails, the transmission process is repeated until the communication succeeds. However, the measured data cannot be transmitted at a timing desired by a user, and any message created by the user cannot be transmitted together with the measured data. Thus, it is impossible to accurately determine the condition of the user.

SUMMARY OF THE INVENTION

Therefore, an object of the present invention is to provide a biological information management system capable of transmitting biological information together with a message.

The present invention has the following features to attain the object mentioned above. It is noted that reference characters and the like in parentheses are merely provided to facilitate the understanding of the present invention in relation to the drawings, rather than limiting the scope of the present invention in any way.

A biological information management system of the present invention comprises a first information processing apparatus (12) and a second information processing apparatus (90) capable of communicating with the first information processing apparatus.

The first information processing apparatus includes: biological information obtaining means (40, S82) for obtaining biological information; first message creation means (40, S70 to S79) for creating a first message based on an input operation of an operator of the first information processing apparatus; and first message transmission means (40, S84) for transmitting the biological information obtained by the biological information obtaining means and the first message created by the first message creation means to the second information processing apparatus, The second information processing apparatus includes: first message reception means (S141) for receiving the biological information and the first message from the first information processing apparatus; and storage means (S142) for storing the biological information and the first message which are received by the first message reception means.

Thus, it is possible for an operator of the second information processing apparatus to know the condition of the operator of the first information processing apparatus because the biological information of the operator can be transmitted together with the message created by the operator of the first information processing apparatus.

Here, the "biological information" may include information regarding a body, such as weight, body fat percentage, and the like; information regarding exercise, such as the number of steps taken, exercise time, and the like; and information regarding vital signs, such as blood pressure, body temperature, heart rate, and the like.

Further, the "first information processing apparatus" and the "second information processing apparatus" may be arbitrary information processing apparatuses, and, for example, may be stationary game apparatuses, hand-held game apparatuses, mobile phones, personal computers, PDAs, and the like.

Further, the "first message" is not limited to a message including only characters, but may be a message including choices, or a message including a character input section or a numeric input section.

Upon receiving a transmission instruction of the first message from the operator of the first information processing apparatus, the first message transmission means may automatically obtain the biological information by the biological information obtaining means and may transmit the obtained biological information together with the first message to the second information processing apparatus.

Thus, when the operator of the first information processing apparatus transmits the message, inputting of the biological information is omitted, and the biological information is assuredly transmitted.

The biological information management system may further comprise a biological information measuring apparatus (36, 92) including: biological information measuring means (36b) for measuring biological information; and biological information transmission means (106) for transmitting the biological information measured by the biological information measuring means to the first information processing apparatus, and the biological information obtaining means may include biological information reception means (50) for receiving the biological information from the biological information measuring apparatus.

Thus, the operator of the first information processing apparatus can carry only the biological information measuring means to a desired place where biological information is to be measured.

Here, the "biological information measuring means" may include a weighing apparatus, a pedometer, a blood-pressure gauge, a clinical thermometer, and the like.

Further, the communication between the "first information processing apparatus" and the "biological information measuring means" may be wire or wireless communication. Further, its communication method is arbitrary. For example, it may be the Bluetooth (registered trademark), infrared communication, or another wireless communication method. Further, the communication may be performed through a public communication line such as the Internet and the like, or through a local network. Further, the communication may be performed not through a communication cable.

Further, the biological information obtaining means may include biological information measuring means for measuring biological information.

Thus, it is easy to obtain the biological information because the first information processing apparatus includes the biological information measuring means.

Further, the biological information measuring means may measure a weight, or counts the number of steps taken, as the biological information.

Further, the first information processing apparatus may also include process means (40, S21) for executing a process using the biological information measuring means, and process time counting means (40, S22) for counting a time of the process executed by the processing means; and the biological information obtaining means may also obtain the time counted by the process time counting means.

Thus, the time, for which the operator of the first information processing apparatus uses the biological information measuring means, can be transmitted as the biological information to the second information processing apparatus.

Further, the first information processing apparatus may also include storage means (40) for storing the biological information obtained by the biological information obtaining means and measurement date information of the biological information, and the first message transmission means may refer to the measurement date information and may transmit biological information of a predetermined period.

Thus, it is possible for the operator of the second information processing apparatus to have knowledge of the transition of the biological information, of the operator of the first information processing apparatus, for the predetermined period.

Further, the first message transmission means may transmit the biological information and the first message as one file to the second information processing apparatus.

Thus, it becomes easy to manage data at the second information processing apparatus.

Further, the second information processing apparatus may also include: second message creation means (S30 to S38) for creating a second message based on an input operation of an operation of the second information processing apparatus; and second message transmission means (S41) for transmitting the second message created by the second message creation means to the first information processing apparatus, the first information processing apparatus may also include second message reception means (50) for receiving the second message from the second information processing apparatus, and the first message creation means may create the first message based on the second message received by the second message reception means.

Thus, it becomes possible to exchange detailed information between the operator of the first information processing apparatus and the operator of the second information processing apparatus because the first information processing apparatus creates the first message based on the second message transmitted from the second information processing apparatus, and transmits the first message together with the biological information to the second information processing apparatus.

The "second message" is not limited to a message including only characters, but may be a message including choices, or a message including a character input section or a numeric input section.

Further, the second message may be a question message, the first information processing apparatus may also include question execution means (40, S90, S100, S110) for executing a question based on the question message received by the second message reception means, and the first message creation means may create, as the first message, an answer message to the question executed by the question execution means.

Thus, it becomes possible to exchange on-target information between the operator of the first information processing apparatus and the operator of the second information processing apparatus because the first information processing apparatus creates the answer message to the question message transmitted from the second information processing apparatus, and transmits the answer message to the second information processing apparatus.

A computer-readable storage medium (44) of the present invention stores a computer program (AP1) for a biological information management system comprising a first information processing apparatus (12) and a second information processing apparatus (90) capable of communicating with the first information processing apparatus.

The computer program causes a computer (40) of the first information processing apparatus to function as: biological information obtaining means (S82) for obtaining biological information; first message creation means (S70 to S79) for creating a first message based on an input operation of an operator of the first information processing apparatus; and first message transmission means (S84) for transmitting the biological information obtained by the biological information obtaining means and the first message created by the first message creation means to the second information processing apparatus.

An information processing apparatus of the present invention is used as a first information processing apparatus (12) in a biological information management system comprising the first information processing apparatus and a second information processing apparatus (90) capable of communicating with the first information processing apparatus. The information processing apparatus comprises: biological information obtaining means (40, S82) for obtaining biological information; first message creation means (40, S70 to S79) for creating a first message based on an input operation of an operator of the first information processing apparatus; and first message transmission means (40, S84) for transmitting the biological information obtained by the biological information obtaining means and the first message created by the first message creation means to the second information processing apparatus.

A health guidance support system of the present invention is a health guidance support system for a healthcare professional to perform health guidance for a healthcare recipient. The health guidance support system comprises: a healthcare professional terminal (90) operated by the healthcare professional; and a healthcare recipient terminal (12) operated by the healthcare recipient and capable of communicating with the healthcare professional terminal.

The healthcare professional terminal includes: question message creation means (S30 to S38) for creating a question message in accordance with an input operation of the healthcare professional; and question message transmission means (S41) for transmitting the question message from the healthcare professional terminal to the healthcare recipient terminal.

the healthcare recipient terminal includes: question message reception means (50) for receiving the question message from the healthcare professional terminal; question message displaying means (40, 34, S90, S100, S110) for displaying the received question message to the healthcare recipient; answer message creation means (40, S70 to S79) for creating an answer message to the question message in accordance with an input operation of the healthcare recipient; and answer message transmission means (40, S84) for, upon receiving a transmission instruction from the healthcare recipient, automatically obtaining biological information (weight data, exercise time data, step count data) regarding health of the healthcare recipient from a storage unit (44) that is provided in or connected to the healthcare recipient terminal, and transmitting the biological information together with the created answer message to the healthcare professional terminal.

The healthcare professional terminal further includes: answer message reception means (S141) for receiving the answer message together with the biological information from the healthcare recipient terminal; and answer message displaying means (S145) for displaying the received answer message and the biological information to the healthcare professional.

Thus, when the healthcare recipient transmits the answer message, inputting of the biological information is omitted, and the biological information is assuredly transmitted. In addition, because the healthcare professional can fully confirm the biological information required for health guidance, the healthcare professional can properly and efficiently perform health guidance.

The healthcare recipient terminal may be a game apparatus; and the answer message transmission means may obtain the biological information regarding the health of the healthcare recipient from saved data (D2, D3) of a game executed previously in the healthcare recipient terminal.

Thus, the game apparatus can be used for health guidance, and the user of the game apparatus can readily take health guidance. In addition, because the biological information is obtained from the saved data of the game executed previously in the game apparatus, inputting of the biological information by the user is omitted.

According to the present invention, a biological information management system capable of transmitting biological information together with a message can be provided.

These and other objects, features, aspects and advantages of the present invention will become more apparent from the following detailed description of the present invention when taken in conjunction with the accompanying drawings.

BRIEF DESCRIPTION OF THE DRAWINGS

FIG. 22 is a flow chart showing a procedure of a message display process executed by the game apparatus;

DESCRIPTION OF THE PREFERRED EMBODIMENTS

The following will describe an embodiment of the present invention with reference to the drawings.

(Game System)

Figure 1:
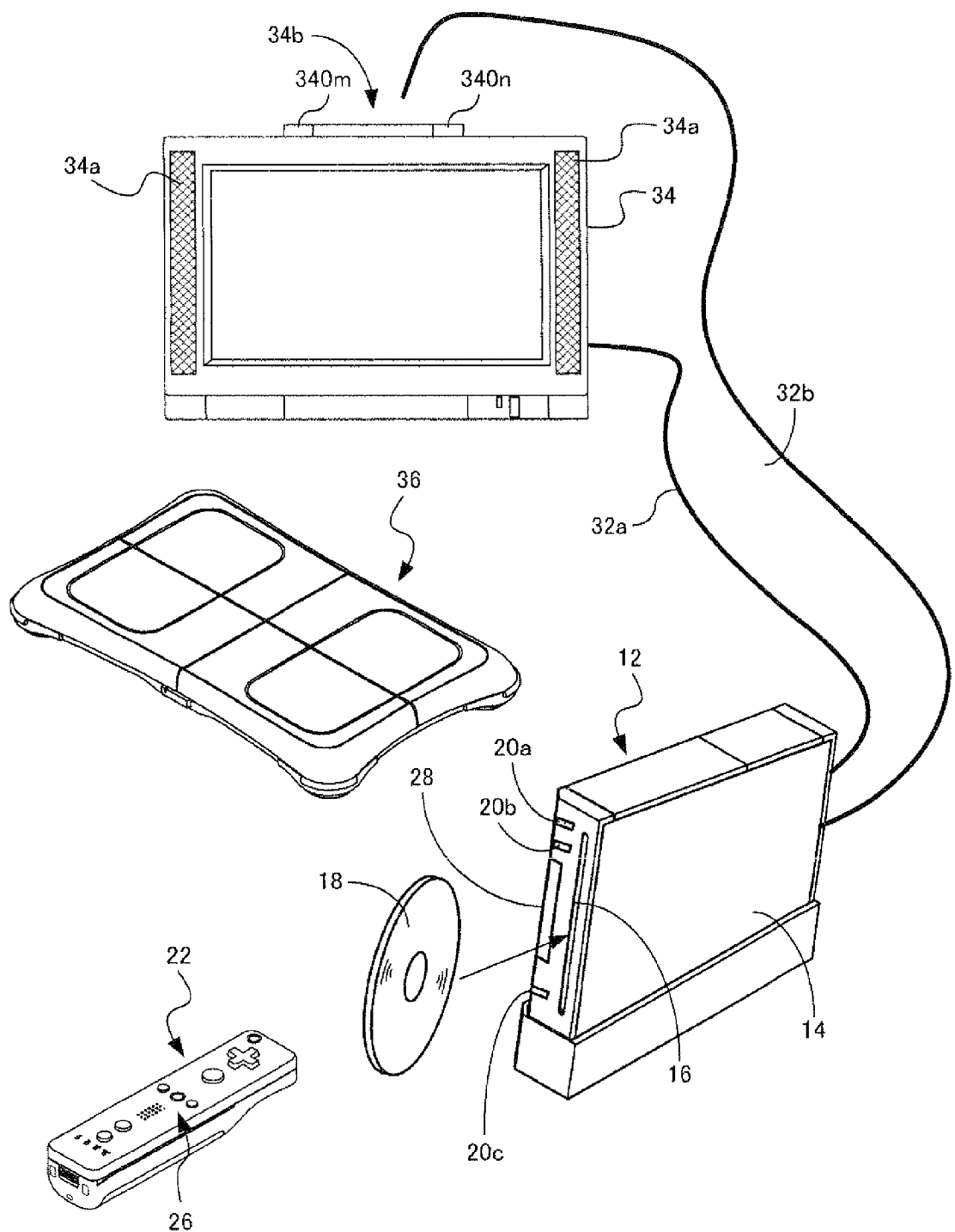
FIG. 1 is a view showing a game system according to one embodiment of the present invention.

First, a game system used in the present embodiment will be described. As shown in FIG. 1, a game system 10 includes a video game apparatus (hereinafter, referred to merely as "game apparatus") 12, a controller 22, and a load controller 36. Although not shown in the drawings, the game apparatus 12 of the present embodiment is designed so as to be capable of communicating with four controllers (22, 36). The game apparatus 12 is connected to each controller (22, 36) wirelessly. For example, the wireless communication is performed in accordance with the Bluetooth standard, but may be performed in accordance with another standard of infrared communication, a wireless LAN, or the like.

The game apparatus 12 includes a parallelepiped-shaped housing 14 provided with a disc slot 16 on a front surface thereof. Through the disc slot 16, an optical disc 18, which is an example of an information storage medium storing a game program and the like, is inserted, and mounted to a disc drive 54 (see FIG. 2) in the housing 14. Around the disc slot 16, an LED and a light guide plate are arranged, and the LED is capable of being lit in response to various processes.

Further, on an upper portion of the front surface of the housing 14 of the game apparatus 12, a power button 20a and a reset button 20b are provided, and on a lower portion thereof, an eject button 20c is provided. In addition, an external memory card connector cover 28 is provided between the reset button 20b and the eject button 20c and adjacent to the disc slot 16. Inside the external memory card connector cover 28, an external memory card connector 62 (see FIG. 2) is provided, and an external memory card (not shown; hereinafter, referred to merely as "memory card") is inserted into the external memory card connector 62. The memory card is used for loading and temporally storing the game program and the like read out from the optical disc 18, and for storing (saving) game data (result data or midstream data of a game) of the game played using the game system 10. However, the game data may be stored in an internal memory such as a flash memory 44 (see FIG. 2) provided in the game apparatus 12, instead of the memory card. Further, the memory card may be used as a backup memory for the internal memory.

As the memory card, a general-purpose SD card can be used, but other general-purpose memory cards such as a memory stick and a Multi-Media Card (registered trademark) can be used.

On a rear surface of the housing 14 of the game apparatus 12, an AV connector 58 (see FIG. 2) is provided, and a monitor 34 and speakers 34a are connected to the game apparatus 12 through an AV cable 32a by means of the AV connector 58. The monitor 34 and the speakers 34a typically constitute a color television receiver, and a video signal and an audio signal from the game apparatus 12 are inputted to a video input terminal and an audio input terminal, respectively, of the color television receiver through the AV cable 32a. Thus, a game image of a three-dimensional (3D) video game is displayed on the screen of the color television receiver (monitor) 34, and stereo game sound such as game music, effect sound, and the like is outputted from both speakers 34a. Further, a marker section 34b including infrared LEDs (markers) 340m and 340n is provided adjacent to the monitor 34 (on the upper side of the monitor 34 in the present embodiment). The marker section 34b is connected to the game apparatus 12 through a power cable 32b. Thus, electric power is supplied from the game apparatus 12 to the marker section 34b. Whereby, the markers 340m and 340n emit infrared light forward from the monitor 34.

The electric power is supplied to the game apparatus 12 through a general AC adapter (not shown). The AC adapter is inserted into a household standard wall socket, and the game apparatus 12 converts household power (commercial power) into a low DC-voltage signal that is suitable for driving the game apparatus 12. In an alternative embodiment, a battery may be used as a power source.

In the game system 10, in order for a user or a player to play a game (it is not limited thereto, and may be another application), the user turns on the game apparatus 12, and then selects an appropriate optical disc 18 storing the video game (or the other application that the user desires to play), and the optical disc 18 is loaded onto the disc drive 54 of the game apparatus 12. Accordingly, the game apparatus 12 starts to execute the video game or the other application based on a program stored in the optical disc 18. The user operates the controller 22 for performing an input to the game apparatus 12. For example, by operating any one of input means 26, the use starts the game or the other application. Further, in addition to operating the input means 26, by moving the controller 22, an image object (player object) can be moved in a different direction, or a viewpoint (camera position) of the user in a 3D game world can be changed.

Figure 2:
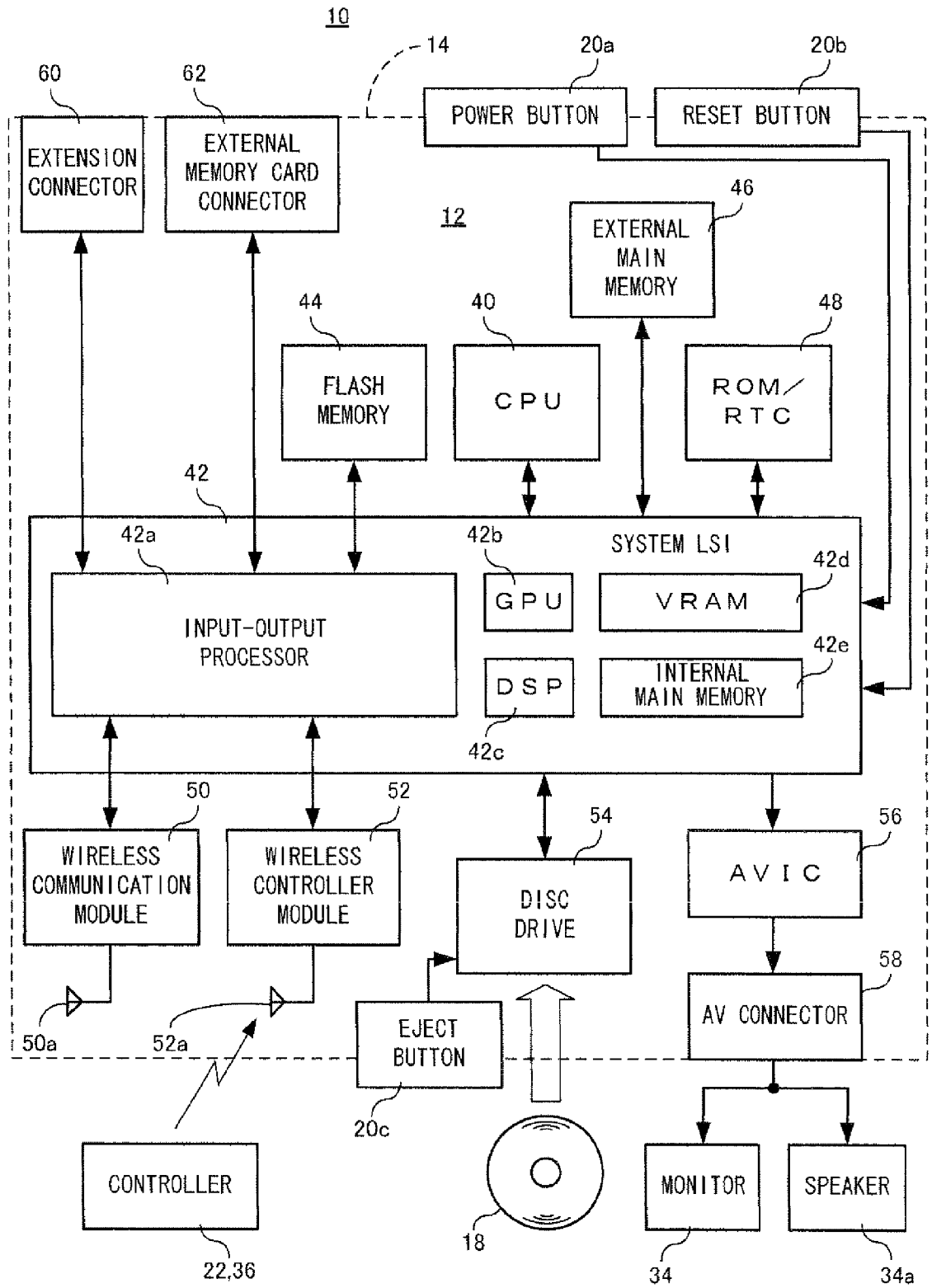
FIG. 2 is a block diagram showing an example of an electrical configuration of the game system.

FIG. 2 is a block diagram showing an electrical configuration of a game system 10 of the present embodiment in FIG. 1. Although not shown in the drawings, each component in the housing 14 is mounted on a printed circuit board. As shown in FIG. 2, the game apparatus 12 is provided with a CPU 40. The CPU 40 functions as a game processor. The CPU 40 is connected to a system LSI 42. The system LSI 42 is connected to an external main memory 46, a ROM/RTC 48, the disc drive 54, and an AVICS 56.

The external main memory 46 stores a program, such as a game program and the like, and various data, and is used as a work region and a buffer region for the CPU 40. The ROM/RTC 48 includes a ROM (so-called boot ROM) that stores a program for starting up the game apparatus 12; and a clock circuit for counting time. The disc drive 54 reads program data and texture data from the optical disc 18, and writes these data into a later-described internal main memory 42e or the external main memory 46 under the control of the CPU 40.

The system LSI 42 is provided with an input-output processor (I/O process) 42a, a GPU (Graphics Processor Unit) 42b, a DSP (Digital Signal Processor) 42c, a VRAM 42d, and the internal main memory 42e. Although not shown in the drawings, these components are connected to each other through an internal bus.

The input-output processor 42a performs transmission and reception of data to and from each component connected to the input-output processor 42a, and downloads data. The transmission and reception of data and the download of data will be described in detail later.

The GPU 42b forms a part of drawing means, receives a graphics command (command for generating graphics) from the CPU 40, and generates an image according to the graphics command. In addition to the graphics command, the CPU 40 provides the GPU 42b with an image generation program required for generating game image data.

Although not shown in the drawings, the VRAM 42d is connected to the CPU 42b as described above. Prior to executing the graphics command, the CPU 42b accesses the VRAM 42d and obtains required data (image data: data such as polygon data, texture data, and the like). The CPU 40 writes image data, required for drawing an image, into the VRAM 42d through the CPU 42b. The CPU 42b accesses the VRAM 42d and generates game image data for drawing an image.

The present embodiment describes a case where the GPU 42b generates game image data. However, in a case of executing an arbitrary application other than the game application, the GPU 42b generates image data for the arbitrary application.

Further, the DSP 42c functions as an audio processor, and generates audio data, which correspond to sound, voice, and music outputted from the speakers 34a, by using sound data and sound waveform (tone color) data which are stored in the internal main memory 42e and the external main memory 46.

The image data and the audio data generated thus are read by the AVIC 56. The AVIC 56 outputs the image data and the audio data to the monitor 34 and the speakers 34a, respectively, through the AV connector 58. Thus, a game image is displayed on the monitor 34, and sound (music) required for the game is outputted from the speakers 34a.

Further, the input-output processor 42a is connected to a flash memory 44, a wireless communication module 50, a wireless controller module 52, an extension connector 60, and the external memory card connector 62. The wireless communication module 50 is connected to an antenna 50a, and the wireless controller module 52 is connected to an antenna 52a.

The input-output processor 42a is capable of communicating with another game apparatus connected to a network and various servers connected to the network, through the wireless communication module 50. However, the input-output processor 42a is capable of communicating directly with the other game apparatus, not through the network. The input-output processor 42a periodically accesses the flash memory 44 to detect whether or not there is data (referred to as transmission data) required to be transmitted to the network. If there is the transmission data, the input-output processor 42a transmits the transmission data to the network through the wireless communication module 50 and the antenna 50a. The input-output processor 42a receives data (referred to as reception data) transmitted from the other game apparatus through the network, the antenna 50a, and the wireless communication module 50, and stores the reception data in the flash memory 44. In a predetermined case, the input-output processor 42a discards the reception data. In addition, the input-output processor 42a receives data downloaded from a download server through the network, the antenna 50a, and the wireless communication module 50, and stores the downloaded data in the flash memory 44.

Further, the input-output processor 42a receives input data transmitted from the controller 22 and the load controller 36 through the antenna 52a and the wireless controller module 52, and stores (temporarily stores) the input data in the buffer region of the internal main memory 42e or the external main memory 46. The input data in the buffer region is deleted after being used by a game process executed by the CPU 40.

In the present embodiment, as described above, the wireless controller module 52 communicates with the controller 22 and the load controller 36 in accordance with the Bluetooth standard.

For convenience's sake, the controller 22 and the load controller 36 are shown together as one unit in FIG. 2.

The input-output processor 42a is connected to the extension connector 60 and the external memory card connector 62. The extension connector 60 is a connector for an interface such as a USB and an SCSI, and enables connection of a medium such as an external storage medium and connection of a peripheral apparatus such as another controller. Further, instead of the wireless communication module 50, a wired LAN can be used by connecting a wired LAN adapter to the extension connector 60. To the external memory card connector 62, an external storage medium such as a memory card can be connected. Thus, for example, the input-output processor 42a is capable of accessing the external storage medium through the extension connector 60 or the external memory card connector 62 for storing data in the external storage medium and reading data from the external storage medium.

Although not described in detail, the game apparatus 12 (housing 14) is provided with the power button 20a, the reset button 20b, and the eject button 20c as shown in FIG. 1. The power button 20a is connected to the system LSI 42. When the power button 20a is turned on, electric power is supplied to each component of the game apparatus 12 through the AC adapter (not shown), and the system LSI 42 becomes a normal energized mode (referred to as "normal mode"). On the other hand, when the power button 20a is turned off, electric power is supplied to only some components of the game apparatus 12, and the system LSI 42 sets a mode (hereinafter, referred to as "standby mode") that minimizes power consumption. In the present embodiment, when the standby mode is set, the system LSI 42 performs an instruction to stop supplying electric power to components other than the input-output processor 42a, the flash memory 44, the external main memory 46, the ROM/RTC 48, the wireless communication module 50, and the wireless controller module 52. Thus, the standby mode is a mode in which the CPU 40 does not execute an application.

Even in the standby mode, electric power is supplied to the system LSI 42, but, a supply of electric power to the GPU 42b, the DSP 42c, and the VRAM 42d is stopped so as not to drive them, thereby reducing the power consumption.

Further, although not shown in the drawings, a fan is provided in the housing 14 of the game apparatus 12 for discharging heat of the CPU 40, the system LSI 42, and the like. In the standby mode, the fan is stopped.

When the standby mode is not desired to be used, settings are made so as not to use the standby mode, whereby a supply of electric power to all the circuit components is stopped when the power button 20a is turned off.

Further, switching between the normal mode and the standby mode can be performed by means of remote operation such as by turning on/off a power switch 26h (see FIG. 3) of the controller 22. In the case where the remote operation is not performed, in the standby mode, settings are made so as not to supply electric power to the wireless controller module 52.

The reset button 20b is also connected to the system LSI 42. When the reset button 20b is pressed, the system LSI 42 restarts a boot program of the game apparatus 12. The eject button 20c is connected to the disc drive 54. When the eject button 20c is pressed, the optical disc 18 is ejected from the disc drive 54.

(Controller)

Figure 3A:
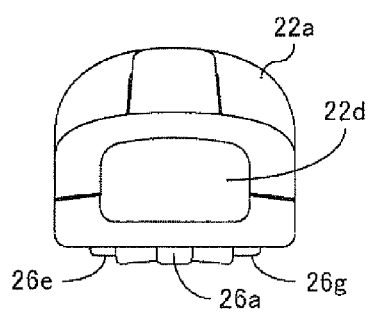
FIGS. 3A-3E are external views of a controller.
Figure 3E:
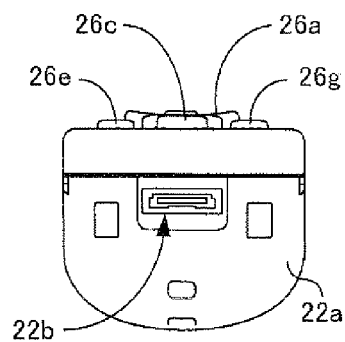
Figure 3B:
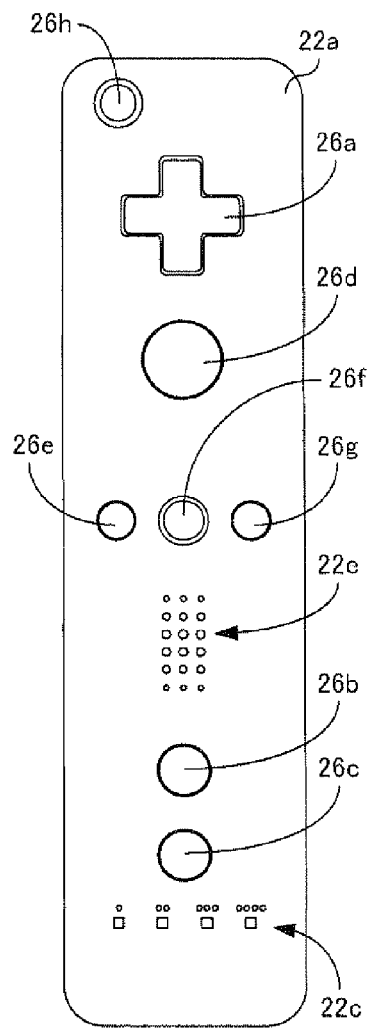
Figure 3C:
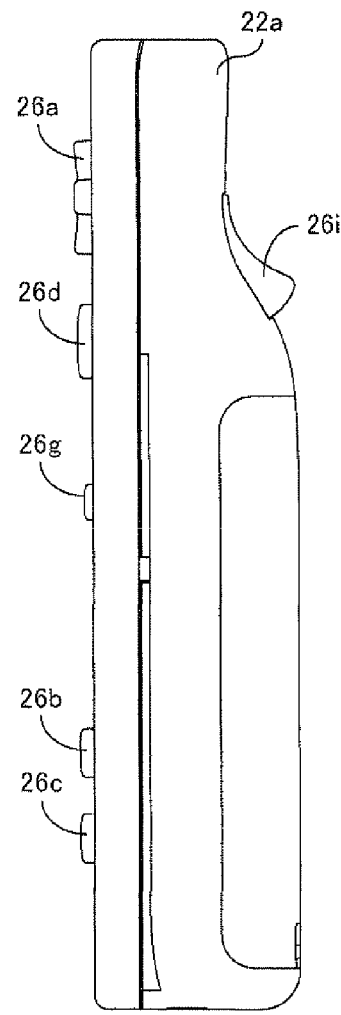
Figure 3D:
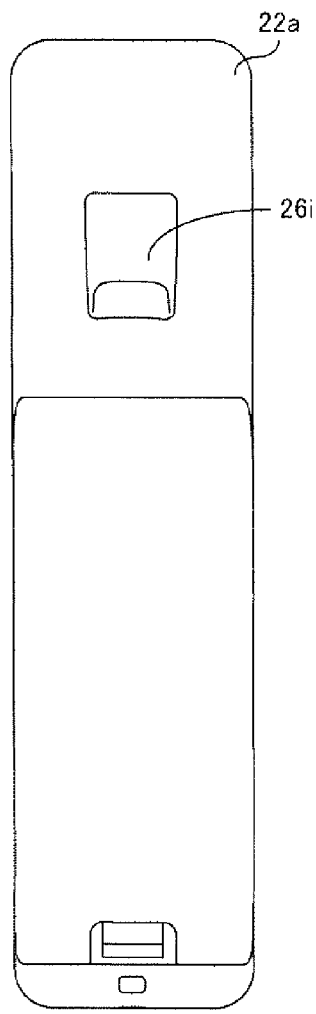

FIGS. 3(A) to 3(E) show an example of the external view of the controller 22. FIG. 3(A) shows a front surface of the controller 22, FIG. 3(B) shows a top surface of the controller 22, FIG. 3(C) shows a right side surface of the controller 22, FIG. 3(D) shows a bottom surface of the controller 22, and FIG. 3(E) shows a rear surface of the controller 22.

Referring to FIGS. 3(A) to 3(E), the controller 22 includes a housing 22a that is formed, for example, by plastic molding. The housing 22a has a generally parallelepiped shape, and its overall size is small enough to be held by one hand of the user. On the housing 22a (controller 22), the input means (a plurality of buttons and switches) 26 are provided. Specifically, as shown in FIG. 3(B), a cross key 26a, a 1 button 26b, a 2 button 26c, an A button 26d, a − button 26e, a HOME button 26f, a + button 26g, and the power switch 26h are provided on the top surface of the housing 22a. As shown in FIGS. 3(C) and 3(D), a slope surface is formed in the bottom surface of the housing 22a, and a B trigger switch 26i is provided on the slope surface.

The cross key 26a is a cross-shaped four-direction push switch, and includes operation portions corresponding to four directions, frontward (or upward), rearward (or downward), rightward, and leftward, indicated by arrows. By operating any one of the operation portions, the player can perform an instruction of a direction in which a character or an object (a player character or a player object) operable by the player moves, and can perform an instruction of a direction in which a cursor moves.

The 1 button 26b and the 2 button 26c are push-button switches. For example, the 1 button 26b and the 2 button 26c are used for game operations, such as adjustment of a viewing position and a viewing direction, namely, the viewing position and the viewing angle of a virtual camera, when displaying a three-dimensional game image, and the like. Or, the 1 button 26b and the 2 button 26c may be used when the same operation as the A button 26d and the B trigger switch 26i is performed or an auxiliary operation is performed.

The A button 26d is a push-button switch, and is used for performing an instruction, other than a direction instruction, causing the player character or the player object to perform a motion, namely, an arbitrary action such as hitting (punching), throwing, grabbing (obtaining), riding, jumping, and the like. For example, in an action game, an instruction for jumping, punching, moving a weapon, and the like can be performed. Further, in a role-playing game (RPG) or a simulation RPG, an instruction for obtaining an item, selecting or deciding on a weapon or a command, and the like can be performed.

The − button 26e, the HOME button 26f, the + button 26g, and the power switch 26h are also push-button switches. The − button 26e is used for selecting a game mode. The HOME button 26f is used for displaying a game menu (menu screen). The + button 26g is used for starting (restarting) or pausing a game. The power switch 26h is used for turning on/off the game apparatus 12.

In the present embodiment, the controller 22 is not provided with a power switch for turning of/off the controller 22. The controller 22 is turned on by operating any one of the input means 26 of the controller 22, and is automatically turned off when the input means 26 are not performed for a certain time period (e.g. 30 seconds).

The B trigger switch 26i is also a push-button switch, and is used mainly for performing an input simulating a trigger for shooting a bullet, and for designating a position selected by using the controller 22. When the B trigger switch 26i is continuously pressed, a motion and a parameter of the player object can be maintained in a constant state. In a predetermined case, the B trigger switch 26i functions similarly as a normal B button, and is used for canceling an action decided by using the A button 26d, and the like.

Further, as shown in FIG. 3(E), an external extension connector 22b is provided on the rear surface of the housing 22a. As shown in FIG. 3(B), an indicator 22c is provided on the top surface of the housing 22a and near the rear surface. The external extension connector 22b is used for connecting to an extension controller (not shown). The indicator 22c consists of, for example, four LEDs, and any one of the four LEDs can be lit for indicating identification information (a controller number) of a controller 22 corresponding to the lit LED, and one or some of LEDs are lit for indicating the remaining amount of power of the controller 22, which is represented by the number of the lit LEDs.

Figure 4:
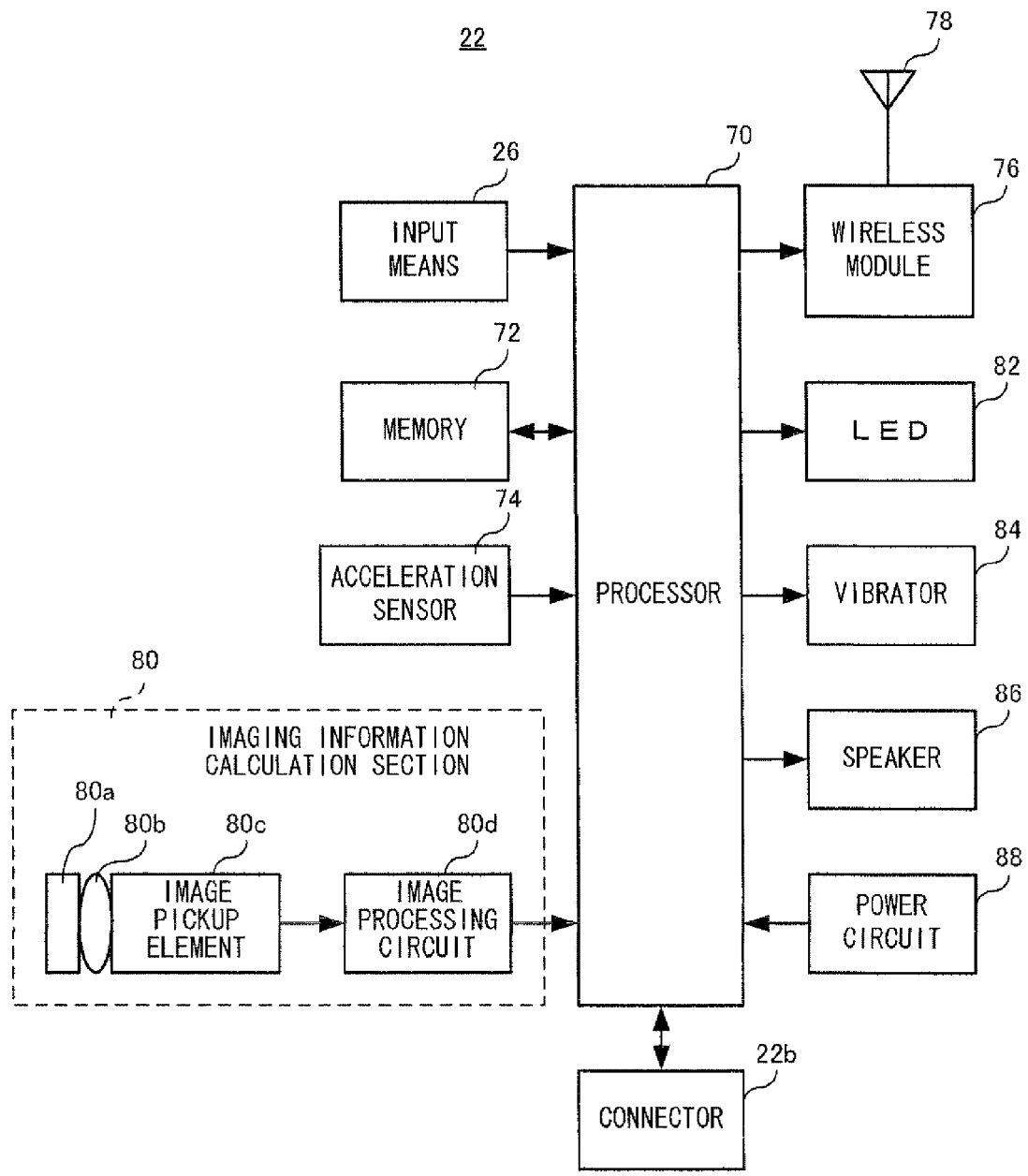
FIG. 4 is a block diagram showing an example of an electrical configuration of the controller.

Further, the controller 22 includes an imaging information calculation section 80 (see FIG. 4). As shown in FIG. 3(A), a light opening 22d for the imaging information calculation section 80 is provided on the front surface of the housing 22a. The controller 22 also includes a speaker 86 (see FIG. 4) that is provided in the housing 22a in corresponding relation to sound holes 22e that are provided in the top surface of the housing 22a and between the 1 button 26b and the HOME button 26f as shown in FIG. 3(B).

The shapes of the controller 22, and the shapes, the number, and the installation positions of the input means 26 as shown in FIGS. 3(A) to 3(E) are merely an example, and the present invention can be achieved with other shapes, other numbers, and other installation positions.

FIG. 4 is a block diagram showing an electrical configuration of the controller 22. Referring to FIG. 4, the controller 22 includes a processor 70 that is connected to the external extension connector 22b, the input means 26, a memory 72, an acceleration sensor 74, a wireless module 76, the imaging information calculation section 80, an LED 82 (the indicator 22c), a vibrator 84, the speaker 86, and a power circuit 88 through an internal bus (not shown). The wireless module 76 is connected to an antenna 78.

The processor 70 conducts the entire control of the controller 22, and transmits (inputs) information (input information) inputted by the input means 26, the acceleration sensor 74, and the imaging information calculation section 80, as input data, to the game apparatus 12 through the wireless module 76 and the antenna 78. At this time, the processor 70 uses the memory 72 as a work region and a buffer region.

Operation signals (operation data) from the aforementioned input means 26 (26a-26i) are inputted to the processor 70, and the processor 70 stores once the operation data in the memory 72.

The acceleration sensor 74 detects acceleration in three directions, i.e., a vertical direction (y axis), a horizontal direction (x axis), and a front-rear direction (z axis). The acceleration sensor 74 is typically an electrostatic capacitance type acceleration sensor, but may be of another type.

For example, the acceleration sensor 74 detects acceleration (ax, ay, az) along x axis, y axis, and z axis every first predetermined time period, and inputs data (acceleration data) of the detected acceleration to the processor 70. For example, the acceleration sensor 74 detects acceleration in each axial direction in a range between −2.0 g to 2.0 g (g denotes the gravitational acceleration; hereinafter, it is the same). The processor 70 detects the acceleration data, provided by the acceleration sensor 74, every second predetermined time period, and stores once the acceleration data in the memory 72. The processor 70 generates input data including at least one of the operation data, the acceleration data, and later-described marker coordinate data, and transmits the generated input data to the game apparatus 12 every third predetermined time period (e.g. 5 msec).

Although not shown in FIGS. 3(A) to 3(E) in the present embodiment, the acceleration sensor 74 is provided on a substrate in the housing 22a and near the cross key 26a.

By using, for example, the Bluetooth (registered trademark) technology, the wireless module 76 modulates a carrier wave of a predetermined frequency with the operation data and radiates the resultant weak radio signal from the antenna 78. In other words, the input data is modulated by the wireless module 76 into the weak radio signal and transmitted from the antenna 78 (controller 22). The weak radio signal is received by the wireless controller module 52 provided in the aforementioned game apparatus 12. The received weak radio signal is demodulated and decoded, and thus the game apparatus 12 (CPU 40) can obtain the input data from the controller 22. Then, the CPU 40 performs the game process in accordance with the obtained input data and a program (game program).

Further, as described above, the controller 22 is provided with the imaging information calculation section 80. The imaging information calculation section 80 includes an infrared filter 80a, a lens 80b, an image pickup element 80c, and an image processing circuit 80d. The infrared filter 80a allows, among light incident on the front surface of the controller 22, only infrared light to pass therethrough. As described above, the markers 340m and 340n located adjacent to the display screen of the monitor 34 are infrared LEDS that emit infrared light forward from the monitor 34. Thus, images of the markers 340m and 340n can be accurately taken by providing the infrared filter 80a. The lens 80b converges the infrared light that has passed through the infrared filter 80a, and outputs the infrared light to the image pickup element 80*c*. The image pickup element 80*c* is a solid-state image pickup element such as a CMOS sensor and a CCD. The image pickup element 80*c* takes an image of the infrared light collected by the lens 80*b*. In other words, the image pickup element 80*c* takes an image of only the infrared light that has passed through the infrared filter 80*c*. Then, the image pickup element 80*c* generates image data of the image. Hereinafter, an image taken by the image pickup element 80*c* is referred to as a taken image. The image data generated by the image pickup element 80*c* is processed by the image processing circuit 80*d*. The image processing circuit 80*d* calculates the position of a target (the markers 340*m* and 340*n*) whose image is to be taken, and outputs each coordinate value, representing the position, as imaging data to the processor 70 every fourth predetermined time period. The processing by the image processing circuit 80*d* will be described later.

(Load Controller)

Figure 5:
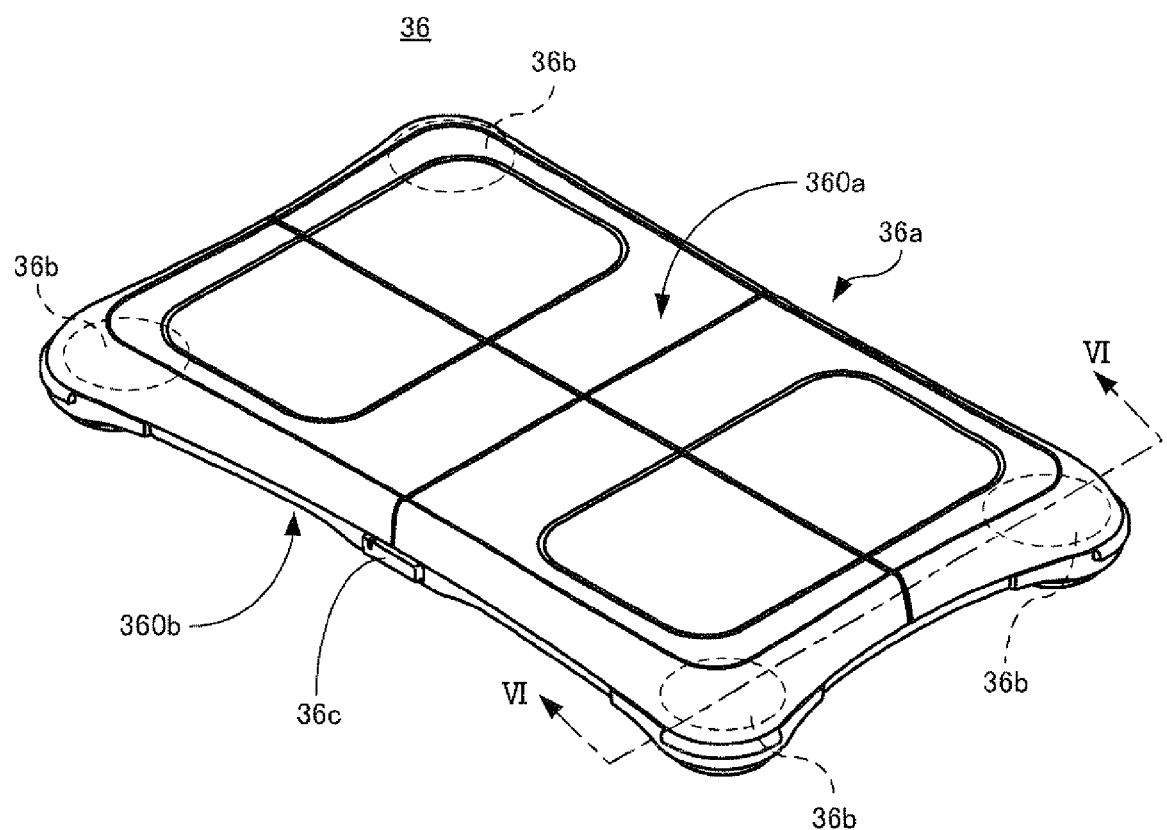
FIG. 5 is a perspective view of a load controller.

FIG. 5 is a perspective external view of the load controller 36 shown in FIG. 1. As shown in FIG. 5, the load controller 36 includes a stand 36*a* on which the player stands (on which the player puts his or her feet), and four load sensors 36*b* for detecting a load exerted on the stand 36*a*. Each load sensor 36*b* is contained in the stand 36*a* (see FIG. 7), and their locations are shown by dotted lines in FIG. 5.

The stand 36*a* is formed in a generally parallelepiped shape, and has a generally rectangular shape in top view. For example, the short side of the rectangle is set to about 30 cm, and the long side thereof is set to about 50 cm. The stand 36*a* has a flat top surface on which the player stands. The stand 36*a* has at four corners thereof side surfaces that are formed so as to partially project to have a cylindrical shape.

In the stand 36*a*, the four load sensors 36*b* are disposed at predetermined intervals. In the present embodiment, the four load sensors 36*b* are disposed at the periphery of the stand 36*a*, specifically, at the four corners thereof, respectively. The intervals among the load sensors 36*b* are set appropriately such that the load sensors 36*b* can accurately detect the intention of a game operation which is expressed by a manner of exerting a load on the stand 36*a* by the player.

Figure 6:
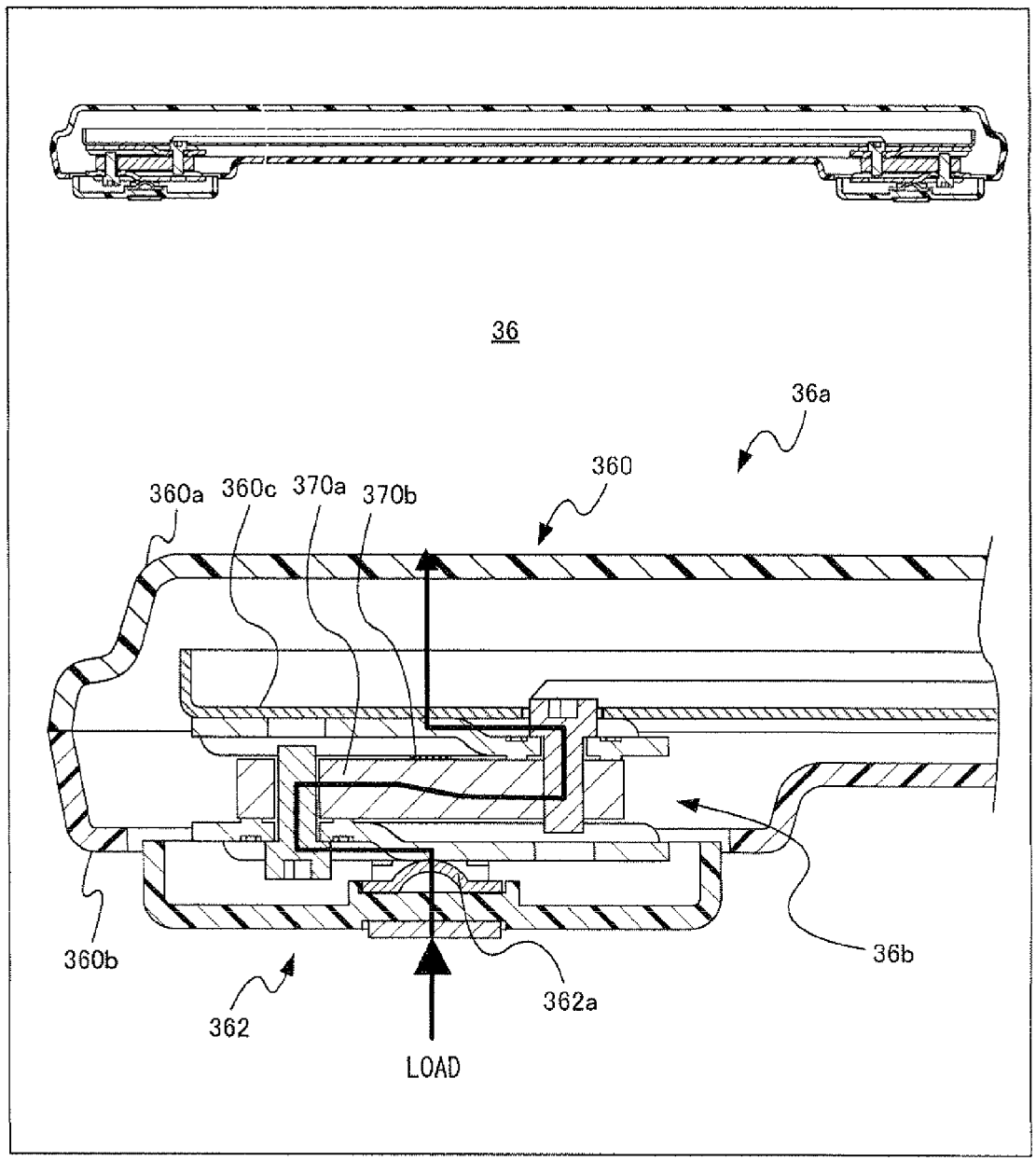
FIG. 6 is a cross-sectional view of the load controller taken along the VI-VI line in FIG. 5.

FIG. 6 shows a cross-sectional view of the load controller 36 taken along the VI-VI line in FIG. 5 and an enlarged view of a portion of the load controller 36 where the load sensor 36*b* is disposed. As is clear from FIG. 6, the stand 36*a* includes a support plate 360 on which the player stands, and legs 362. The legs 362 are provided at the positions where the load sensors 36*b* are disposed. In the present embodiment, because the four load sensors 36*b* are respectively disposed at the four corners, four legs 362 are provided. The legs 362 are formed in a generally cylindrical shape with a bottom, for example, by plastic molding. The load sensors 36*b* are respectively disposed on hemispherical parts 362*a* provided on the bottom surfaces in the legs 362. The support plate 360 is supported by the legs 362 through the load sensors 36*b*.

The support plate 360 includes an upper plate 360*a* that forms the top surface and a side surface upper portion, a lower plate 360*b* that forms a bottom surface and a side surface lower portion, and a mid plate 360*c* provided between the upper plate 360*a* and the lower plate 360*b*. The upper plate 360*a* and the lower plate 360*b* are formed, for example, by plastic molding, and integrated with each other by means of adhesion. The mid plate 360*c* is formed, for example, from one metallic plate by press molding. The mid plate 360*c* is fixed on the four load sensors 36*b*. The upper plate 360*a* has a grid-shaped rib (not shown) on the lower surface thereof, and is supported on the mid plate 360*c* through the rib. Thus, when the player stands on the stand 36*a*, the load is transmitted through the support plate 360, the load sensors 36*b*, and the legs 362. As shown by arrows in FIG. 6, the reaction from a floor, occurring by the exerted load, is transmitted to the upper plate 360*a* through the legs 362, the hemispherical parts 362*a*, the load sensors 36*b*, and the mid plate 360*c*.

The load sensors 36*b* are load converters that convert inputted loads into electric signals, for example, strain gauges (strain sensors) type load cells. In each load sensor 36*b*, according to the inputted load, a strain-generating body 370*a* deforms to generate strain. The strain is converted into a change of electric resistance by a strain sensor 370*b* attached to the strain-generating body 370*a*, and further converted into a voltage change. Thus, each load sensor 36*b* outputs a voltage signal indicative of the inputted load, from its output terminal.

Each load sensor 36*b* may be a load sensor of another type, such as a tuning fork vibration type, a string vibration type, an electrostatic capacitance type, a piezoelectric type, a magnetic strain type, and a gyro type.

Referring back to FIG. 5, the load controller 36 is provided with a power button 36*c*. When the power button 36*c* is turned on, electric power is supplied to each circuit component (see FIG. 7) of the load controller 36. It is noted that the load controller 36 may be turned on in accordance with an instruction from the game apparatus 12. When a state where the player does not stand on the load controller 36 continues for a certain time period (e.g. 30 seconds), the load controller 36 is turned off. However, when the power button 36*c* is pressed in a state where the load controller 36 is on, the load controller 36 may be turned off.

Figure 7:
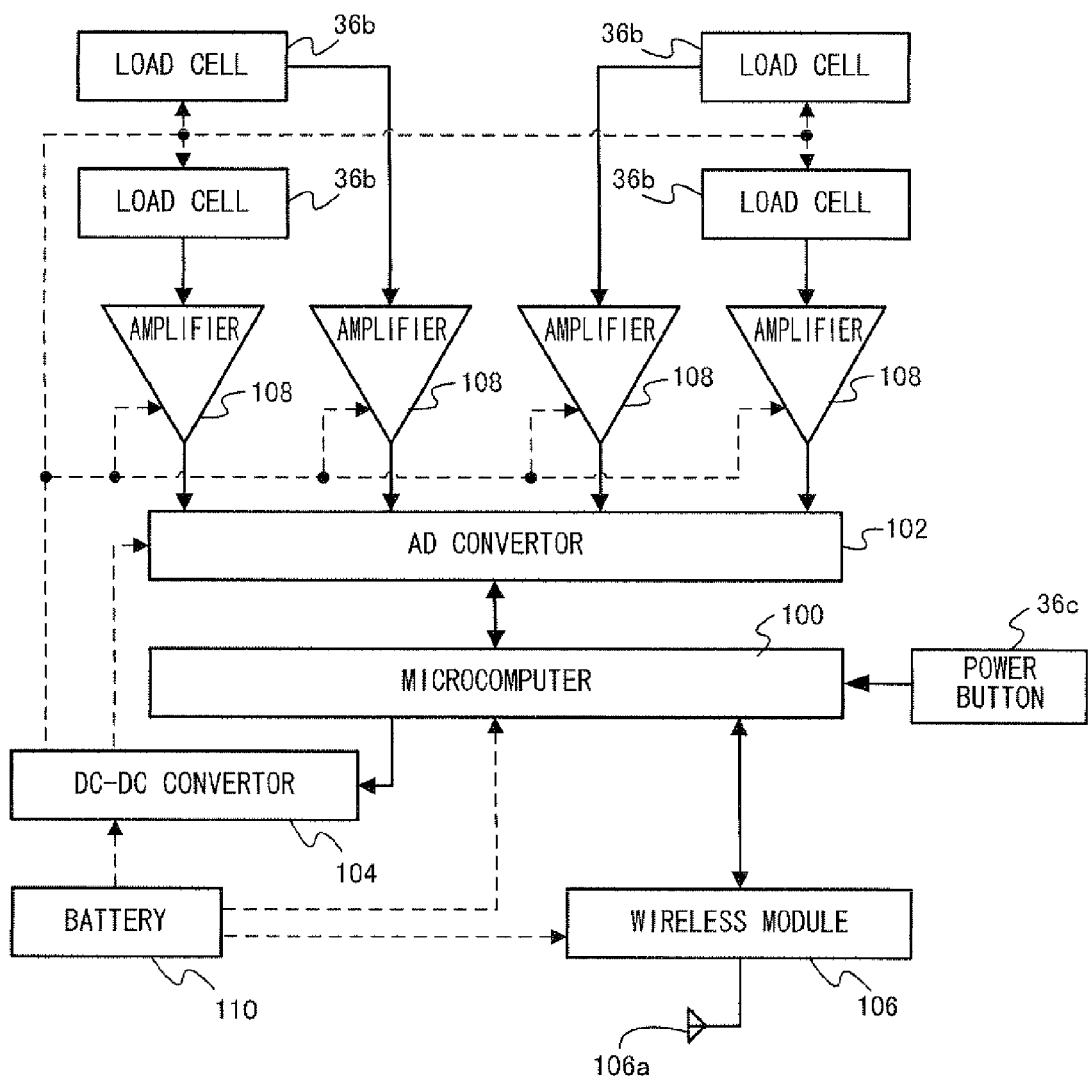
FIG. 7 is a block diagram showing an example of an electrical configuration of the load controller.

FIG. 7 is a block diagram showing an example of an electrical configuration of the load controller 36. In FIG. 7, flows of signals and communication are indicated by solid arrows. Dotted arrows indicate supply of electric power.

The load controller 36 includes a microcomputer 100 for controlling the operation of the load controller 36. The microcomputer 100 includes a CPU, a ROM, a RAM, and the like, which are not shown in the drawings. The CPU controls the operation of the load controller 36 in accordance with a program stored in the ROM.

The microcomputer 100 is connected to the power button 36*c*, an AD converter 102, a DC-DC converter 104, and a wireless module 106. The wireless module 106 is connected to an antenna 106*a*. The four load sensors 36*b* are shown as load cells 36*b* in FIG. 3. The four load sensors 36*b* are connected to the AD converter 102 through respective amplifiers 108.

Further, a battery 110 is contained in the load controller 36 for supplying electric power. In an alternative embodiment, instead of the battery, an AC adapter may be connected to the load controller 36 for supplying commercial power thereto. In this case, instead of the DC-DC converter, a power circuit, which converts alternating current into direct current and lowers and rectifies a direct current voltage, needs to be provided. In the present embodiment, electric power is supplied directly from the battery to the microcomputer 100 and the wireless module 106. In other words, the electric power is always supplied to the wireless module 106 and some components (the CPU) in the microcomputer 100 to detect whether or not the power button 36*c* is turned on and whether or not a command for turning on the power (load detection) is transmitted from the game apparatus 12. Meanwhile, the electric power is supplied from the battery 110 through the DC-DC converter 104 to the load sensors 36*b*, the AD converter 102, the amplifiers 108, and the battery 110. The DC-DC converter 104 converts a voltage value of direct current from the battery 110 into a different voltage value, and provides the resultant direct current to the load sensors 36*b*, the AD converter 102, and the amplifiers 108.

A supply of electric power to the load sensors 36*b*, the AD converter 102, and the amplifiers 108 may be conducted according to need by controlling the DC-DC converter 104 by the microcomputer 100. In other words, when it is determined that the load sensors 36*b* need to be activated to detect loads, the microcomputer 100 may control the DC-DC converter 104 so as to supply electric power to the load sensors 36*b*, the AD converter 102, and the amplifiers 108.

When the electric power is supplied, each load sensor 36*b* outputs a signal indicative of the inputted load. The signal is amplified by the corresponding amplifier 108, converted from the analog signal into digital data by the AD converter 102, and inputted to the microcomputer 100. Identification information of each load sensor 36*b*A is assigned to a detection value of each load sensor 36*b* such that it is possible to identify by which load sensor 36*b* the detection value is detected. As described above, the microcomputer 100 can obtain data indicative of each load detection value of the four load sensors 36*b* at the same time.

On the other hand, when it is determined that the load sensors 36*b* do not need to be activated, namely, that it is not a timing of load detection, the microcomputer 100 controls the DC-DC converter 104 so as to stop the supply of electric power to the load sensors 36*b*, the AD converter 102, and the amplifiers 108. As described above, in the load controller 36, because the load sensors 36*b* are activated to detect loads only when necessary, power consumption for load detection can be reduced.

A time when load detection is needed is typically a time when the game apparatus 12 (see FIG. 1) desires to obtain load data. For example, when the game apparatus 12 requires load information, the game apparatus 12 transmits a load obtaining command to the load controller 36. Upon receiving the load obtaining command from the game apparatus 12, the microcomputer 100 controls the DC-DC converter 104 so as to supply electric power to the load sensors 36*b* and the like for detecting loads. On the other hand, when not receiving a load obtaining command from the game apparatus 12, the microcomputer 100 controls the DC-DC converter 104 so as to stop the supply of electric power.

Alternatively, the microcomputer 100 may determine a timing of load detection every constant time period, and control the DC-DC converter 104. When such periodical load detection is conducted, information regarding the constant time period may be initially provided from the game apparatus 12 to the microcomputer 100 of the load controller 36 and stored therein, or may be stored in the microcomputer 100 in advance.

Data indicative of the detection values from the load sensors 36*b* is transmitted as operation data (input data) of the load controller 36 from the microcomputer 100 to the game apparatus 12 (see FIG. 1) through the wireless module 106 and the antenna 106*b*. For example, in the case of performing load detection according to a command from the game apparatus 12, when the microcomputer 100 receives the detection value data of the load sensors 36*b* from the AD converter 102, the microcomputer 100 transmits the detection value data to the game apparatus 12. Alternatively, the microcomputer 100 may transmit the detection value data to the game apparatus 12 every constant time period. When the interval of the load detection is longer than the interval of the transmission, data including load values detected at a plurality of detection timings until a transmission timing is transmitted.

It is noted that the wireless module 106 is set so as to perform communication according to the same wireless standard (the Bluetooth, a wireless LAN, and the like) as that for the wireless controller module 52 of the game apparatus 12. Thus, the CPU 40 of the game apparatus 12 is capable of transmitting a load obtaining command to the load controller 36 through the wireless controller module 52 and the like. The microcomputer 100 of the load controller 36 is capable of receiving the command from the game apparatus 12 through the wireless module 106 and the antenna 106*a*, and transmitting input data including a load detection value (or a load calculation value) of each load sensor 36*b* to the game apparatus 12.

In the case of a game executed based on the total of four load values detected by the four load sensors 36*b*, the player can stand at any position on the load controller 36 with respect to the four load sensors 36*b*, in other words, the player can play the game while standing at any position on the stand 36*a* and in any facing direction. However, depending on types of games, a process need to be executed while identifying which direction a load value detected by each load sensor 36*b* comes from with respect to the player, namely, it is necessary to know the positional relation between the four load sensors 36*b* of the load controller 36 and the player. In this case, for example, a positional relation between the four load sensors 36*b* and the player may be defined in advance, and it may be postulated that the player stands on the stand 36*a* so as to meet this predetermined positional relation. Typically, a positional relation in which two load sensors 36*b* are present on each of right and left sides or each of front and rear sides of the player standing at the center of the stand 36*a*, namely, a positional relation in which, when the player stands at the center of the stand 36*a* of the load controller 36, the load sensors 36*b* are present in the front right direction, the front left direction, the rear right direction, and the rear left direction from the player, respectively, is defined. In this case, in the present embodiment, because the stand 36*a* of the load controller 36 is formed in a rectangular shape in plan view and the power button 36*c* is provided at one side (long side) of the rectangle, it is defined in advance, using the power button 36*c* as a mark, that the player stands on the stand 36*a* such that the long side at which the power button 36*c* is provided is present in a predetermined direction (front, rear, left, or right) from the player. By doing so, a load value detected by each load sensor 36*b* becomes a load value in a predetermined direction (right front, left front, right rear, and left rear) from the player. Thus, the load controller 36 and the game apparatus 12 can identify which direction from the player each load detection value corresponds to, based on the identification information of each load sensor 36*b* which is included in the load detection value data and preset (prestored) position data indicative of a direction from the player to each load sensor 36*b*. Accordingly, it is possible to know the intention of a game operation, such as operation directions of front, rear, left, and right, which is expressed by the player.

The position of each load sensor 36*b* with respect to the player may not be defined in advance, and may be set by an input performed by the player at initial setting or at setting during a game. For example, the positional relation of each load sensor 36*b* with respect to the player can be specified by displaying an image for instructing the player to stand on a portion present in a predetermined direction (left front, right front, left rear, or right rear) from the player is displayed; and obtaining load values. Position data obtained by this setting may be generated and stored. Alternatively, a screen for selecting a position on the load controller 36 may be displayed on the monitor 34, and the player may be made to select in which direction from the player a mark (the power button 36*c*) is present, by an input with the controller 22. In accordance with this selection, position data of each load sensor 36*b* may be generated and stored.

(Game Play)

Figure 8:
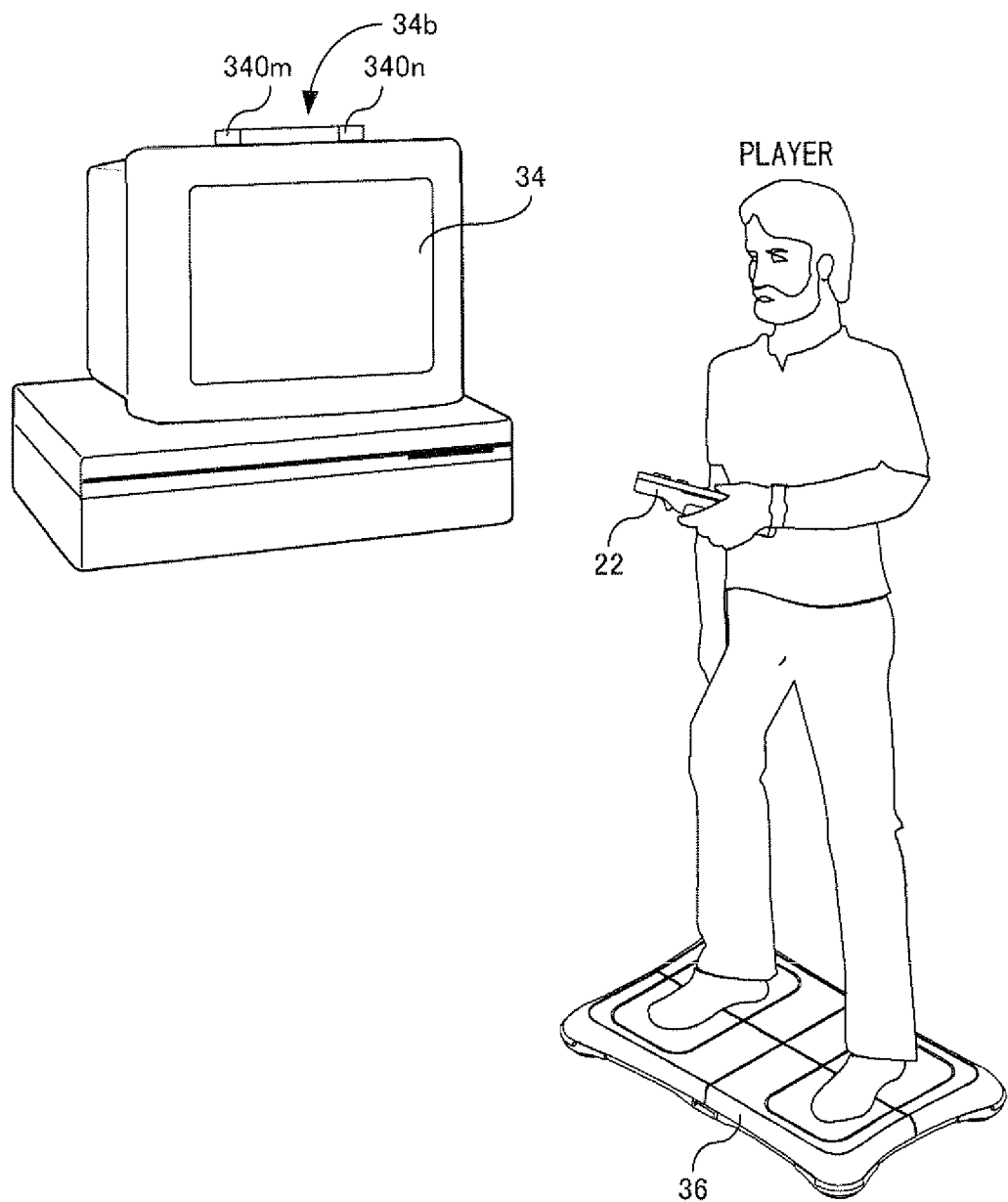
FIG. 8 is a view illustrating a state when a game is played by using the controller and the load controller.

FIG. 8 illustrates a state when a game is played by using the controller 22 and the load controller 36. As shown in FIG. 8, when a game is played with the game system 10 by using the controller 22 and the load controller 36, the player stands on the load controller 36 and holds the controller 22 with one hand. Specifically, the player stands on the load controller 36 and holds the controller 22 such that the front surface of the controller 22 (a side having the light opening 22*d* through which light is incident on the imaging information calculation section 80 taking an image of the light) faces the markers 340*m* and 340*n*. As is clear from FIG. 1, the markers 340*m* and 340*n* are arranged along the lateral direction of the screen of the monitor 34. In this state, the player performs game operations by changing the position to which the controller 22 points, or changing the distance between the controller 22 and each of the markers 340*m* and 340*n*.

FIG. 8 shows the case when the load controller 36 is placed lengthwise with respect to the screen of the monitor 34 (such that the long side direction thereof points toward the screen) and the player's right shoulder faces the screen of the monitors 34. However, the orientation of the load controller 36 with respect to the screen of the monitor 34 and the facing direction of the player can be changed as appropriate depending on types of games, and, for example, the load controller 36 may be oriented crosswise with respect to the screen of the monitor 34 (such that the long side direction thereof is parallel to the screen of the monitor 34) and the player faces the screen.

(Pointing)

Figure 9:
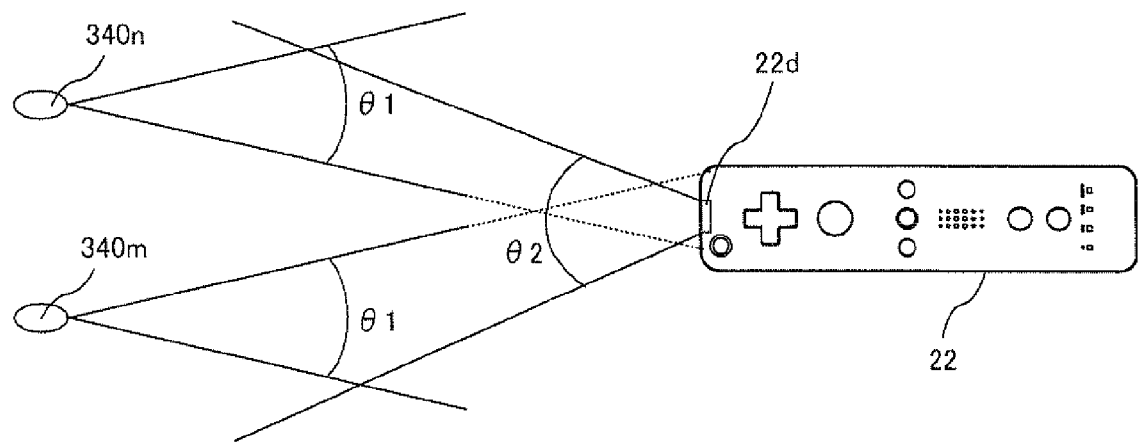
FIG. 9 is a view illustrating viewing angles of marker sections and the controller.

FIG. 9 is a view illustrating viewing angles of the markers 340*m* and 340*n* and the controller 22. As shown in FIG. 9, the markers 340*m* and 340*n* each emit infrared light at a viewing angle $\theta 1$. The image pickup element 80*c* of the imaging information calculation section 80 is capable of receiving light that is incident thereon in a range of a viewing angle $\theta 2$ centered at the view line direction of the controller 22. For example, the viewing angles $\theta 1$ of the markers 340*m* and 340*n* are 34° (half-value angle), and the viewing angle $\theta 2$ of the image pickup element 80*c* is 41°. The player holds the controller 22 such that the image pickup element 80*c* is oriented so as to be capable of receiving the infrared light from the markers 340*m* and 340*n*. Specifically, the player holds the controller 22 such that at least one of the markers 340*m* and 340*n* is present in the viewing angle $\theta 2$ of the image pickup element 80*c* and the controller 22 is present in the viewing angle $\theta 1$ of at least one of the markers 340*m* and 340*n*. In this state, the controller 22 is capable of detecting at least one of the markers 340*m* and 340*n*. The player can perform game operations by changing the position and the pointing direction of the controller 22 in a range that meets this state.

When the position and the pointing direction of the controller 22 are out of the range, it becomes impossible to perform the game operations based on the position and the pointing direction of the controller 22. Hereinafter, this range is referred to as "operable range".

Figure 10:
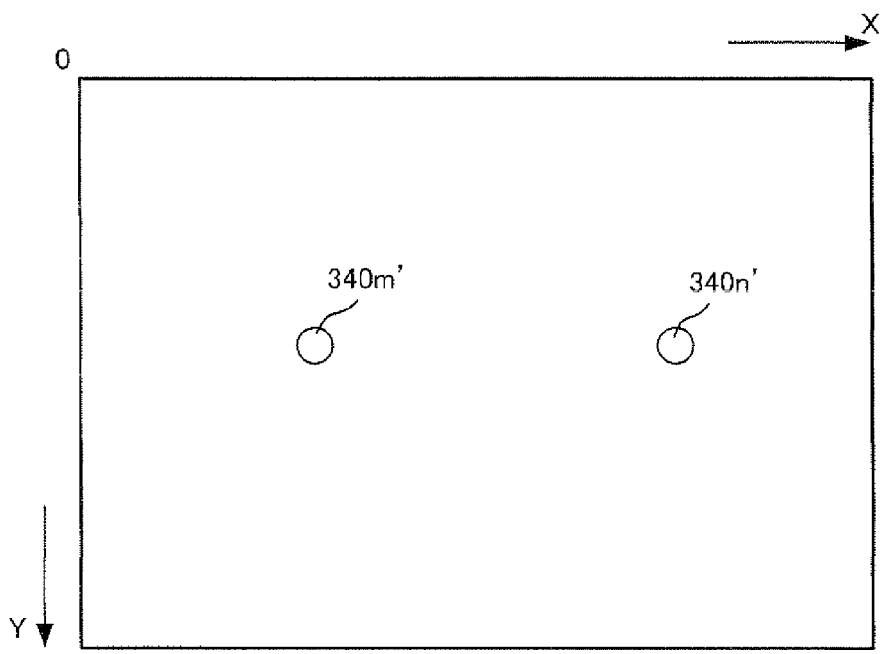
FIG. 10 is a view showing an example of a taken image including target images.

When the controller 22 is held in the operable range, an image of each of the markers 340*m* and 340*n* is taken by the imaging information calculation section 80. In other words, a taken image obtained by the image pickup element 80*c* includes the image (target image) of each of the markers 340*m* and 340*n* that are targets whose images are to be taken. FIG. 10 is a view showing an example of a taken image including target images. By using imaging data of a taken image including target images, the image processing circuit 60*d* calculates a coordinate (marker coordinate) representing the position of each of the markers 340*m* and 340*n* in the taken image.

In the imaging data of the taken image, the target images appear as regions that have a high brightness. Thus, first, the image processing circuit 80*d* detects the high brightness regions as candidates of the target images. Next, the image processing circuit 80*d* determines whether or not the high brightness regions indicate the target images, based on the sizes of the detected high brightness regions. The taken image may include images other than the target images due to sunlight incoming through a window and light from a fluorescent lamp in a room, in addition to the images 340*m'* and 340*n'* of the two markers 340*m* and 340*n* that are target images. The process of determining whether or not the high brightness regions indicate the target images is executed for distinguishing the images 340*m'* and 340*n'* of the markers 340*m* and 340*n*, which are target images, from the other images, and accurately detecting the target images. Specifically, in the determination process, whether or not the detected high brightness regions have a size in a predetermined range is determined. When the high brightness regions have a size in the predetermined range, it is determined that the high brightness regions indicate target images. When the high brightness regions do not have a size in the predetermined range, it is determined that the high brightness regions indicate images other than the target images.

Further, the image processing circuit 80*d* calculates the positions of the high brightness regions that are determined to indicate the target images as the result of the determination process. Specifically, the image processing circuit 80*d* calculates the positions of the centers of the high brightness regions. Here, the coordinates of the positions of the centers are referred to as marker coordinates. The positions of the centers can be calculated on a scale smaller than the resolution of the image pickup element 80*c*. Here, the resolution of an image taken by the image pickup element 80*d* is 126×96, and the positions of the centers are calculated on a scale of 1024×768. In other words, the coordinates of the positions of the centers are represented by integer values of (0,0) to (1024, 768).

It is noted that a position in the taken image is represented by a coordinate system (xy coordinate system) whose origin is at the upper left corner of the taken image, whose y axis positive direction is the downward direction, and whose x axis positive direction is the rightward direction.

When the target images are correctly detected, two high brightness regions are determined to indicate target images by the determination process, and thus the marker coordinates of two positions are calculated. The image processing circuit 80*d* outputs data indicative of the calculated marker coordinates of the two positions. The outputted data (marker coordinate data) of the marker coordinates is caused to be included in input data by the processor 70, and transmitted to the game apparatus 12 as described above.

When detecting the marker coordinate data from the received input data, the game apparatus 12 (CPU 40) can calculate the pointing position (pointing coordinate) of the controller 22 on the screen of the monitor 34 and the distances between the controller 22 and the markers 340*m* and 340*n* based on the marker coordinate data. Specifically, based on the position of the midpoint between the two marker coordinates, the position to which the controller 22 points, namely, the pointing position of the controller 22, is calculated. Thus, the controller 22 functions as a pointing device to point an arbitrary position on the screen of the monitor 34. Because the distance between the target images in the taken image changes in accordance with the distances between the controller 22 and the markers 340*m* and 340*n*, it is possible for the game apparatus 12 to know the distances between the controller 22 and the markers 340*m* and 340*n* by calculating the distance between the two marker coordinates.

Figure 11:
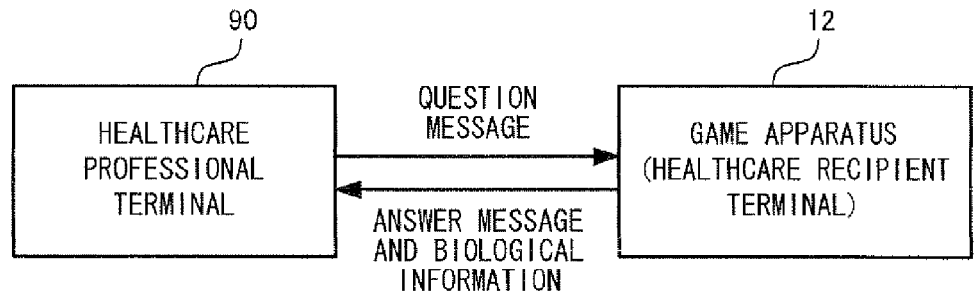
FIG. 11 is a view showing an outline of a health guidance support system.

FIG. 11 shows an outline of a health guidance support system of the present embodiment. The health guidance support system includes a healthcare professional terminal 90 operated by a healthcare professional such as a healthcare nurse and the like, and the game apparatus 12 operated by a healthcare recipient. As the healthcare professional terminal 90, an arbitrary information processing apparatus (e.g. a general-purpose personal computer including a CPU, a main memory, a hard disk, an input unit, and an output unit) can be used. In the present embodiment, the game apparatus 12 is used as a healthcare recipient terminal operated by the healthcare recipient. However, the present invention is not limited thereto, and an arbitrary information processing apparatus (e.g. a personal computer and the like) may be used as the healthcare recipient terminal.

The healthcare professional terminal 90 and the game apparatus 12 are capable of communicating with each other, for example, through the Internet. The healthcare professional terminal 90 creates a question message based on an input operation of the healthcare professional, and transmits the question message to the game apparatus 12. The question message is a message containing questions that the healthcare professional asks the healthcare recipient, for example, for confirming the health condition and the number of meals of the healthcare recipient.

The game apparatus 12 creates an answer message based on an input operation of the healthcare recipient, and transmits the answer message to the healthcare professional terminal 90 together with biological information of the healthcare recipient. The answer message is a message containing answers to the questions contained in the question message received from the healthcare professional terminal 90. The biological information is various information useful for health guidance, including: information regarding a body, such as weight, body fat percentage, and the like; information regarding exercise, such as the number of steps taken, exercise time, and the like; and information regarding vital signs, such as blood pressure, body temperature, heart rate, and the like. The biological information is automatically transmitted by the game apparatus 12 when the answer message is transmitted to the healthcare professional terminal 90. Thus, an operation, such as an operation of attaching the biological information to the answer message by the healthcare recipient, is not needed.

(Flow of Biological Information)

Figure 12:
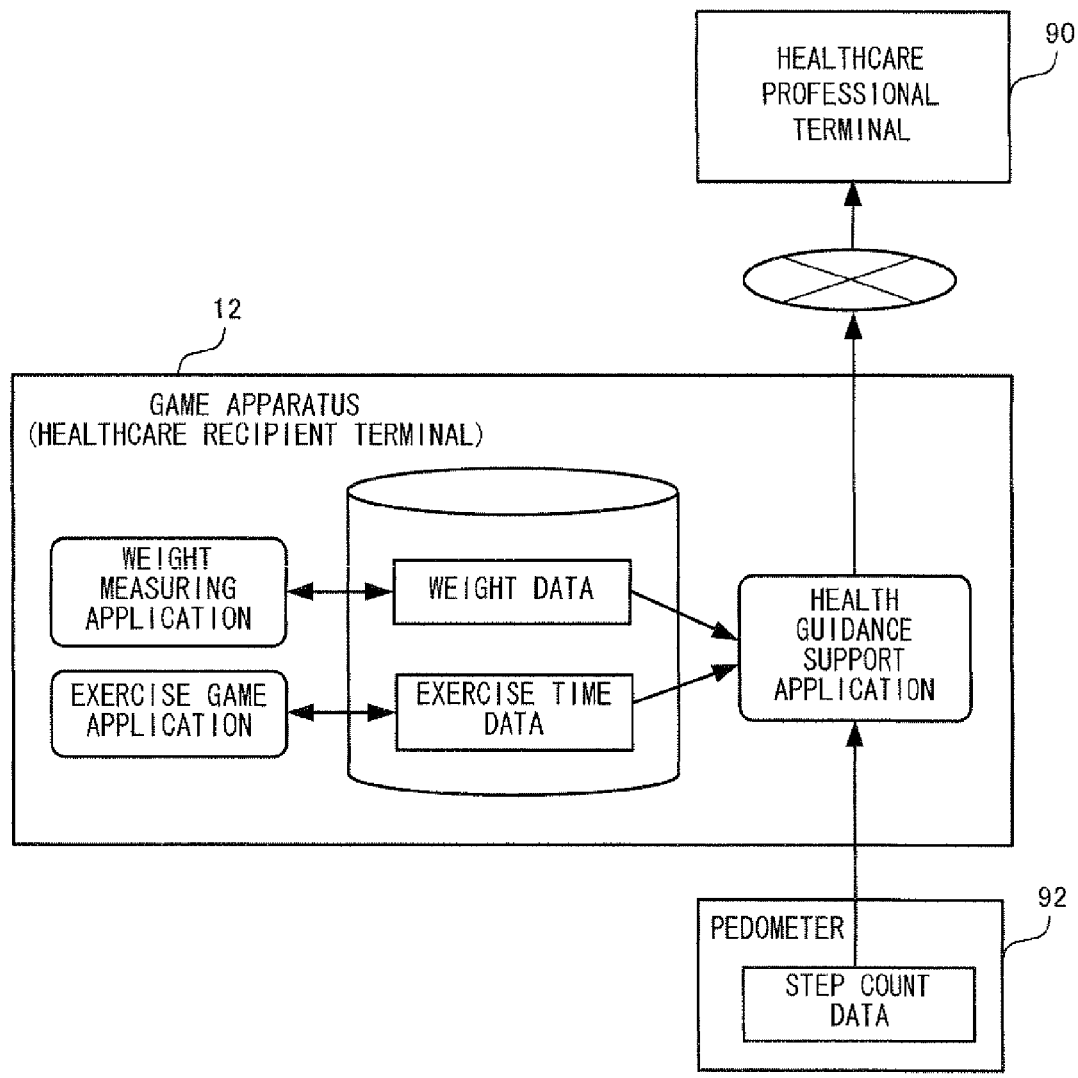
FIG. 12 is a view showing a flow of biological information (weight data, exercise time data, and step count data)

FIG. 12 shows an example of a flow of biological information. In the present embodiment, as the biological information, weight data, exercise time data, and step count data are transmitted from the game apparatus 12 to the healthcare professional terminal 90 together with the answer message. The weight data is stored as saved data in the flash memory 44 of the game apparatus 12 when a weight measuring application program (hereinafter, an application program is referred to merely as an application) using the load controller 36 is executed in the game apparatus 12. The exercise time data is stored as saved data in the flash memory 44 of the game apparatus 12 when an exercise game application using the controller 22 and the load controller 36 is executed in the game apparatus 12. It is noted that the weight measuring application and the exercise game application may be realized by one application (an application that can cause the CPU 40 to execute a weight measuring process and an exercise game process). The step count data is transmitted to the game apparatus 12 from a pedometer 92 carried by the healthcare recipient. A communication method for the communication between the pedometer 92 and the game apparatus 12 is arbitrary. For example, the pedometer 92 may communicate with the game apparatus 12 through a cable, by means of infrared communication, or through a hand-held game apparatus.

A health guidance support application is an application for causing the game apparatus 12 to function as a part of the health guidance support system, and causes the CPU 40 of the game apparatus 12 to execute a process of receiving a question message from the healthcare professional terminal 90, a process of creating an answer message, a process of obtaining biological information, and a process of transmitting the answer message and the biological information. The weight data and the exercise time data are obtained from saved data of the weight measuring application and the exercise game application, which are stored in the flash memory 44 of the game apparatus 12, and the step count data is obtained from the pedometer 92 by means of communication. When the step count data has been already obtained from the pedometer 92 by means of communication and stored in the flash memory 44, the step count data can be obtained from the flash memory 44.

(Data in Flash Memory)

Figure 13:
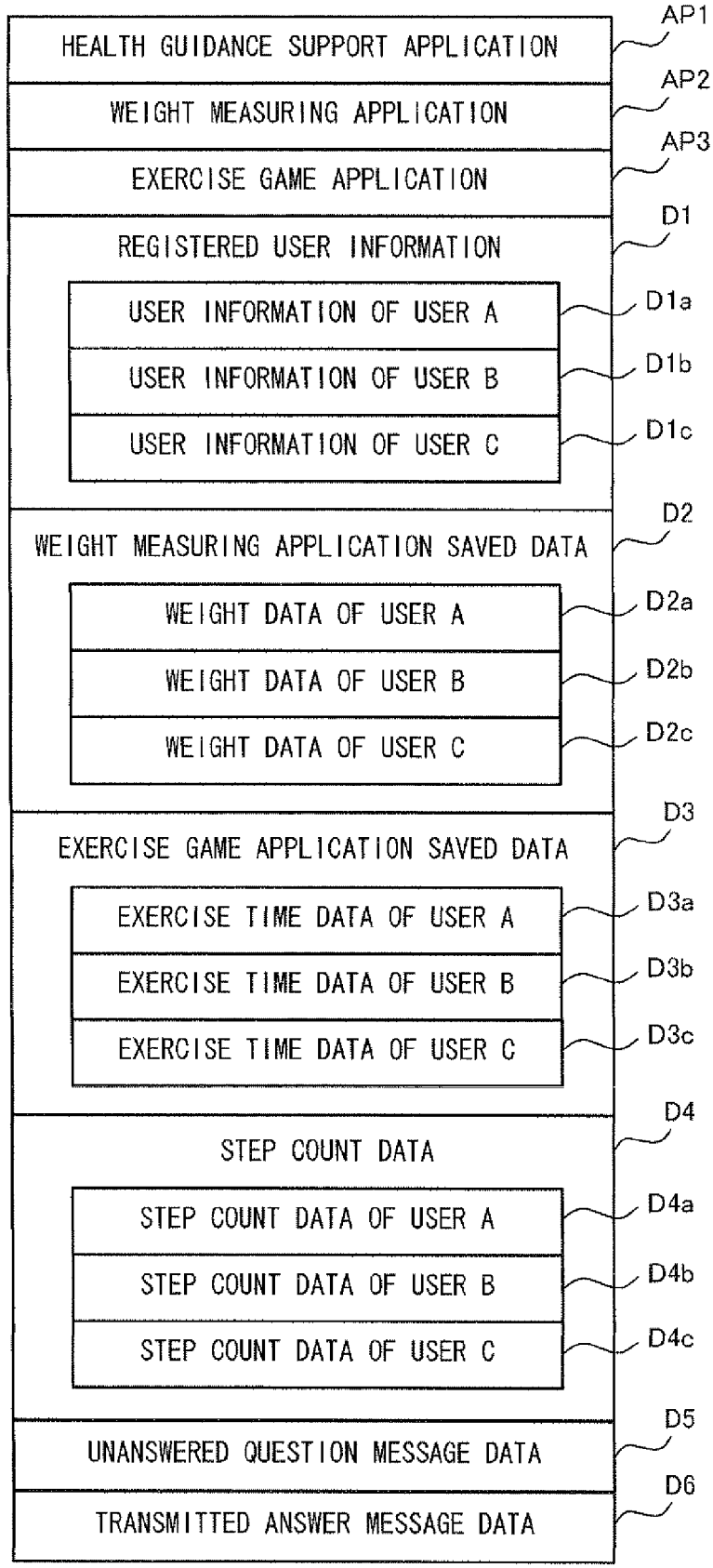
FIG. 13 is a view showing information stored in a flash memory.

FIG. 13 shows an example of data in the flash memory 44. In the flash memory 44, application programs, such as a health guidance support application AP1, a weight measuring application AP2, an exercise game application AP3, and the like, are stored. These application programs do not necessarily need to be stored in the flash memory 44. For example, these application programs may be supplied to the game apparatus 12 through a computer-readable storage medium such as an optical disc, a magnetic disc, a memory card, and the like, or may be supplied to the game apparatus 12 by means of wire or wireless communication. The application programs supplied to the game apparatus 12 may be stored in the flash memory 44.

In addition to the applications, various data, such as registered user information D1, weight measuring application saved data D2, exercise game application saved data D3, step count data D4, unanswered question message data D5, transmitted answer message data D6, and the like, are stored in the flash memory 44.

The registered user information D1 is information (name, nickname, icon, and the like) regarding the user of the game apparatus 12, and in the present embodiment, three users A to C are registered as users of the game apparatus 12. In other words, as the registered user information D1, user information D1*a* of the user A, user information D1*b* of the user B, and user information D1*c* of the user C are stored in the flash memory 44.

The weight measuring application saved data D2 is saved data that is generated or updated when the weight measuring application AP2 is executed in the game apparatus 12, and includes weight data of each user. Here, the weight measuring application saved data D2 includes weight data D2*a* of the user A, weight data D2*b* of the user B, and weight data D2*c* of the user C. In the weight data, for example, measuring results of a plurality of times for past several months as well as the latest measuring results are registered together with their measurement dates.

The exercise game application saved data D3 is saved data that is generated or updated when the exercise game application AP3 is executed in the game apparatus 12, and includes exercise time data of each user. Here, the exercise game application saved data D3 includes exercise time data D1a of the user A, exercise time data D3b of the user B, and exercise time data D3c of the user C. In the exercise time data, for example, measuring results of a plurality of times for past several months as well as the latest measuring results are registered together with their measurement dates.

The step count data D4 is data to be transmitted to the game apparatus 12 from the pedometer 92 carried by the user, and is generated or updated when the step count data is transmitted from the pedometer 92 to the game apparatus 12. The pedometer 92 has a step count function of counting the number of steps taken by the user, a step count data storing function of storing the counted number of steps and the measurement data as step count data in a built-in storage unit, and a step count data transmission function of transmitting the step count data stored in the built-in storage unit to the game apparatus 12. Here, the step count data D4 includes step count data D4a of the user A, step count data D4b of the user B, and step count data D4c of the user C.

The unanswered question message data D5 is a group of unanswered question messages received by the game apparatus 12 from the healthcare professional terminal 90. Upon receiving a question message from the healthcare professional terminal 90, the game apparatus 12 stores the question message as a part of the unanswered question message data D5 in the flash memory 44.

The transmitted answer message data D6 is a group of answer messages transmitted from the game apparatus 12 to the healthcare professional terminal 90.

(Weight Measuring Process in Game Apparatus)

Figure 14:
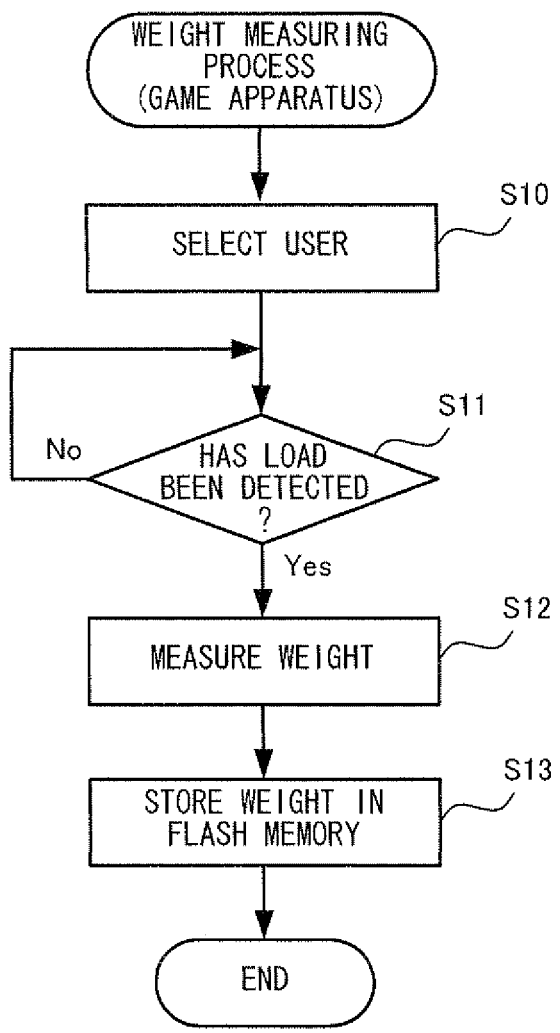
FIG. 14 is a flow chart showing a procedure of a weight measuring process executed by the game apparatus.

First, an operation of the game apparatus 12 when the weight measuring application AP2 is executed in the game apparatus 12 will be described. FIG. 14 is a flow chart showing a procedure of the weight measuring process executed by the CPU 40 of the game apparatus 12 in accordance with the weight measuring application AP2.

When the weight measuring process is started, at a step S10, the CPU 40 refers to the registered user information D1, and selects an user whose weight is to be measured, from among the users registered to the game apparatus 12. The selection of the user is performed based on an input operation (e.g. an input signal from the controller 22) of the user. It is noted that when the user whose weight is to be measured has not been registered to the game apparatus 12, a process of registering the user is executed according to need.

At a step S11, the CPU 40 determines, based on a signal from the load controller 36, whether or not the load controller 36 has detected a load. Then, when the load controller 36 has detected a load, the processing proceeds to a step S12. When the load controller 36 has not detected a load, the CPU 40 waits until a load is detected.

At the step S12, the CPU 40 measures, based on the signal from the load controller 36, the weight of the user standing on the load controller 36.

At a step S13, the CPU 40 stores the weight measured at the step S12 together with the measurement date as weight data of the weighed user (i.e. the user selected at the step S10) in the flash memory 44. It is noted that when weight data of the user has been present in the flash memory 44, the latest measuring result is added to the weight data. Then, the weight measuring process ends.

(Exercise Time Measuring Process in Game Apparatus)

Figure 15:
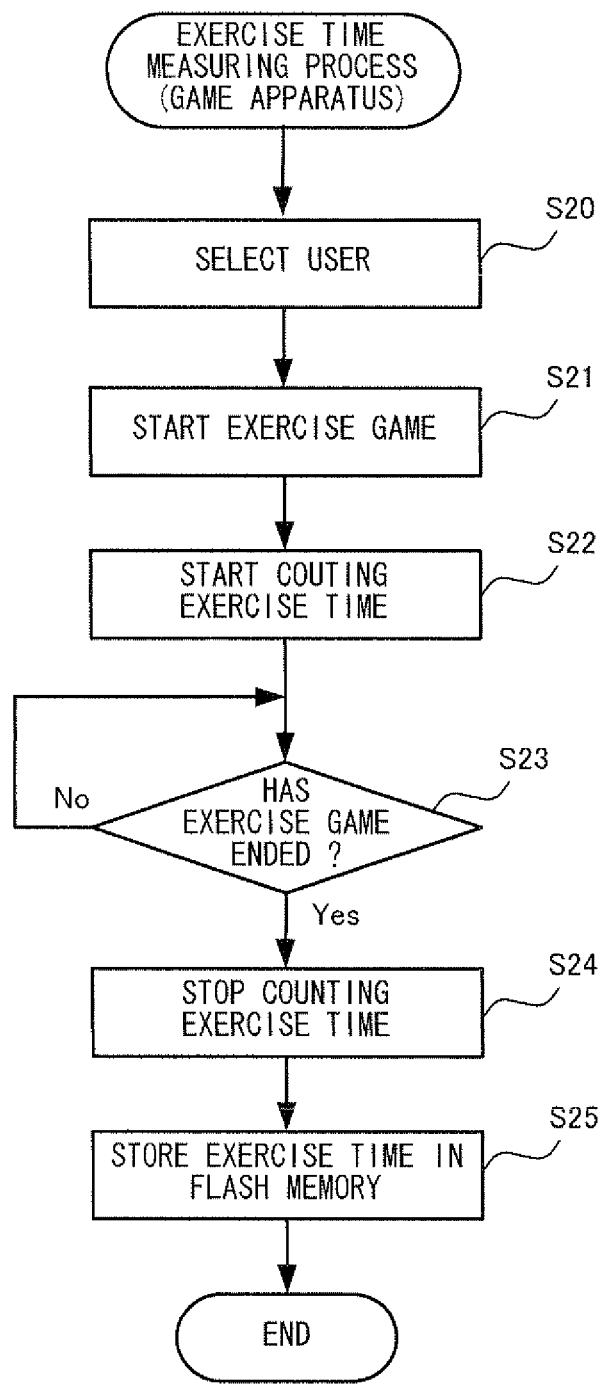
FIG. 15 is a flow chart showing a procedure of an exercise time measuring process executed by the game apparatus.

The following will describe an operation of the game apparatus 12 when the exercise game application AP3 is executed in the game apparatus 12. FIG. 15 is a flowchart showing a procedure of an exercise time measuring process executed by the CPU 40 of the game apparatus 12 in accordance with the exercise game application AP3.

When the exercise time measuring process is started, at a step S20, the CPU 40 refers to the registered user information D1, and selects a user who is to play an exercise game, from among the users registered to the game apparatus 12. The selection of the user is performed based on an input operation (e.g. an input signal from the controller 22) of the user. It is noted that when the user who is to play the exercise game has not been registered to the game apparatus 12, the process of registering the user is executed according to need.

At a step S21, the CPU 40 starts the exercise game using the controller 22 or the load controller 36. Examples of the exercise game include: a boxing game in which a player shadow-boxes holding the controllers 22 with his or her hands; a hiking game in which a player repeatedly steps on the load controller 36; and the like.

At a step S22, the CPU 40 starts counting an exercise time.

At a step S23, the CPU 40 determines whether or not the exercise game has ended. When the exercise game has ended, the processing proceeds to a step S24. When the exercise game continues, the CPU 40 waits until the exercise game ends.

At the step S24, the CPU 40 stops counting the exercise time.

At a step S25, the CPU 40 stores the counted exercise time together with the measurement date as exercise time data of the user who plays the exercise game (i.e. the user selected at the step S20) in the flash memory 44. It is noted that when exercise time data of the user has been present in the flash memory 44, the latest measuring result is added to the exercise time data. Then, the exercise time measuring process ends Instead of storing the counted exercise time as exercise time data, a value obtained by multiplying the counted exercise time by a coefficient according to an exercise load exerted on the user playing the exercise game may be stored as exercise time data.

(Question Process in Healthcare Professional Terminal)

Figure 16:
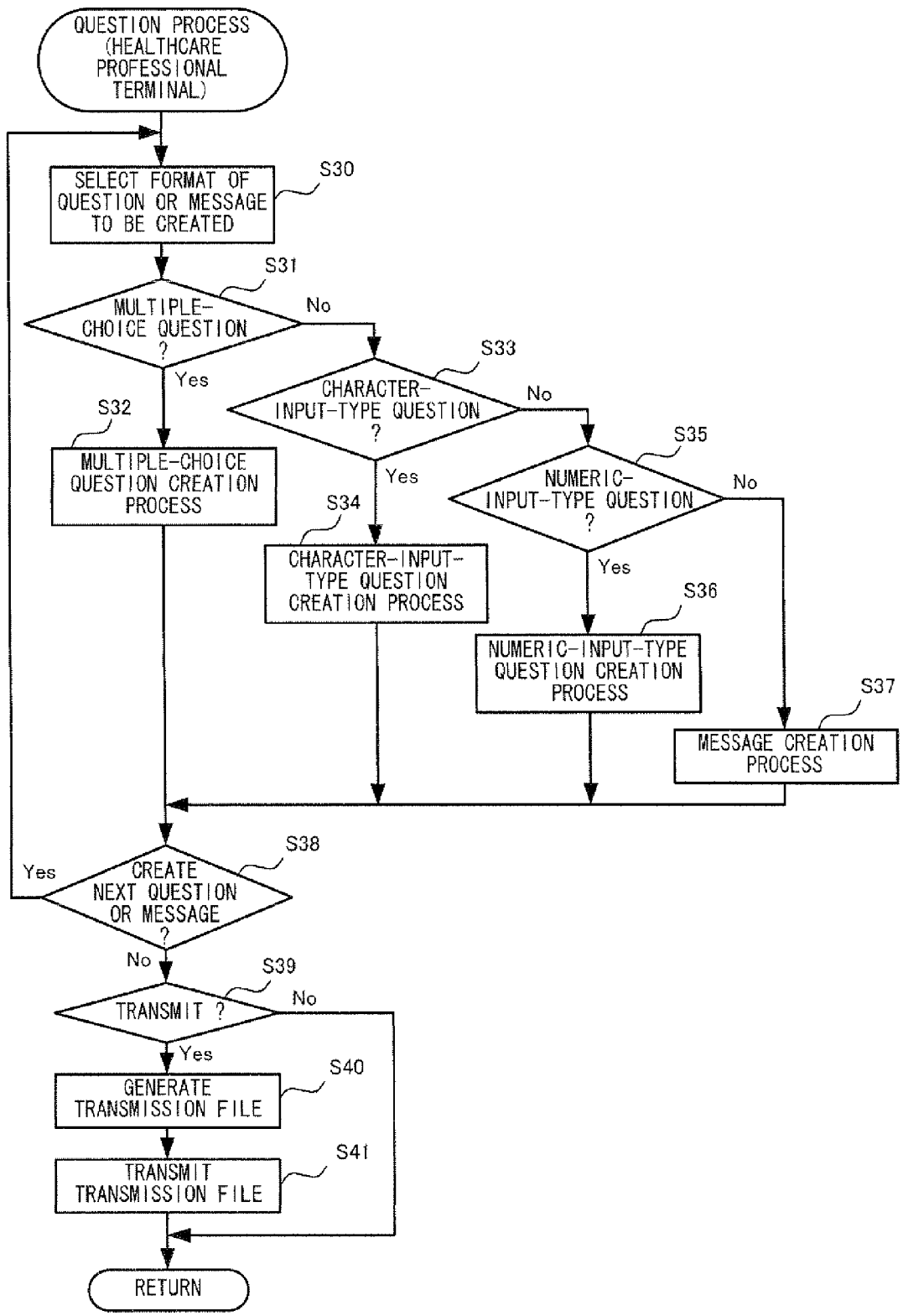
FIG. 16 is a flow chart showing a procedure of a question process executed by a healthcare professional terminal.

The following will describe an operation of the game apparatus 12 when a question message creation application is executed in the healthcare professional terminal 90. The question message creation application is typically supplied to the healthcare professional terminal 90 through a computer-readable storage medium such as an optical disc and the like or through the Internet, and installed in a hard disk of the healthcare professional terminal 90. FIG. 16 is a flow chart showing a procedure of a question process executed by the CPU of the healthcare professional terminal 90 in accordance with the question message creation application.

Figure 24:
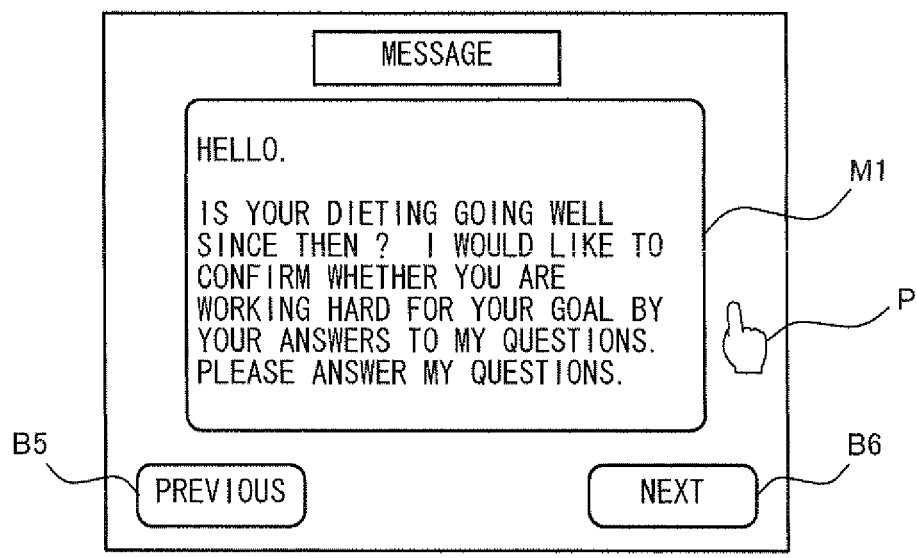
FIG. 24 is a view showing an example of a message display screen.
Figure 25:
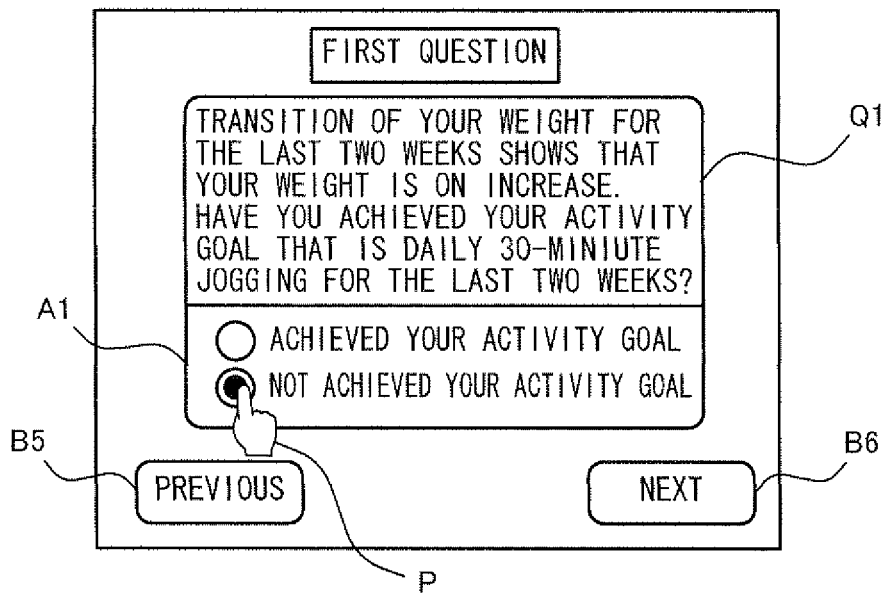
FIG. 25 is a view showing an example of a multiple-choice answer screen.
Figure 26:
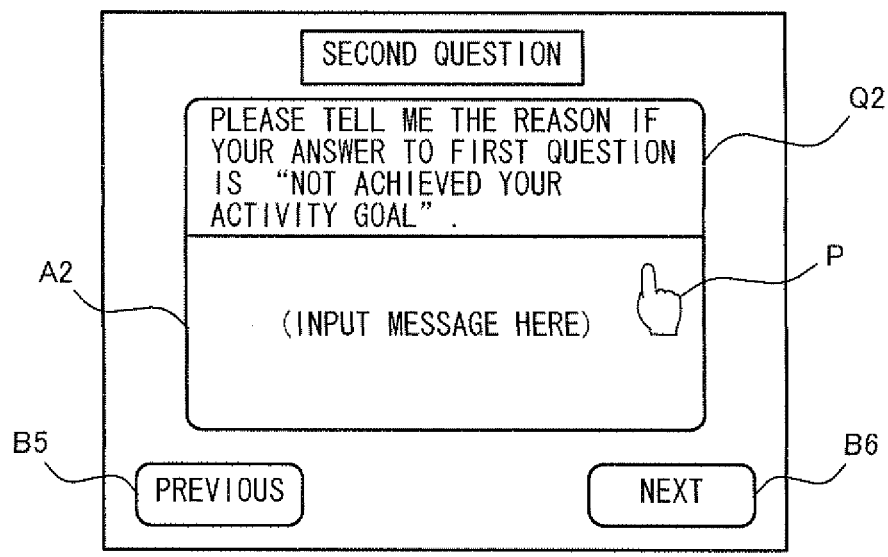
FIG. 26 is a view showing an example of a character-input-type answer screen.
Figure 27:
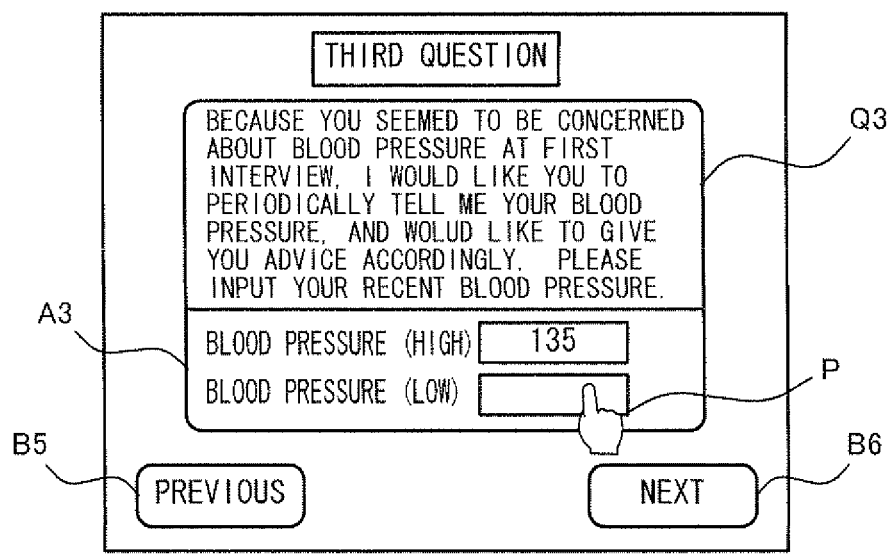
FIG. 27 is a view showing an example of a numeric-input-type answer screen.

When the question process is started, at a step S30, the CPU of the healthcare professional terminal 90 selects a format of a question or a message to be created, based on an input operation by the healthcare professional. In the present embodiment, a question message transmitted from the healthcare professional terminal 90 to the game apparatus 12 contains a group of one or more questions or messages. Specifically, the healthcare professional can create a question message by combining arbitrarily a "multiple-choice question", "character-input-type question", a "numeric-input-type question", and a "message" according to need. The "multiple-choice question" is a question including a question section Q1 and a choice section A1 as shown in FIG. 25. FIG. 25 shows an image that is displayed on the monitor 34 when the user of the game apparatus 12 answers the "multiple-choice question". The "character-input-type question" is a question including a question section Q2 and a character input section A2 as shown in FIG. 26. The "numeric-inputtype question" is a question including a question section Q3 and a numeric input section A3 as shown in FIG. 27. The "message" is a message including only a message section M1 as shown in FIG. 24.

At a step S31, the CPU of the healthcare professional terminal 90 determines whether or not the format selected at the step S30 is the "multiple-choice question", When the format is the "multiple-choice question", the CPU of the processing proceeds to a step S32. When the format is not the "multiple-choice question", the processing proceeds to a step S33.

At the step S32, the CPU of the healthcare professional terminal 90 executes a multiple-choice question creation process. Specifically, in accordance with an input operation by the healthcare professional, the CPU of the healthcare professional terminal 90 creates a sentence in the question section Q1 and choices in the choice section A1 as shown in FIG. 25. Then, the processing proceeds to a step S38.

At the step S33, the CPU of the healthcare professional terminal 90 determines whether or not the format selected at the step S30 is the "character-input-type question". When the format is the "character-input-type question", the processing proceeds to a step S34. When the format is not the "character-input-type question", the processing proceeds to a step S35.

At the step S34, the CPU of the healthcare professional terminal 90 executes a character-input-type question creation process. Specifically, in accordance with an input operation by the healthcare professional, the CPU of the healthcare professional terminal 90 creates a sentence in the question section Q2 as shown in FIG. 26. Then, the processing proceeds to the step S38.

At the step S35, the CPU of the healthcare professional terminal 90 determines whether or not the format selected at the step S30 is the "numeric-input-type question". When the format is the "numeric-input-type question", the processing proceeds to a step S36. When the format is not the "numeric-input-type question", the processing proceeds to a step S37.

At the step S36, the CPU of the healthcare professional terminal 90 executes a numeric-input-type question creation process. Specifically, in accordance with an input operation by the healthcare professional, the CPU of the healthcare professional terminal 90 creates sentences in the question section Q3 and phrases in the numeric input section A3 as shown in FIG. 27. Then, the processing proceeds to the step S38.

At the step S37, the CPU of the healthcare professional terminal 90 executes a message creation process. Specifically, in accordance with an input operation by the healthcare professional, the CPU of the healthcare professional terminal 90 creates sentences in the message section M1 as shown in FIG. 24. Then, the processing proceeds to the step S38.

At the step S38, the CPU of the healthcare professional terminal 90 determines, based on an input operation by the healthcare professional, whether or not to create the next question or message. When the CPU of the healthcare professional terminal 90 creates the next question or message, the processing returns to the step S30. When the CPU of the healthcare professional terminal 90 does not create the next question or message, the processing proceeds to a step S39.

At the step S39, the CPU of the healthcare professional terminal 90 determines, based on an input operation by the healthcare professional, whether to transmit the created question message to the game apparatus 12 of the healthcare recipient. When the CPU of the healthcare professional terminal 90 transmits the created question message, the processing proceeds to a step S40. When the CPU of the healthcare professional terminal 90 does not transmit the created question message, the question process ends.

At the step S40, the CPU of the healthcare professional terminal 90 generates a transmission file by forming the created question message (a group of one or more questions or messages) into one file.

At a step S41, the CPU of the healthcare professional terminal 90 transmits the transmission file generated at the step S40 to the game apparatus 12 of the healthcare recipient. Then, the question process ends. Regarding transmission of a file from the healthcare professional terminal 90 to the game apparatus 12, for example, a generated transmission file can be transmitted as an attached file of an e-mail message by using a general transfer protocol of. In this case, the e-mail message may be blank or a fixed phrase may be contained in the e-mail message.

(Main Process in Game Apparatus)

Figure 17:
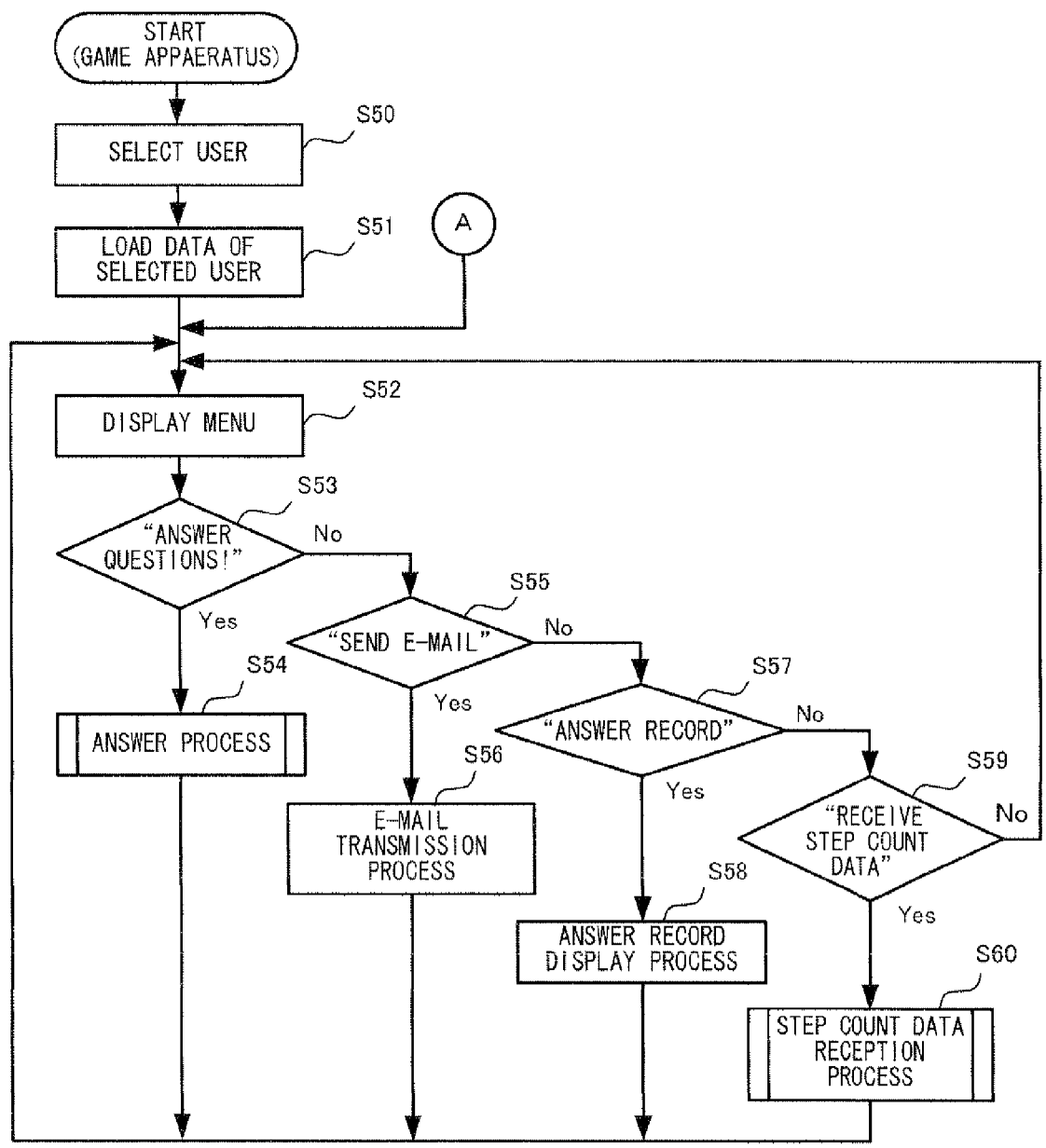
FIG. 17 is a flow chart showing a procedure of a main process executed by the game apparatus.

The following will describe an operation of the game apparatus 12 when the health guidance support application AP1 is executed in the game apparatus 12. FIG. 17 is a flow chart showing a procedure of a main process executed by the CPU 40 of the game apparatus 12 in accordance with the health guidance support application AP1.

When the main process is started, at a step S50, the CPU 40 refers to the registered user information D1, and selects a user who is to use the health guidance support application, from among the users registered to the game apparatus 12. The selection of the user is performed based on an input operation (e.g. an input signal from the controller 22) of the user. It is noted that when the user who is to use the health guidance support application has not been registered to the game apparatus 12, the process of registering the user is executed according to need.

At a step S51, the CPU 40 loads data (unanswered question message data D5 to the user, and the like) of the user, selected at the step S50, from the flash memory 44 to the internal main memory 42e according to need.

Figure 23:
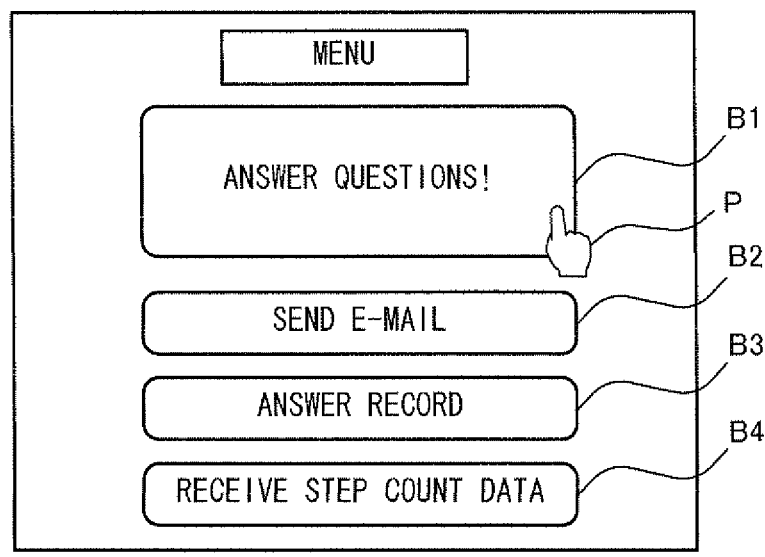
FIG. 23 is a view showing an example of a menu display screen.

At a step S52, the CPU 40 displays a menu screen on the monitor 34. In the menu screen, for example, an "ANSWER QUESTION!" button B1, a "SEND E-MAIL" button 52, a "ANSWER RECORD" button B3, and a "RECEIVE STEP COUNT DATA" button B4 are displayed as shown in FIG. 23. The user can move a pointer P on the screen by operating the controller 22 for selecting a desired button from among these buttons.

At a step S53, the CPU 40 determines whether or not the "ANSWER QUESTION!" button B1 has been selected. When the "ANSWER QUESTION!" button B1 has been selected, the processing proceeds to a step S54. When the "ANSWER QUESTION!" button B1 has not been selected, the processing proceeds to a step S55.

At the step S54, the CPU 40 executes an answer process. The answer process is a process of creating an answer message to a question message from the healthcare professional, and of transmitting the answer message to the healthcare professional terminal 90. The answer process will be described in detail later. When the answer process ends, the processing returns to the step S52.

At the step S55, the CPU 40 determines whether or not the "SEND E-MAIL" button B2 has been selected. When the "SEND E-MAIL" button 132 has been selected, the processing proceeds to a step S56. When the "SEND E-MAIL" button B2 has not been selected, the processing proceeds to a step S57.

At the step S56, the CPU 40 executes an e-mail transmission process. The e-mail transmission process is a process of creating a message (discussion about health maintenance) to the healthcare professional based on an input operation (e.g. an input signal from the controller 22) of the user, and of transmitting the message to the healthcare professional terminal 90. When the e-mail transmission process ends, the processing returns to the step S52.

At the step S57, the CPU 40 determines whether or not the "ANSWER RECORD" button B3 has been selected. When the "ANSWER RECORD" button B3 has been selected, the processing proceeds to a step S58. When the "ANSWER RECORD" button B3 has not been selected, the processing proceeds to a step S59.

At the step S58, the CPU 40 executes an answer record display process. The answer record display process is a process for the user to freely view the transmitted answer message data D6 stored in the flash memory 44. Thus, according to need, the user can confirm the contents of answer messages transmitted previously. When the answer record display process ends, the processing returns to the step S52.

At the step S59, the CPU 40 determines whether or not the "RECEIVE STEP COUNT DATA" button B4 has been selected. When the "RECEIVE STEP COUNT DATA" button B4 has been selected, the processing proceeds to a step S60. When the "RECEIVE STEP COUNT DATA" button B4 has not been selected, the processing returns to the step S52.

At the step S60, the CPU 40 executes a step count data reception process. The step count data reception process is a process of transferring the step count data stored in the pedometer 92 to the flash memory 44 of the game apparatus 12. The step count data reception process will be described in detail later. When the step count data reception process ends, the processing returns to the step S52.

(Answer Process in Game Apparatus)

The following will describe in detail the answer process at the step S54 in FIG. 17 with reference to FIGS. 18 to 22.

When the answer process is started, at a step S70, the CPU 40 selects a question message to the user currently operating the game apparatus 12 as a to-be-answered question message from the unanswered question message data D5 stored in the flash memory 44. The CPU 40 reads out from the flash memory 44 the first question or message among the one or more questions or messages contained ins the to-be-answered question message.

At a step S71, the CPU 40 determines whether or not the question or message read out from the flash memory 44 is a "multiple-choice question". When the question or message is a "multiple-choice question", the processing proceeds to a step S72 When the question or message is not a "multiple-choice question", the processing proceeds to a step S73.

At the step S72, the CPU 40 executes a multiple-choice answer process. The multiple-choice answer process is a process of displaying the "multiple-choice question" to the user, and of causing the user to input an answer to the question. The multiple-choice answer process will be described in detail later. When the multiple-choice answer process ends, the processing proceeds to a step S78.

At the step S73, the CPU 40 determines whether or not the question or message read out from the flash memory 44 is a "character-input-type question". When the question or message is a "character-input-type question", the processing proceeds to a step S74. When the question or message is a "character-input-type question", the processing proceeds to a step S75.

At the step S74, the CPU 40 executes a character-input-type answer process. The character-input-type answer process is a process of displaying the "character-input-type question" to the user, and of causing the user to input an answer to the question. The character-input-type answer process will be described in detail later. When the character-input-type answer process ends, the processing proceeds to the step S78.

At the step S75, the CPU 40 determines whether or not the question or message read out from the flash memory 44 is a "numeric-input-type question". When the question or message is a "numeric-input-type question", the processing proceeds to a step S76. When the question or message is not a "numeric-input-type question", the processing proceeds to a step S77.

At the step S76, the CPU 740 executes a numeric-input-type answer process. The numeric-input-type answer process is a process of displaying the "numeric-input-type question" to the user, and of causing the user to input an answer to the question. The numeric-input-type answer process will be described in detail later. When the numeric-input-type answer process ends, the processing proceeds to the step S78.

At the step S77, the CPU 40 executes a message display process. The message display process is a process of displaying a "message" to the user. The message display process will be described in detail later. When the message display process ends, the processing proceeds to the step S78.

At the step S78, the CPU 40 determines whether or not there is the next question or message in the current to-be-answered question message. When there is the next question or message, the processing proceeds to a step S79. When there is not the next question or message (i.e. when inputs of answers to all the questions or messages contained in the to-be-answered question message have been completed), the processing proceeds to a step S80.

At the step S79, the CPU 40 reads out from the flash memory 44 the next question or message contained in the current to-be-answered question message. Then, the processing proceeds to a step S71.

Figure 28:
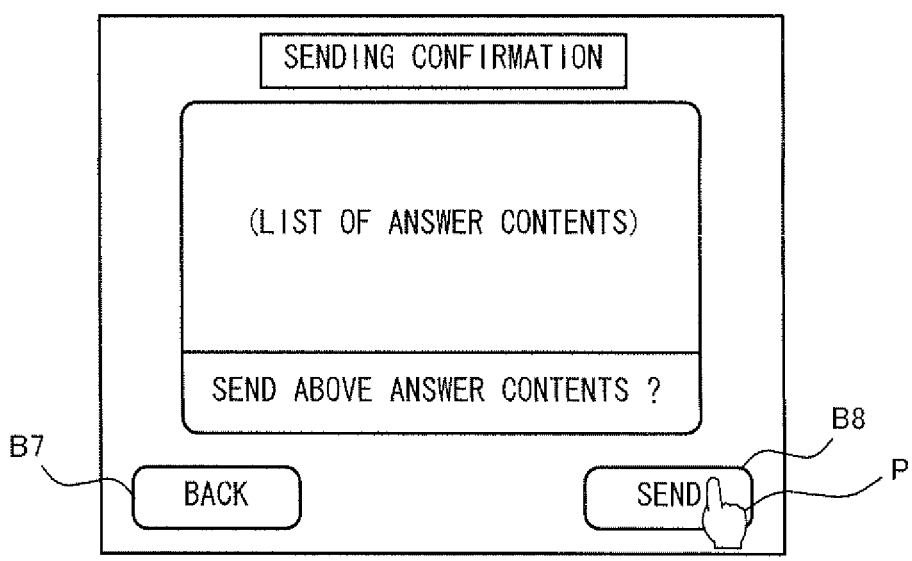
FIG. 28 is a view showing an example of a sending confirmation screen.

At the step S80, the CPU 40 displays a sending confirmation screen on the monitor 34, for example, as shown in FIG. 28. The user looks at a list of answer contents being displayed in the sending confirmation screen to confirm the contents of the answer message. If there is no need to change the contents of the answer message, the user selects a "SEND" button B8 by using the pointer P. If the user desires to change the contents of the answer message, the user selects a "BACK" button B7 by using the pointer P.

At a step S81, the CPU 40 determines whether or not the "SEND" button B8 has been selected. When the "SEND" button 38 has been selected, the processing proceeds to a step S82. When the "SEND" button B8 has not been selected, the processing proceeds to a step S85.

At the step S82, the CPU 40 reads out from the flash memory 44 biological information of the user (i.e. the user selected at the step S50 in FIG. 17) currently operating the game apparatus 12. For example, when the user currently operating the game apparatus 12 is the user B, the CPU 40 reads out the weight data D2*b*, the exercise time data D3*b*, and the step count data D4*b* of the user B which are stored in the flash memory 44. At this time, if information of measurement dates has been added to the biological information stored in the flash memory 44, the CPU 40 may read out only biological information measured during a past constant period (e.g. during the past one month). In the present embodiment, the biological information is obtained from the flash memory 44. However, the present invention is not limited thereto, and the biological information may be obtained from another storage unit inside or outside the game apparatus 12.

At a step S83, the CPU 40 generates a transmission file by combining the created answer message and the biological information, read out from the flash memory 44 at the step S82, into one file.

At a step S84, the CPU 40 transmits the transmission file generated at the step S83 to the healthcare professional terminal 90. Then, the answer process ends. Regarding transmission of a file from the game apparatus 12 to the healthcare professional terminal 90, for example, a generated transmission file can be transmitted as an attached file of an e-mail message by using a general transfer protocol of e-mail. In this case, the e-mail message may be blank or a fixed phrase may be contained in the e-mail message.

At the step S85, the CPU 40 determines whether or not the "BACK" button B7 has been selected. When the "BACK" button B7 has been selected, the processing proceeds to a step S86. When the "BACK" button B7 has not been selected, the processing returns to the step S80.

At the step S86, the CPU 40 reads out again from the flash memory 44 the final question or message contained in the current to-be-answered question message. Then, the processing returns to the step S71. When the "BACK" button B7 is selected in the sending confirmation screen, the display may return to the first question or message instead of returning to the final question or message.

(Multiple-Choice Answer Process in Game Apparatus)

Figure 18:
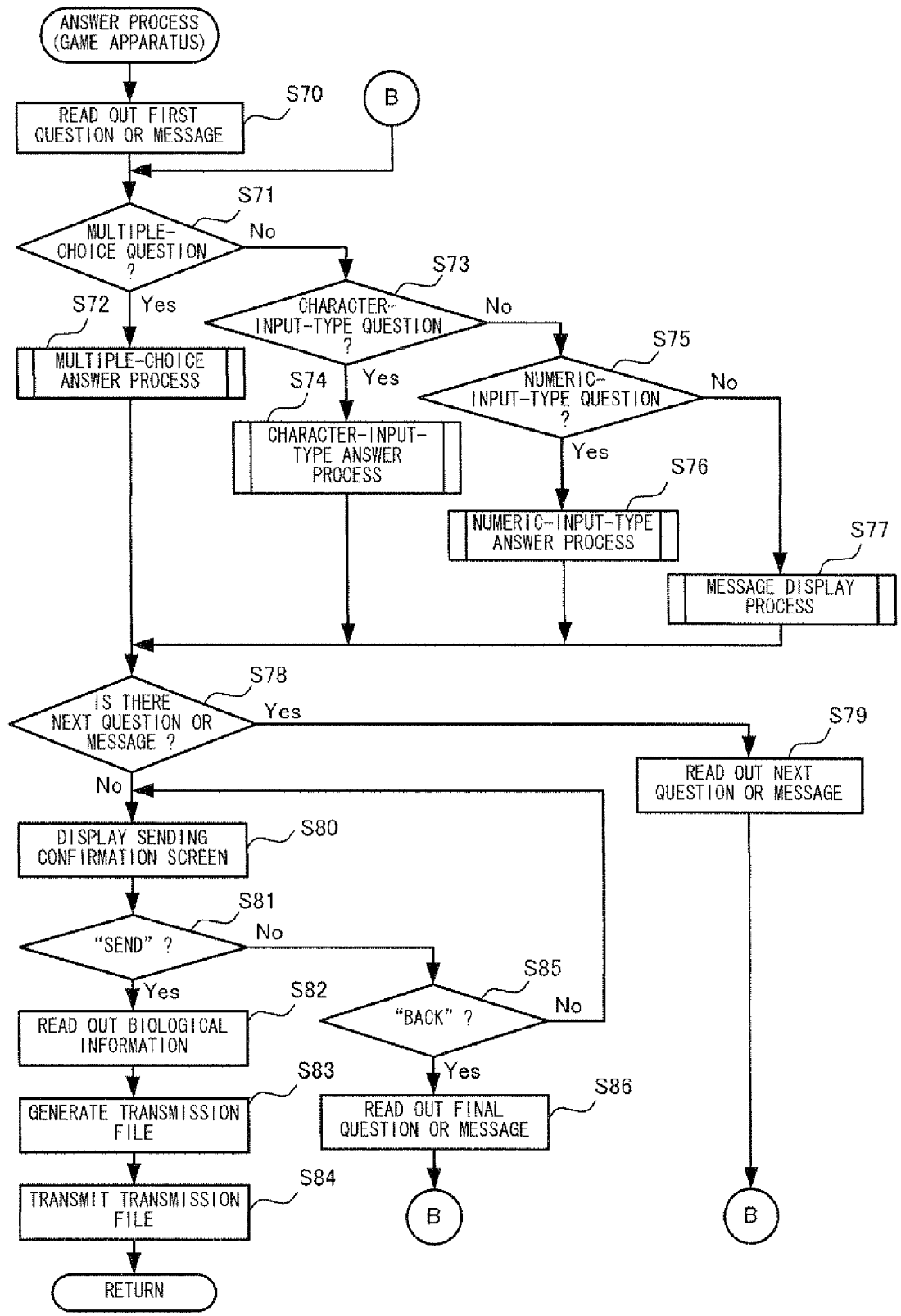
FIG. 18 is a flow chart showing a procedure of an answer process executed by the game apparatus.
Figure 19:
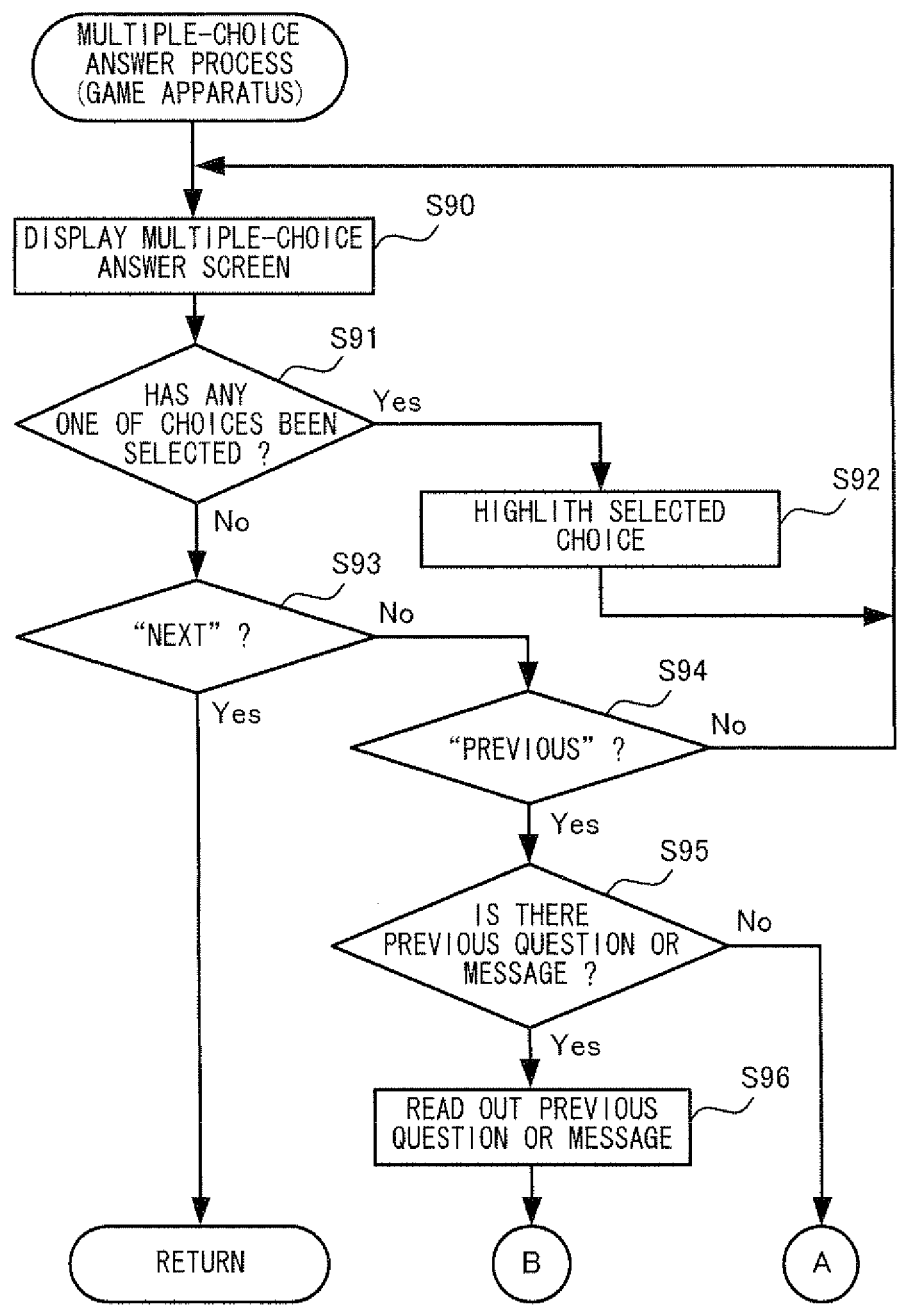
FIG. 19 is a flow chart showing a procedure of a multiple-choice answer process executed by the game apparatus.

The following will describe in detail the multiple-choice answer process at the step S72 in FIG. 18 with reference to FIG. 19.

When the multiple-choice answer process is started, at a step S90, the CPU 40 displays a multiple-choice answer screen as shown in FIG. 25. The multiple-choice answer screen includes the question section Q1, the choice section A1, a "PREVIOUS" button B5, and a "NEXT" button B6.

At a step S91, the CPU 40 determines whether or not any one of the choices displayed in the choice section A1 has been selected by the user. When any one of the choices has been selected, the processing proceeds to a step S92. When any one of the choices has not been selected, the processing proceeds to a step S93. The selection of the choice by the user is performed by operating the controller 22.

At the step S92, the CPU 40 highlights the choice selected by the user. Then, the processing returns to the step S90. Examples of the highlighting include putting a checkmark to the head of the designated choice as shown in FIG. 25; and changing the font color or the background color of the designated choice.

At the step S93, the CPU 40 determines whether or not the "NEXT" button" button B6 has been selected by the user. When the "NEXT" button" button B6 has been selected, the multiple-choice answer process ends, and the processing proceeds to the step S78 in FIG. 18. When the "NEXT" button" button B6 has not been selected, the processing proceeds to a step S4.

At the step S94, the CPU 40 determines whether or not the "PREVIOUS" button B5 is selected by the user. When the "PREVIOUS" button B5 is selected, the processing proceeds to a step S95. When the "PREVIOUS" button B5 is not selected, the processing returns to the step S90.

At the step S95, the CPU 40 determines whether or not there is a previous question or message in the current to-be-answered question message. When there is a previous question or message, the processing proceeds to a step S96. When there is not a previous question or message (i.e. when the question or message being currently displayed is the first question or message in the current to-be-answered question message), the multiple-choice answer process ends, and the processing returns to the step S52 (i.e. the display returns to the menu display screen).

At the step S96, the CPU 40 reads out from the flash memory 44 the previous question or message contained in the current to-be-answered question message. Then, the multiple-choice answer process ends, and the processing returns to the step S71 in FIG. 18.

(Character-Input-Type Answer Process in Game Apparatus)

Figure 20:
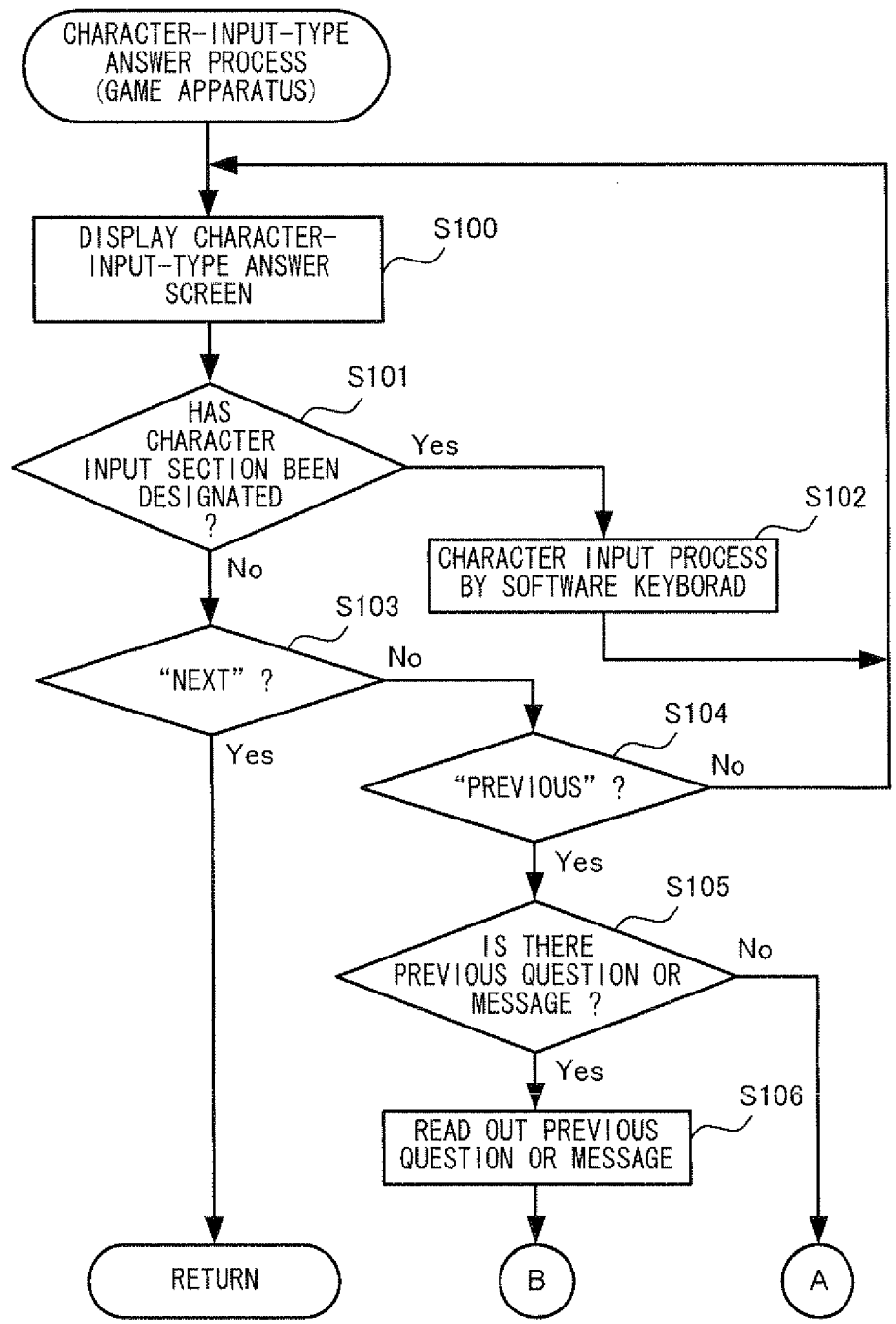
FIG. 20 is a flow chart showing a procedure of a character-input-type answer process executed by the game apparatus.

The following will describe in detail the character-input-type answer process at the step S74 in FIG. 18 with reference to FIG. 20.

When the character-input-type answer process is started, at a step S100, the CPU 40 displays the character-input-type answer screen as shown in FIG. 26. The character-input-type answer screen includes the question section Q2, the character input section A2, the "PREVIOUS" button B5, and the "NEXT" button B6.

At a step S101, the CPU 40 determines whether or not the character input section A2 has been designated by the user. When the character input section A2 has been designated, the processing proceeds to a step S102. When the character input section A2 has not been designated, the processing proceeds to a step S103. The designation of the character input section A2 by the user is performed by operating the controller 22.

At the step S102, the CPU 40 accepts a character input performed by the user using a software keyboard. Then, the processing returns to the step S100. The character input using the software keyboard is performed by the user designating sequentially desired keys in the keyboard displayed on the screen by using the pointer P.

At the step S103, the CPU 40 determines the "NEXT" button 36 has been selected by the user. When the "NEXT" button 36 has been selected, the character-input-type answer process ends, and the processing proceeds to the step S78 in FIG. 18. When the "NEXT" button B6 has not been selected, the processing proceeds to a step S104.

At the step S104, the CPU 40 determines whether or not the "PREVIOUS" button B5 has been selected by the user. When the "PREVIOUS" button 35 has been selected, the processing proceeds to a step S015. When the "PREVIOUS" button B5 has not been selected, the processing returns to the step S100.

At the step S105, the CPU 40 determines whether or not there is a previous question or message in the current to-be-answered question message. When there is a previous question or message, the processing proceeds to a step S106. Where there is not a previous question or message, the character-input-type answer process ends, and the processing proceeds to the step S52 in FIG. 17.

At the step S106, the CPU 40 reads out form the flash memory 44 the previous question or message contained in the current to-be-answered question message. Then, the character-input-type answer process ends, and the processing returns to the step S71 in FIG. 18.

(Numeric-Input-Type Answer Process in Game Apparatus)

Figure 21:
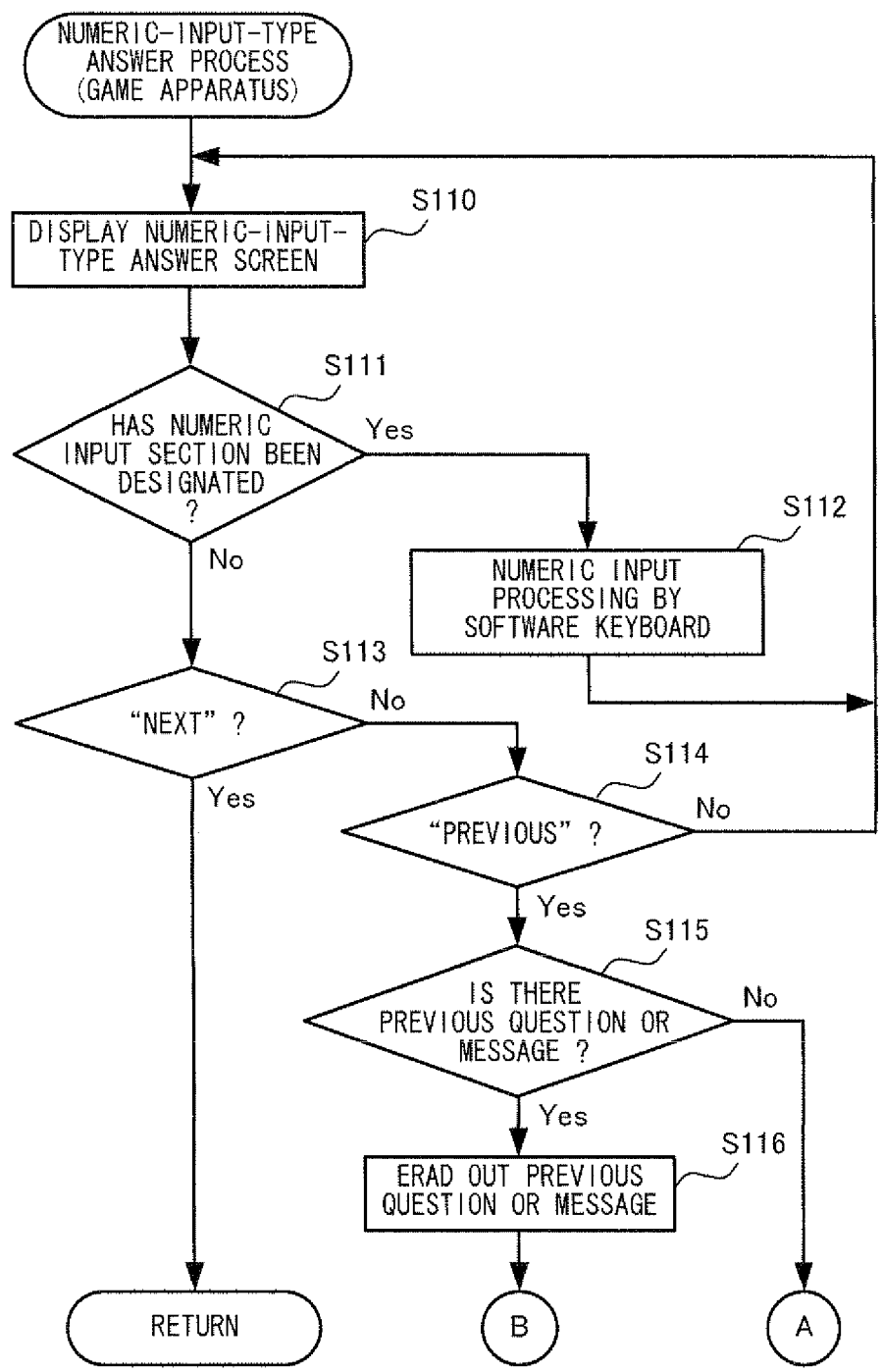
FIG. 21 is a flow chart showing a procedure of a numerical input answer process executed by the game apparatus.

The following will describe in detail the numeric-input-type answer process at the step S76 in FIG. 18 with reference to FIG. 21.

When the numeric-input-type answer process is started, at a step S110, the CPU 40 displays a numeric-input-type answer screen as shown in FIG. 27. The numeric-input-type answer screen includes the question section Q3, the numeric input section A3, the "PREVIOUS" button B5, and the "NEXT" button B6.

At a step S111, the CPU 40 determines whether or not the numeric input section A3 has been designated by the user. When the numeric input section A3 has been designated, the processing proceeds to a step S112. When the numeric input section A3 has not been designated, the processing proceeds to a step S113. The designation of the numeric input section A3 by the user is performed by operating the controller 22.

At the step S112, the CPU 40 accepts a numeric input from the user using a software keyboard (only a numeric keypad). Then, the processing returns to the step S110. The numeric input using the software keyboard is performed by the user designating sequentially desired keys in the numeric keypad displayed on the screen by using the pointer P.

At the step S113, the CPU 40 determines whether or not the "NEXT" button 36 has been selected by the user. When the "NEXT" button B6 has been selected, the numeric-input-type answer process ends, and the processing proceeds to the step S78 in FIG. 18. When the "NEXT" button 36 has not been selected, the processing proceeds to a step S114.

At the step S114, the CPU 40 determines whether or not the "PREVIOUS" button B5 has been selected by the user. When the "PREVIOUS" button B5 has been selected, the processing proceeds to a step S115. When the "PREVIOUS" button 35 has not been selected, the processing returns to the step S110.

At the step S115, the CPU 40 determines whether or not a previous question or message in the current to-be-answered question message. When there is a previous question or message, the processing proceeds to a step S116. When there is not a previous question or message, the numeric-input-type answer process ends, and the processing returns to the step S52 in FIG. 17.

At the step S116, the CPU 40 reads out from the flash memory 44 the previous question or message contained in the current to-be-answered question message. Then, the numeric-input-type answer process ends, and the processing returns to the step S71 in FIG. 18.

(Message Display Process In Game Apparatus)

The following will describe in detail the message display process at the step S77 in FIG. 18 with reference to FIG. 22.

When the message display process is started, at a step S120, the CPU 40 displays a message display screen as shown in FIG. 24. The message display screen includes the message section M1, the "PREVIOUS" button 35, and the "NEXT" button 86.

At a step S121, the CPU 40 determines whether or not the "NEXT" button B6 has been selected by the user. When the "NEXT" button BE has been selected, the message display process ends, and the processing proceeds to the step S78 in FIG. 18. When the "NEXT" button B6 has not been selected, the processing proceeds to a step S122.

At the step S122, the CPU 40 determines whether or not the "PREVIOUS" button 35 has been selected by the user. When the "PREVIOUS" button 35 has been selected, the processing proceeds to a step S123. When the "PREVIOUS" button B5 has not been selected, the processing returns to the step S120.

At the step S123, the CPU 40 determines whether or not there is a previous question or message in the current to-be-answered question message. When there is a previous question or message, the processing proceeds to a step S124. When there is not a previous question or message, the message display process ends, and the processing returns to the step S52 in FIG. 17.

At the step S124, the CPU 40 reads out from the flash memory 44 the previous question or message contained in the current to-be-answered question message. Then, the message display process ends, and the processing returns to the step S71 in FIG. 18.

In the flow charts of FIGS. 19 and 21, even when the choice selection, character input, or numeric input has not been performed, the processing can proceed to the next question or message by the user selecting the "NEXT" button B6. However, the processing may not be capable of proceeding to the next question or message unless the choice selection, character input, or numeric input has been performed (e.g. the "Next" button" button 36 is grayed out until the choice selection, character input, or numeric input is performed).

(Step Count Data Reception Process in Game Apparatus)

Figure 29:
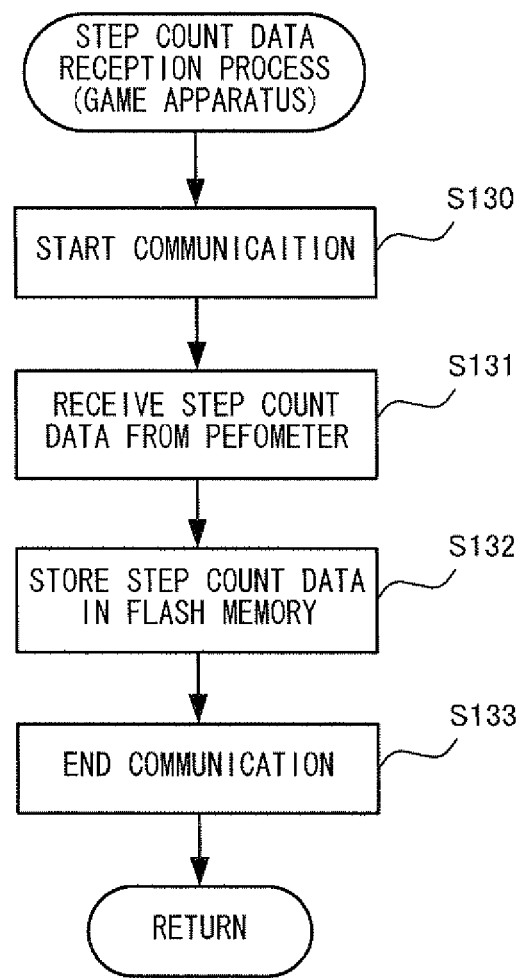
FIG. 29 is a flow chart showing a procedure of a step count data reception process executed by the game apparatus.

The following will describe in detail the step count data reception process at the step S60 in FIG. 17 with reference to FIG. 29.

When the step count data reception process is started, at a step S130, the CPU 40 starts communication with the pedometer 92.

At a step S131, the CPU 40 receives step count data from the pedometer 92. At this time, the CPU 40 may receive all step count data stored in the pedometer 92, or may receive only a part of step count data stored in the pedometer 92 (e.g. the step count data and the step count data measured during a predetermined period (e.g. during the past one month) of the user (i.e. the user selected at the step S50 in FIG. 17) currently operating the game apparatus 12.

At a step S132, the CPU 40 stores the step count data, received from the pedometer 92, in the flash memory 44.

At a step S133, the CPU 40 ends the communication with the pedometer 92. Then, the step count data reception process ends.

(Answer Reception Process in Healthcare Professional Terminal)

Figure 30:
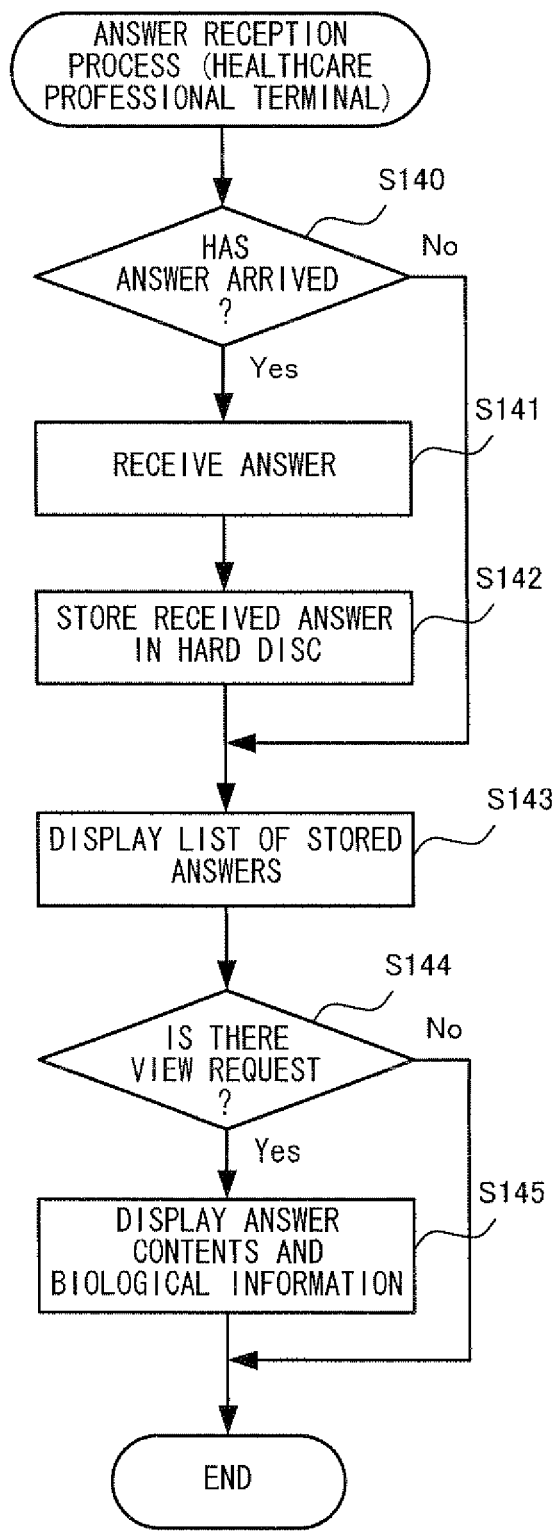
FIG. 30 is a flow chart showing a procedure of an answer reception process executed by the healthcare professional terminal.

The following will describe an operation of the healthcare professional terminal 90 when an answer message reception application is executed in the healthcare professional terminal 90. The answer message reception application is typically supplied to the healthcare professional terminal 90 through a computer-readable storage medium such as an optical disc and the like or through the Internet, and installed in the hard disk of the healthcare professional terminal 90. The function of the aforementioned question message creation application and the function of the answer message reception application may be realized by one application. FIG. 30 is a flow chart showing a procedure of an answer reception process executed by the CPU of the healthcare professional terminal 90 in accordance with the answer message reception application.

When the answer reception process is started, at a step S140, the CPU of the healthcare professional terminal 90 accesses a mail server, and determines whether or not the mail server has received an answer message from the healthcare recipient (i.e. the game apparatus 12). When the mail server has received an answer message from the healthcare recipient, the processing proceeds to a step S141. When the mail server has not received any answer messages from the healthcare recipient, the processing proceeds to a step S143.

At the step S141, the CPU of the healthcare professional terminal 90 receives the answer message (specifically, a file including an answer message and biological information as described above) received by the mail server from the healthcare recipient.

At a step S142, the CPU of the healthcare professional terminal 90 stores the answer message received at the step S141 in the hard disk of the healthcare professional terminal 90.

At the step S143, the CPU of the healthcare professional terminal 90 displays a list of answer messages, stored in the hard disk, on the monitor of the healthcare professional terminal 90.

At a step S144, the CPU of the healthcare professional terminal 90 determines whether or not there is a view request from the operator (the healthcare professional) for any one of the answer messages in the list displayed on the monitor. When there is a view request for any one of the answer messages, the processing proceeds to a step S145. When there is not a view request for any one of the answer messages, the answer reception process ends.

At the step S145, the CPU of the healthcare professional terminal 90 displays the answer message, for which the view request is performed by the operator, on the monitor together with the corresponding biological information.

As described above, according to the present embodiment, when the answer message to the question message from the healthcare professional is transmitted from the game apparatus 12 to the healthcare professional terminal 90, the biological information of the healthcare recipient is automatically read out from the flash memory 44 and transmitted to the healthcare professional terminal 90 together with the answer message. Thus, when the healthcare recipient transmits the answer message, inputting of the biological information is omitted, and the biological information is assuredly transmitted. In addition, because the healthcare professional can fully confirm the biological information required for health guidance, the healthcare professional can properly and efficiently perform health guidance.

The present embodiment has described the case where the load controller 36 and the pedometer 92 are used as apparatuses for measuring biological information. The present invention is not limited thereto. For example, biological information (blood pressure data and body temperature data) may be obtained from a blood-pressure gauge and a clinical thermometer.

Further, in the present embodiment, the game apparatus 12 obtains biological information from an external apparatus such as the load controller 36 and the pedometer 92. However, the present invention is not limited thereto, and the game apparatus 12 may have a biological information measuring function. As such a game apparatus, for example, there is a game apparatus having a load sensor for measuring a load exerted by the user standing on the game apparatus.

Further, for the communication between the game apparatus 12 and the load controller 36 and the communication between the game apparatus 12 and the pedometer 92, arbitrary communication methods (e.g. the Bluetooth, infrared communication, other wireless communication methods, wire communication methods, public communication lines such as the Internet, wired lines such as cable) can be used.

Further, the present embodiment has described the case where a general-purpose personal computer is used as the healthcare professional terminal 90 and the game apparatus 12 is used as the healthcare recipient terminal. However, the present invention is not limited thereto, arbitrary information processing apparatuses (personal computers, stationary game apparatuses, hand-held game machines, mobile phones, PDAs) can be used as the healthcare professional terminal and the healthcare recipient terminal.

Further, in the present embodiment, transmission and reception of messages (a question message and an answer message) between the game apparatus 12 and the healthcare professional terminal 90 are performed by using a well-known protocol of e-mail. However, the present invention is not limited thereto, and another method using the Internet or a wire or wireless communication method may be used.

Further, the data structures of a question message and an answer message are not limited to the structures described in the above embodiment, and arbitrary data structures can be used. The formats of a question and a message are not limited to "multiple-choice question", "character-input-type question", "numeric-input-type question", and "message" which are described in the above embodiment.

Further, the present embodiment has described the case where an answer message and biological information are combined into one file. However, the present invention is not limited thereto.

Further, the present embodiment has described the health guidance support system in which a healthcare nurse or the like performs health guidance for a healthcare recipient. However, the present invention is not limited thereto, and is also applicable to purposes other than health guidance.

While the invention has been described in detail, the foregoing description is in all aspects illustrative and not restrictive. It is understood that numerous other modifications and variations can be devised without departing from the scope of the invention,

What is claimed is:

1. A biological information management system comprising a first information processing apparatus and a second information processing apparatus configured to communicate with the first information processing apparatus,
    the first information processing apparatus including:
        biological information obtaining unit configured to obtain biological information;
        first message creation unit configured to create a first message based on an input operation of an operator of the first information processing apparatus; and
        first message transmission unit configured to transmit the biological information obtained by the biological information obtaining unit and the first message created by the first message creation unit to the second information processing apparatus,
    the second information processing apparatus including:
        first message reception unit configured to receive the biological information and the first message from the first information processing apparatus; and
        a storage unit configured to store the biological information and the first message which are received by the first message reception unit,
    wherein the first message creation unit is further configured to generate a transmission request that instructs the first message transmission unit to transmit the first message to the second information processing apparatus, and the first message transmission unit is further configured to, in response to receiving the transmission request, obtain the biological information and then transmit the first message and the biological information to the second information processing apparatus.

2. The biological information management system according to claim 1, wherein upon receiving a transmission instruction of the first message from the operator of the first information processing apparatus, the first message transmission unit is configured to automatically obtains the biological information by the biological information obtaining unit and to transmit the obtained biological information together with the first message to the second information processing apparatus.

3. The biological information management system according to claim 1, further comprising a biological information measuring apparatus including:
    biological information measuring unit configured to measure biological information; and
    biological information transmission unit configured to transmit the biological information measured by the biological information measuring unit to the first information processing apparatus,
    wherein the biological information obtaining unit includes a biological information reception unit configured to receive the biological information from the biological information measuring apparatus.

4. The biological information management system according to claim 3, wherein the biological information measuring unit is further configured to measure a weight, or count the number of steps taken, as the biological information.

5. The biological information management system according to claim 3, wherein:
the first information processing apparatus further includes a processor for executing a process using the biological information measuring unit, and a process time counting unit configured to count a time of the process executed by the processor; and
the biological information obtaining unit is further configured to obtain the time counted by the process time counting unit.

6. The biological information management system according to claim 1, wherein the biological information obtaining unit includes a biological information measuring unit configured to measure biological information.

7. The biological information management system according to claim 1, wherein:
the first information processing apparatus further includes a storage unit configured to store the biological information obtained by the biological information obtaining unit and measurement date information of the biological information; and
the first message transmission unit refers to the measurement date information and is configured to transmit biological information of a predetermined period.

8. The biological information management system according to claim 1, wherein the first message transmission unit is configured to transmit the biological information and the first message as one file to the second information processing apparatus.

9. The biological information management system according to claim 1, wherein the biological information is non-cognitive physical information the system acquires about the operator's body and the user input is cognitive information the operator voluntarily provides in response to a question.

10. The biological information management system according to claim 1, wherein the first message transmission unit is configured to send the first message and the biological information to the second information processing apparatus in a single file.

11. The biological information management system according to claim 1, wherein the system includes a handheld device operable to provide information to the first message creation unit for use in creation of the first message, and a second device that is operable to, at least temporarily, be in contact with the operator's feet in order to obtain the biological information.

12. The biological information management system according to claim 1, wherein the biological information is obtainable by the biological information obtaining unit of the first information processing apparatus from another information processing apparatus.

13. The biological information management system according to claim 1, wherein the biological information is obtainable by the first message transmission unit of the first information processing apparatus from a memory thereof.

14. The biological information management system according to claim 1, wherein:
the second information processing apparatus further includes:
second message creation unit configured to create a second message based on an input operation of an operation of the second information processing apparatus; and
second message transmission unit configured to transmit the second message created by the second message creation unit to the first information processing apparatus;
the first information processing apparatus further includes:
second message reception unit configured to receive the second message from the second information processing apparatus; and
the first message creation unit configured to create the first message based on the second message received by the second message reception unit.

15. The biological information management system according to claim 14, wherein:
the second message is a question message;
the first information processing apparatus further includes a question execution unit configured to execute a question based on the question message received by the second message reception unit; and
the first message creation unit is configured to create, as the first message, an answer message to the question executed by the question execution unit.

16. A non-transitory computer-readable storage medium storing a computer program for a biological information management system comprising a first information processing apparatus and a second information processing apparatus configured to communicate with the first information processing apparatus, the computer program causing a computer of the first information processing apparatus to execute:
obtaining biological information;
creating a first message based on an input operation of an operator of the first information processing apparatus;
generating a request to transmit the first message to the second information processing apparatus; and
transmitting, in response to the generated request, the obtained biological information and the created first message to the second information processing apparatus.

17. An information processing apparatus used as a first information processing apparatus in a biological information management system comprising the first information processing apparatus and a second information processing apparatus configured to communicate with the first information processing apparatus, the information processing apparatus comprising:
a processor; and
a memory coupled to said processor, said memory storing instructions that, when executed by said processor, control said processor to:
obtain biological information;
create a first message based on an input operation of an operator of the first information processing apparatus;
generate a request to transmit the first message to the second information processing apparatus; and
transmit, in response to the generated request, the obtained biological information and the created first message to the second information processing apparatus.

18. A health guidance support system for a healthcare professional to perform health guidance for a healthcare recipient, the health guidance support system comprising:
a healthcare professional terminal configured for operation by the healthcare professional; and a healthcare recipient terminal configured for operation by the healthcare recipient and configured to communicate with the healthcare professional terminal, the healthcare professional terminal including:
- question message creation unit configured to create a question message in accordance with an input operation of the healthcare professional; and
- question message transmission unit configured to transmit the question message from the healthcare professional terminal to the healthcare recipient terminal, the healthcare recipient terminal including:
- question message reception unit configured to receive the question message from the healthcare professional terminal;
- question message displaying unit configured to display the received question message to the healthcare recipient;
- answer message creation unit configured to create an answer message to the question message in accordance with an input operation of the healthcare recipient; and
- answer message transmission unit configured to, upon receiving a transmission instruction from the healthcare recipient, automatically obtain biological information regarding health of the healthcare recipient from a storage unit that is provided in or connected to the healthcare recipient terminal, and transmit the biological information together with the created answer message to the healthcare professional terminal, the healthcare professional terminal further including:
- answer message reception unit configured to receive the answer message together with the biological information from the healthcare recipient terminal; and
- answer message displaying unit configured to display the received answer message and the biological information to the healthcare professional.

19. The health guidance support system according to claim 18, wherein:
- the healthcare recipient terminal is a game apparatus; and
- the answer message transmission unit is configured to obtain the biological information regarding the health of the healthcare recipient from saved data of a game executed previously in the healthcare recipient terminal.

20. A method of operating a biological information management system comprising a first information processing apparatus and a second information processing apparatus configured to communicate with the first information processing apparatus, the method comprising:
- obtaining biological information;
- creating a first message based on an input operation of an operator of the first information processing apparatus;
- generating a request to transmit the first message to the second information processing apparatus; and
- transmitting, in response to the generated request, the obtained biological information and the created first message to the second information processing apparatus.

* * * * *